US010604473B2

(12) United States Patent
Kahn et al.

(10) Patent No.: US 10,604,473 B2
(45) Date of Patent: Mar. 31, 2020

(54) LIPIDS THAT INCREASE INSULIN SENSITIVITY AND METHODS OF USING THE SAME

(71) Applicants: Beth Israel Deaconess Medical Center, Inc., Boston, MA (US); President and Fellows of Harvard College, Cambridge, MA (US)

(72) Inventors: Barbara B. Kahn, Cambridge, MA (US); Mark A. Herman, Needham, MA (US); Alan Saghatelian, La Jolla, CA (US); Edwin Homan, New York, NY (US)

(73) Assignees: Beth Israel Deaconess Medical Center, Inc., Boston, MA (US); President and Fellows of Harvard College, Cambridge, MA (US)

( * ) Notice: Subject to any disclaimer, the term of this patent is extended or adjusted under 35 U.S.C. 154(b) by 45 days.

(21) Appl. No.: 14/775,399

(22) PCT Filed: Mar. 14, 2014

(86) PCT No.: PCT/US2014/029329

§ 371 (c)(1),
(2) Date: Sep. 11, 2015

(87) PCT Pub. No.: WO2014/144777

PCT Pub. Date: Sep. 18, 2014

(65) Prior Publication Data

US 2016/0221925 A1 Aug. 4, 2016

Related U.S. Application Data

(60) Provisional application No. 61/794,930, filed on Mar. 15, 2013, provisional application No. 61/794,609, filed on Mar. 15, 2013.

(51) Int. Cl.

| | |
|---|---|
| ***C07C 69/22*** | (2006.01) |
| ***G01N 33/92*** | (2006.01) |
| ***C07D 495/04*** | (2006.01) |
| ***G01N 33/53*** | (2006.01) |

(52) U.S. Cl.

CPC ............ *C07C 69/22* (2013.01); *C07D 495/04* (2013.01); *G01N 33/5308* (2013.01); *G01N 33/92* (2013.01); *G01N 2800/02* (2013.01); *G01N 2800/52* (2013.01)

(58) Field of Classification Search

CPC ....... C07C 51/412; C07C 59/72; C07C 69/22; A61K 31/192; C07D 495/04; G01N 2800/02; G01N 2800/52; G01N 33/5308; G01N 33/92

See application file for complete search history.

(56) References Cited

U.S. PATENT DOCUMENTS

| | | | | |
|---|---|---|---|---|
| 4,629,736 A * | 12/1986 | Tsukamoto | ........... C07C 59/125 514/14.9 |
| 4,639,369 A | 1/1987 | Ciaudelli | |
| 5,362,878 A * | 11/1994 | Chang | .................. C07C 233/25 544/317 |
| 5,780,237 A | 7/1998 | Bursten et al. | |
| 5,993,861 A | 11/1999 | Fogel | |
| 6,290,973 B1 | 9/2001 | Hawkins et al. | |
| 2007/0092475 A1 | 4/2007 | Wohlman | |
| 2008/0015227 A1 | 1/2008 | Kym et al. | |
| 2015/0133551 A1 | 5/2015 | Kahn et al. | |
| 2018/0194714 A1 | 7/2018 | Kahn et al. | |
| 2019/0151276 A1 | 5/2019 | Kahn et al. | |

FOREIGN PATENT DOCUMENTS

| | | |
|---|---|---|
| JP | 2000 225397 | 8/2000 |
| JP | 2000226397 | 8/2000 |
| JP | 2001270851 A * | 10/2001 |
| WO | WO 94/06014 | 3/1994 |
| WO | WO 2004/089869 A1 | 10/2004 |
| WO | WO 2013/166431 A1 | 11/2013 |
| WO | WO 2014/144777 A2 | 9/2014 |
| WO | WO 2017/070515 | 4/2017 |

OTHER PUBLICATIONS

Jiang et al. 2002, Bioorganic and Medicinal Chemistry Letters, 12, pp. 2193-2196.*

Weber et al. 2000, Chemistry and Physics of Lipids, 105, pp. 215-223.*

Gu et al. Langmuir, 2002, 18, pp. 7415-7427.*

Nakamura et al. 2003, Bull. Chem. Soc. Japan, pp. 1011-1022.*

Translation of JP-2001270851A.*

Applewhite et al. (1967, Journal of Organic Chemistry, 32(4), pp. 1173-1178). (Year: 1967).*

Lizuka, K., et al., "Deficiency of Carbohydrate-Activated Transcription Factor ChREBP Prevents Obesity and Improves Plasma Glucose Control in Leptin-Deficient (OB/OB) Mice," *Am. J. Physiol. Endocrinol. Metab.*, 291 (2): E358-E364 (2006).

King, A.J., et al. ,"Diacylglycerol Acyltransferase 1 Inhibition Lowers Serum Triglycerides in the Zucker Fatty Rad and the Hyperlipidemic Hamster," *Journal of Pharmacology and Experimental Therapeutics*, 330 (2): 526-531 (2009).

(Continued)

*Primary Examiner* — Kara R McMillian

(74) *Attorney, Agent, or Firm* — Hamilton, Brook, Smith & Reynolds, P.C.

(57) ABSTRACT

The invention provides, inter alia, fatty acyl hydroxy fatty acid (FAHFA; a novel class of estolide-related molecules) and diagnostic and treatment methods for a variety of disorders—including diabetes-related disorders, Metabolic Syndrome, polycystic ovarian syndrome, cancer, and inflammatory disorders—using them; as well as methods of screening for additional compounds that are useful in treating these disorders and/or that modulate FAHFA levels, FAHFA-mediated signaling, and FAHFA-mediated biological effects.

1 Claim, 48 Drawing Sheets

Specification includes a Sequence Listing.

(56) References Cited

OTHER PUBLICATIONS

Bocan, T. M. A., et al., "Comparison of CI-976, an ACAT Inhibitor, and Selected Lipid-Lowering Agents for Antiatherosclerotic Activity in Iliac-Femoral and Thoracic Aortic Lesions," *Arteriosclerosis and Thrombosis, American Heart Association, US*, 11 (34): 1830-1843 (1991).
Boga, C., et al., "Fluorescein Conjugates of 9- and 10-Hydroxystearic Acids: Synthetic Strategies, Photophysical Characterization, and Confocal Microscopy Applications," *Analytical Biochemistry, Academic Press, Inc., New York*, 335 (2): 196-209 (2004).
Notification Concerning Transmittal of International Preliminary Report on Patentability, dated Nov. 13, 2014, for International Application No. PCT/US2013/039532, filed May 3, 2013, entitled "Lipids That Increase Insulin Sensitivity and Methods of Using the Same,".
Notification Concerning Transmittal of International Preliminary Report on Patentability, dated Sep. 24, 2015, for International Application No. PCT/US2014/029329, filed Mar. 14, 2014, entitled "Lipids That Increase Insulin Sensitivity and Methods of Using the Same,".
Amspacher, D.R., et al., "Synthesis of a Reaction Intermediate Analogue of Biotin-Dependent Carboxylases via a Selective Derivatization of Biotin," *Organic Letters* 1(1):99-102 (1999).
Charron, G., et al., "Robust Fluorescent Detection of Protein Fatty-Acylation with Chemical Reporters," *Journal of the American Chemical Society* 131(13):4967-4975 (2009).
Dignass, A. U., et al., "Review article: the aetiopathogenesis of inflammatory bowel disease—immunology and repair mechanisms", *Aliment Pharmacol. Ther.*, vol. 20; Suppl. 4; 9-17 (2004).
Final Office Action for U.S. Appl. No. 14/398,198, entitled: "Lipids That Increase Insulin Sensitivity and Methods of Using the Same", dated Nov. 22, 2016.
Gersemann, M., et al., "Innate immune dysfunction in inflammatory bowel disease", *Journal of Internal Medicine*, vol. 271; 421-428 (2012).
Harlan Laboratories: Teklad 6% Fat Mouse/Rat diet,: 2008, XP002703263, Retrieved from the Internet: URL:http://www.harlan.com/products_and_services/research_models_and_services/laboratory_animal_diets/teklad_natural_ingredient_diets/teklad_traditional_diets/rodent_diets/teklad_6_mouse_rat_diet_002.hl [Retrieved on Jul. 17, 2013].
Non-Final Office Action for U.S. Appl. No. 14/398,198; "Lipids That Increase Insulin Sensitivity and Methods of Using the Same", dated Feb. 19, 2016.
Notification of Transmittal of the International Search Report and Written Opinion for International Application No. PCT/US2013/039532, entitled, "Lipids That Increase Insulin Sensitivity and Methods of Using the Same", dated Aug. 2, 2013.
Pastorelli, L., et al., "Central role of the gut epithelian barrier in the pathogenesis of chronic intestinal inflammation: lessons learned from animal models and human genetics", *Frontiers in Immunology*, vol. 4; Article 280; 1-22 (2013).
Shimoyama, et al., "Chemical Synthesis of Helicobacter pylori Lipopolysaccharide Partial Structures and their Selective Proinflammatory Responses", Dec. 16, 2011; first published Nov. 16, 2011; Chem. Eur. J. 17: 14464-14474 & Supplemental section, pp. 1-39.
Yore, M. M., et al., "Discovery of a Class of Endogenous Mammalian Lipids with Anti-Diabetic and Anti-inflammatory Effects", Cell, vol. 159: 318-332 (2014).
Homan, E.W., "Discovery of Novel Lipid Pathways Associated With the Metabolic Syndrome." Unpublished Doctoral Dissertation, Harvard University (2012).
Homan, E., Discovery of Novel Lipid Pathways Associated With the Metabolic Syndrome; downloaded on Aug. 28, 2014 from Harvard University; 4 pages. URL: http://dash.harvard.edu/handle/1/10310131?show=full.
Harry-O'Kuru, et al., "Synthesis of Estolide Esters from cis-9-Octadecenoic Acid Esolides", JAOCS, 78(3): 219-222 (2001).
Notification of Transmittal of the International Search Report and Written Opinion of the International Searching Authority for PCT/US2014/029329, "Lipids That Increase Insulin Sensitivity and Methods of Using the Same," dated Sep. 30, 2014.
Landham, R. R., et al., "Organotitanate dispersants for BaTiOa and Alz03", *Journal of Materials Science*, Jan. 1, 1987, p. 1681, XP055371293.
Notification of Transmittal of the International Search Report and Written Opinion for International Application No. PCT/US2016/058184, entitled, "Methods of Preventing and Treating Inflammatory Bowel Disease With Branched Fatty Acid Esters of Hydroxy Fatty Acids (FAHFAS)", dated Apr. 18, 2017.
Notification Concerning Transmittal of International Preliminary Report on Patentability (IPRP) and accompanying IPRP and Written Opinion, International Application No. PCT/US2017/036789, entitled, "Fatty Acid Esters of Hydroxy Fatty Acids (FAHFAs) for Use in the Treatment of Type 1 Diabetes", dated Dec. 20, 2018.

* cited by examiner

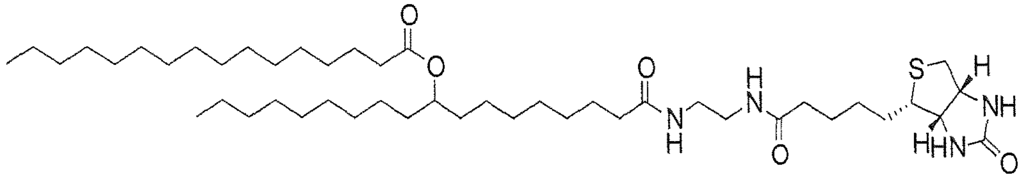
BF-2
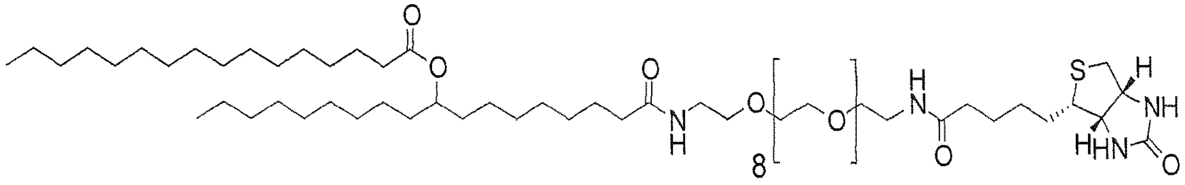
BF-3
FIG. 14
| Characteristics of study subjects – All Obese | |
|---|---|
| N (F:M) | 38 (28:10) |
| Age (y) | 41±11 |
| BMI (kg/m$^2$) | 36.6±4.6 |
| % Body Fat | 41±9 |
Values are Means ±SD
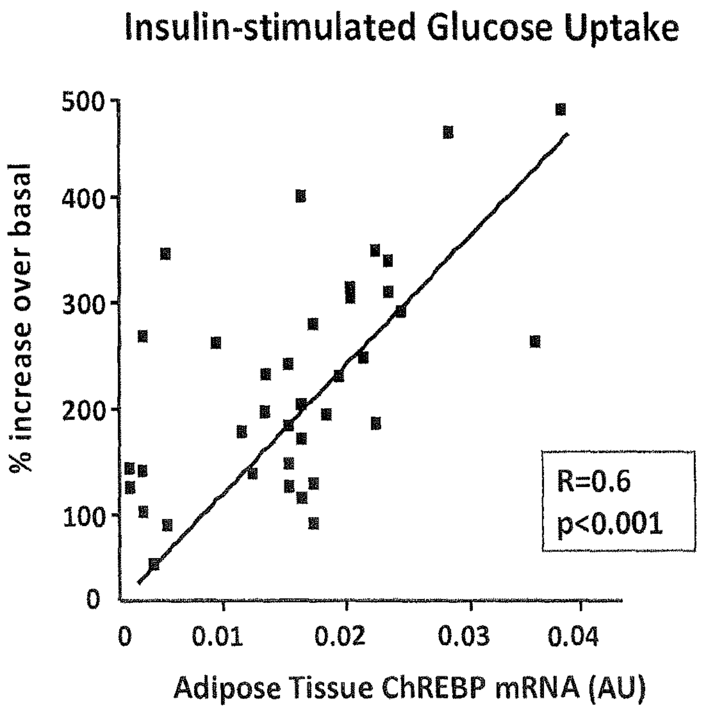
FIG. 15

| *Human Serum* | mg lipid | Novel Lipid (nM) |
|---|---|---|
| serum-1 | 1.6 | 50.7 |
| serum-2 | 3.1 | 83.3 |
| serum-3 | 1.6 | 48.7 |

| *Human Fat* | mg lipid | Novel Lipid (pmol/mg lipid) |
|---|---|---|
| fat-1 (fed) | 123.4 | 1.12 |
| fat-2 (fasted) | 100.1 | 0.97 |

| Characteristic | Lean, insulin-sensitive (N = 8) | Lean, insulin-resistant (N = 8) | Obese, insulin-resistant (N = 8) | P-value (L-IS vs L-IR) | P-value (L-IR vs O-IR) |
|---|---|---|---|---|---|
| Sex (male/female) | 4/4 | 4/4 | 4/4 | | |
| Age (yrs) | 42.2 ± 2.4 | 36.6 ± 2.3 | 39.0 ± 2.6 | | |
| HbA1c (%) | 4.14 ± 0.07 | 4.18 ± 0.05 | 4.09 ± 0.12 | | |
| Body mass index (kg/m$^2$) | 22.3 ± 1.3 | 22.4 ± 1.3 | 31.1 ± 0.9 | 0.94 | < 0.001 |
| Glucose infusion rate (mg/kg/min) | 19.3 ± 2.0 | 8.3 ± 1.3 | 8.1 ± 2.2 | < 0.001 | 0.92 |

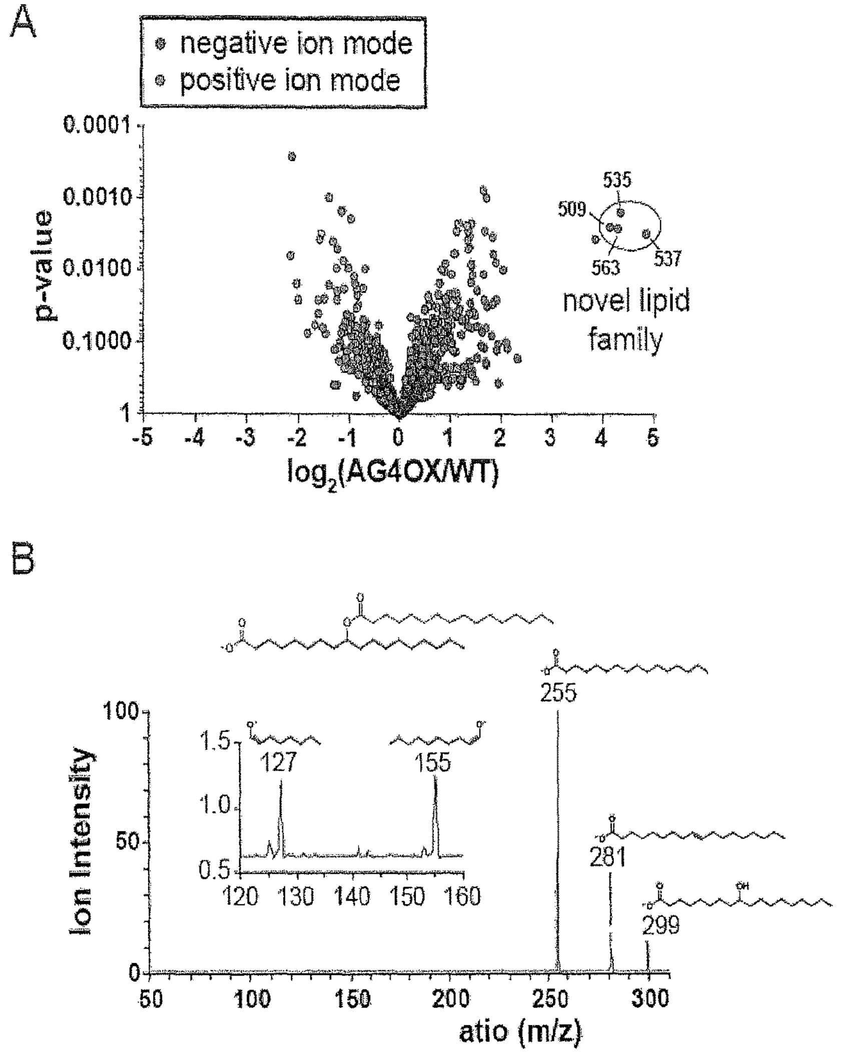
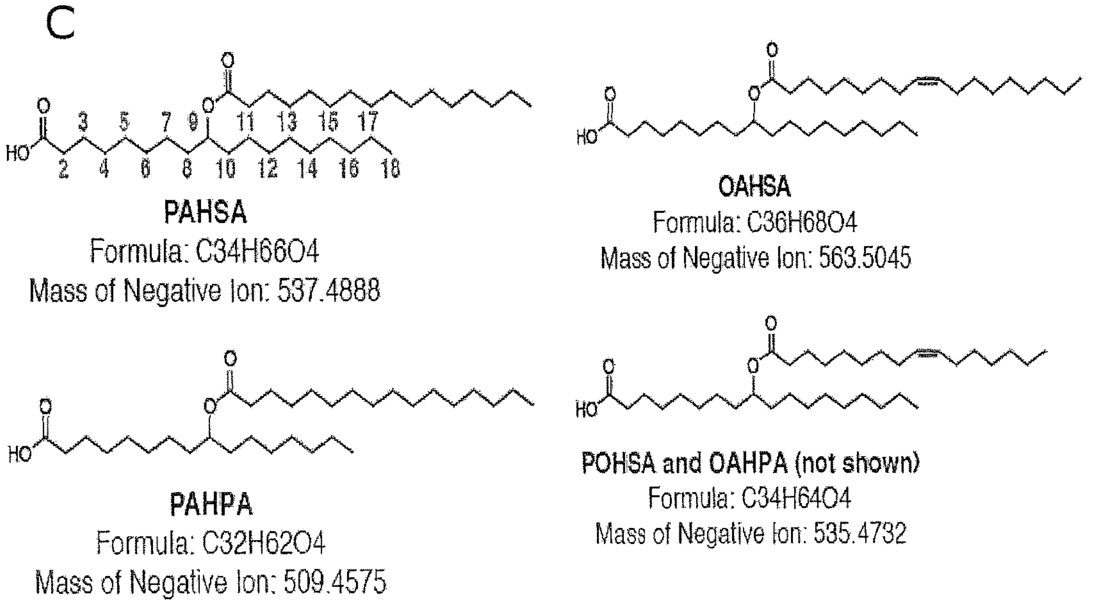
PAHSA
Formula: C34H66O4
Mass of Negative Ion: 537.4888
OAHSA
Formula: C36H68O4
Mass of Negative Ion: 563.5045
PAHPA
Formula: C32H62O4
Mass of Negative Ion: 509.4575
POHSA and OAHPA (not shown)
Formula: C34H64O4
Mass of Negative Ion: 535.4732
FIG. 49A-C D
Fatty Acid | Hydroxy Fatty Acid
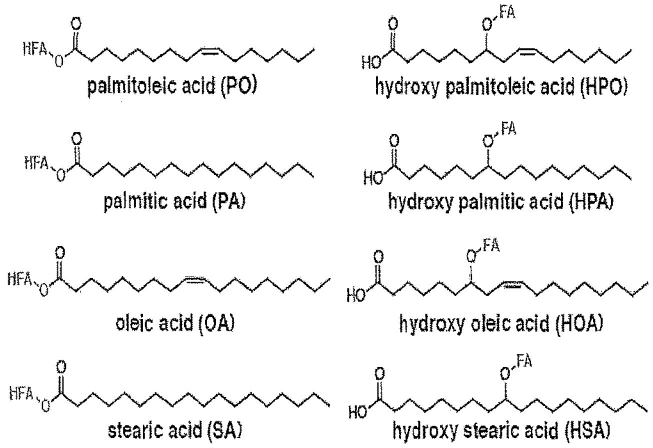
palmitoleic acid (PO) | hydroxy palmitoleic acid (HPO)
palmitic acid (PA) | hydroxy palmitic acid (HPA)
oleic acid (OA) | hydroxy oleic acid (HOA)
stearic acid (SA) | hydroxy stearic acid (HSA)
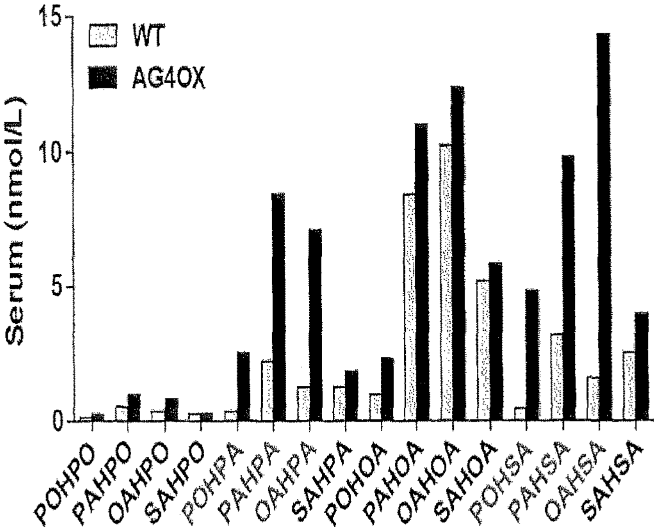
E
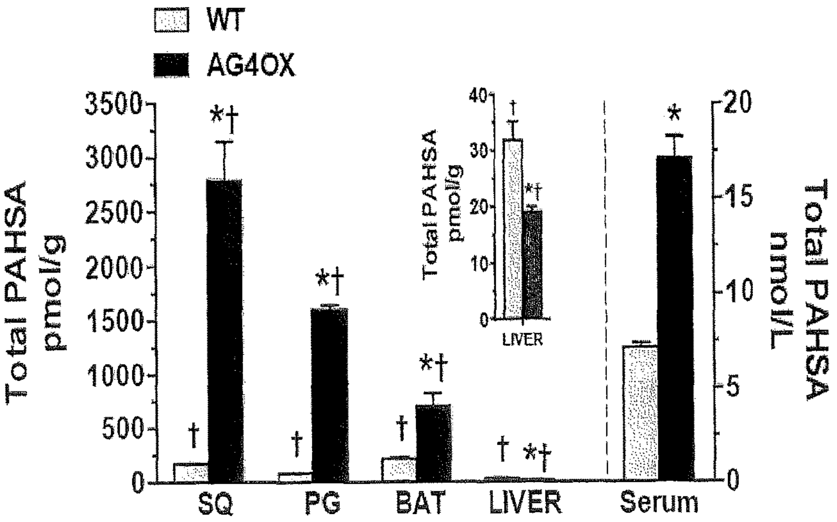
FIG. 49D-E

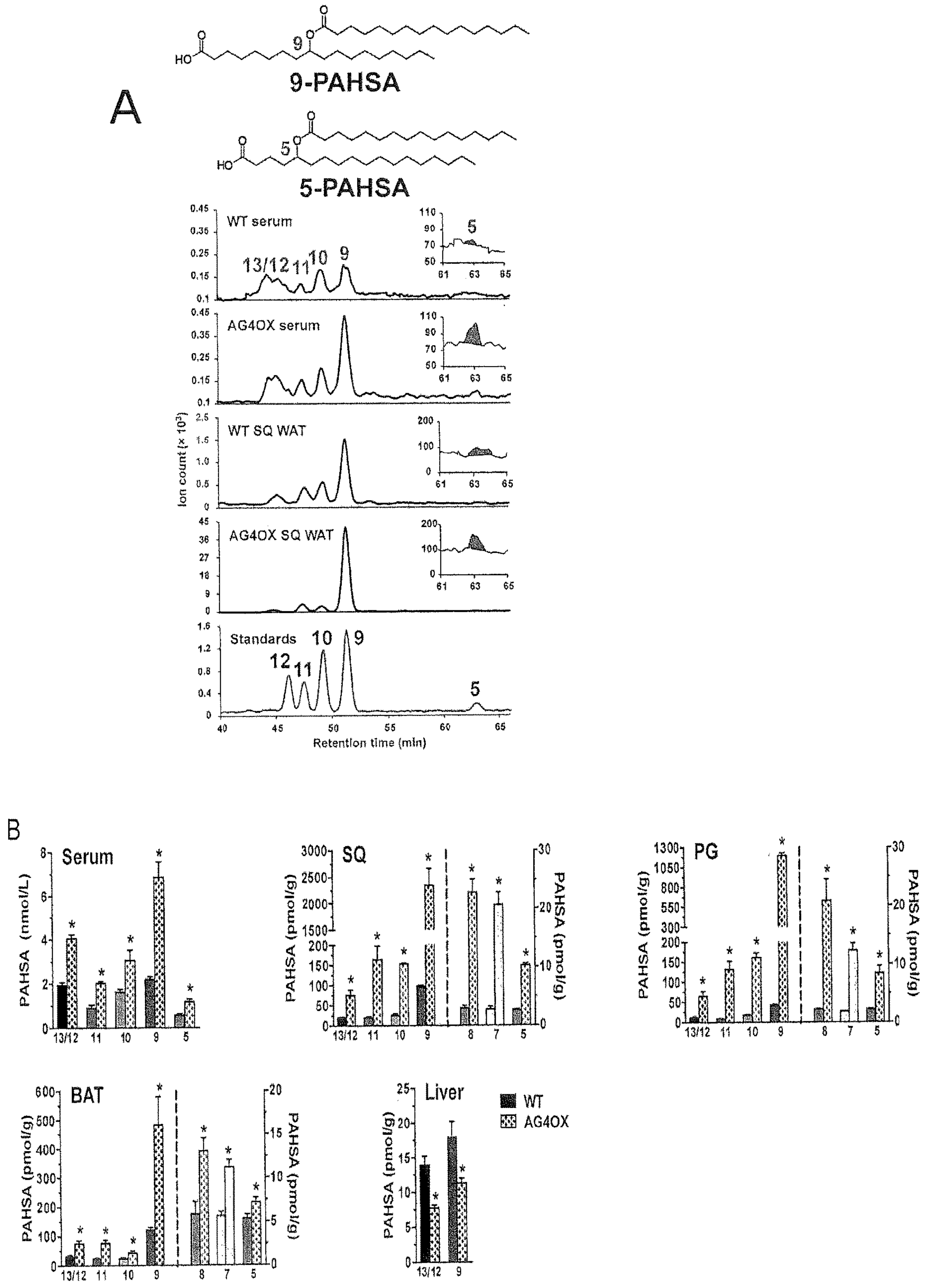
FIG. 50A-B

C
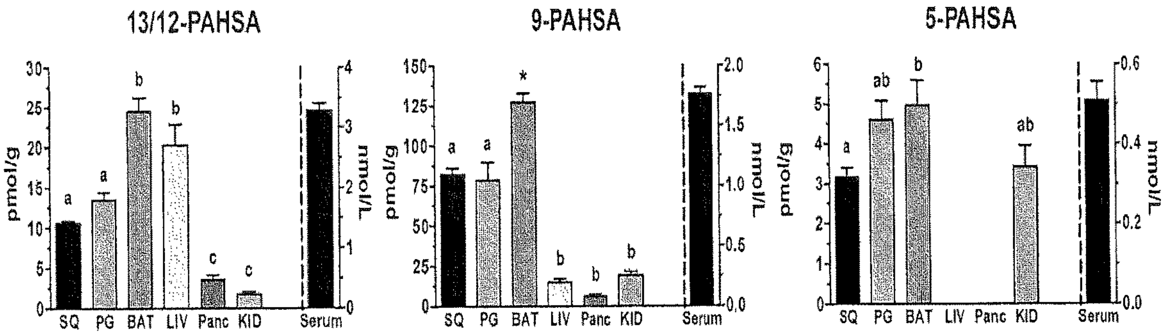
D
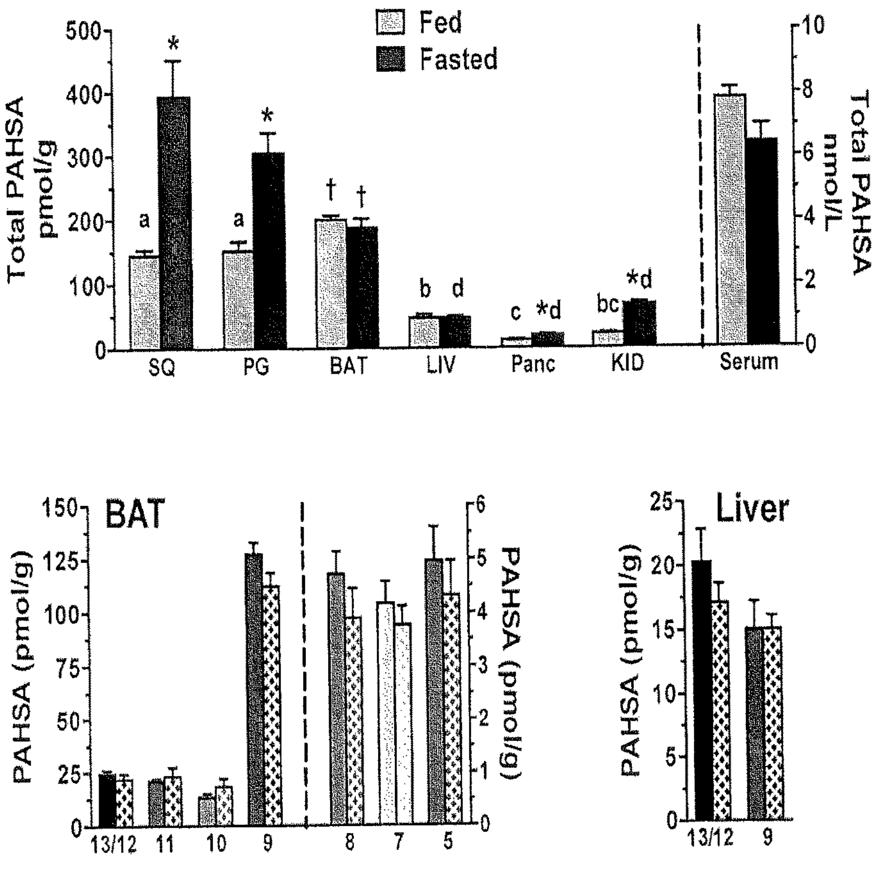
FIG. 50C-D

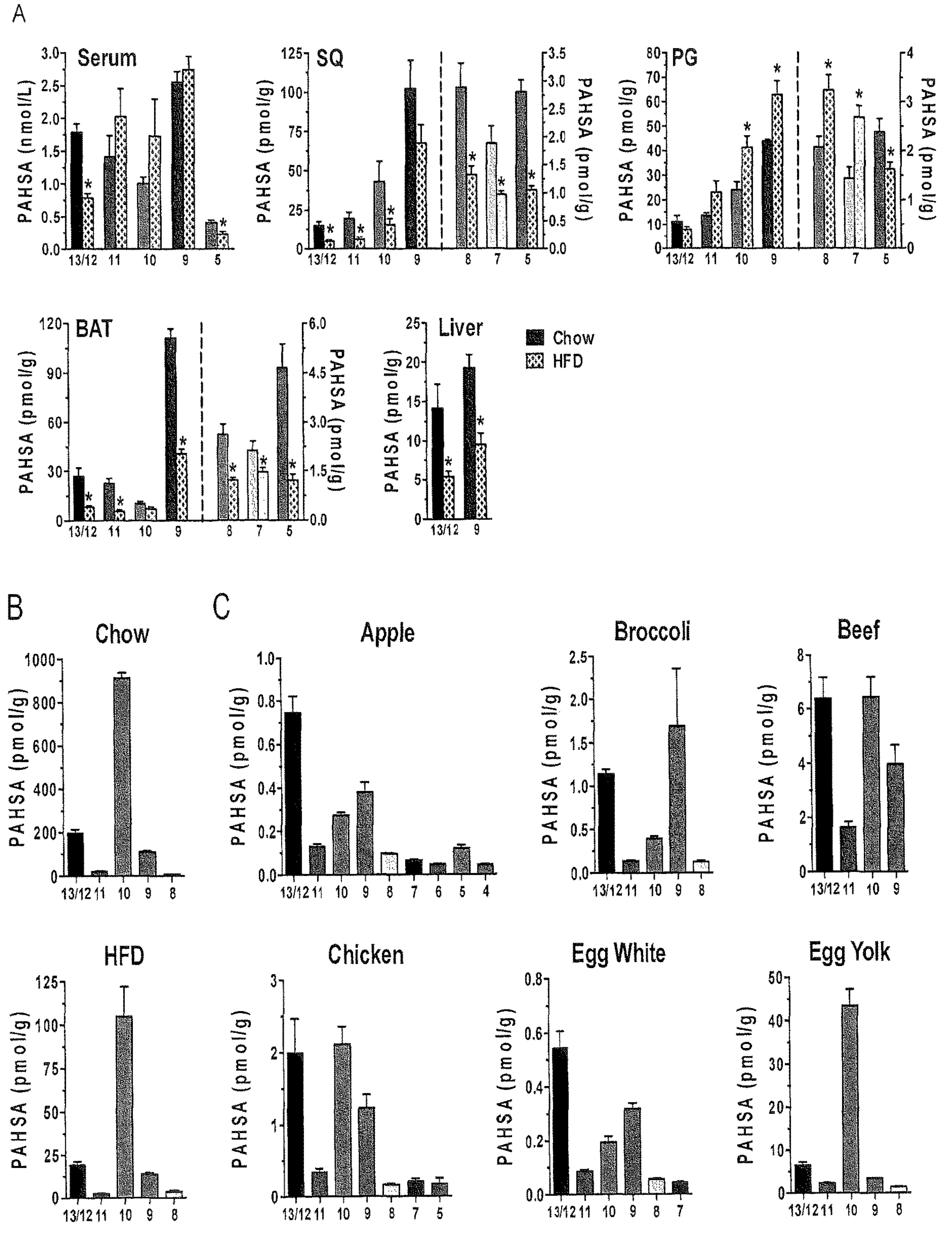
FIG. 51A-C

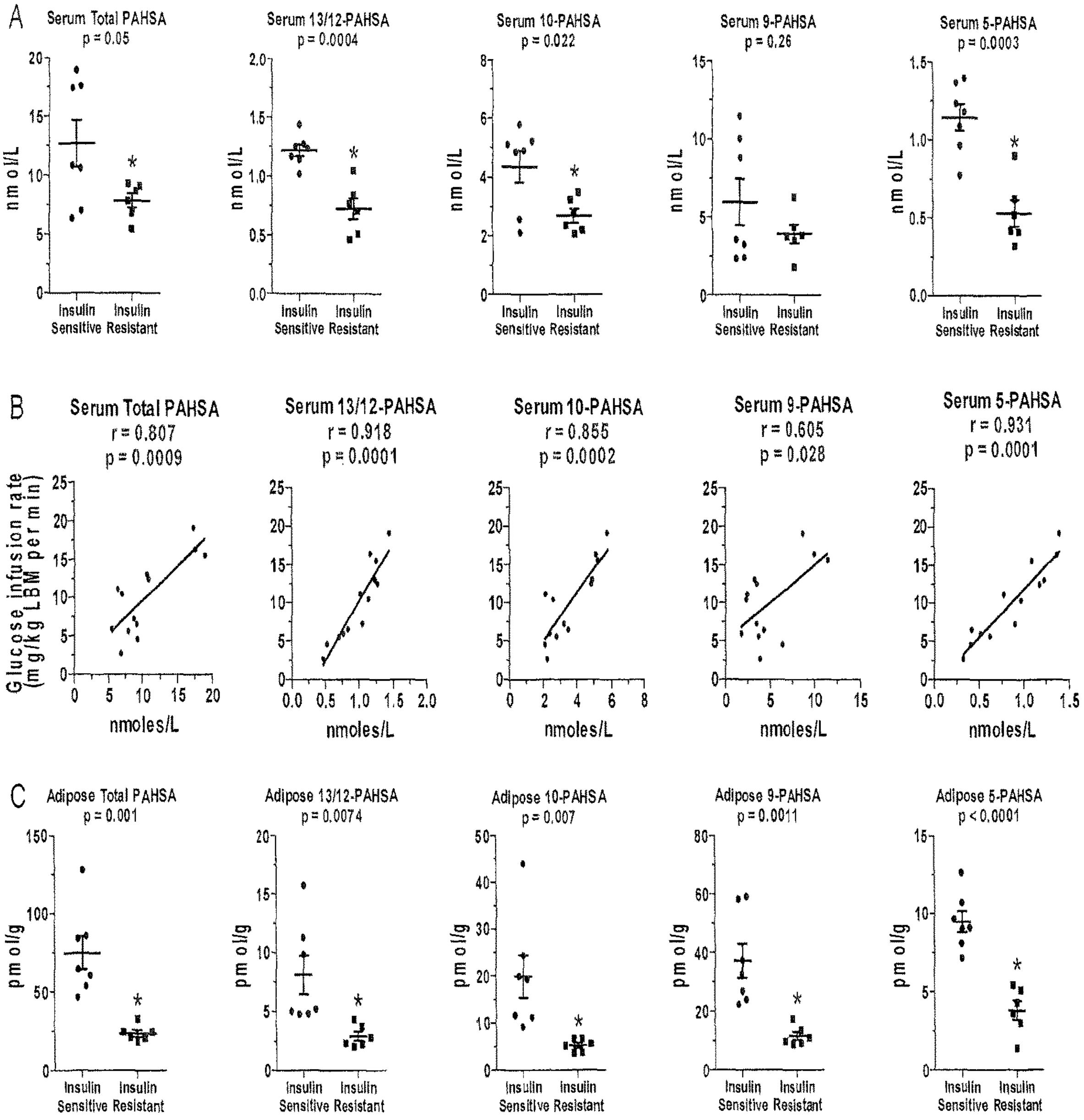
FIG. 52A-C

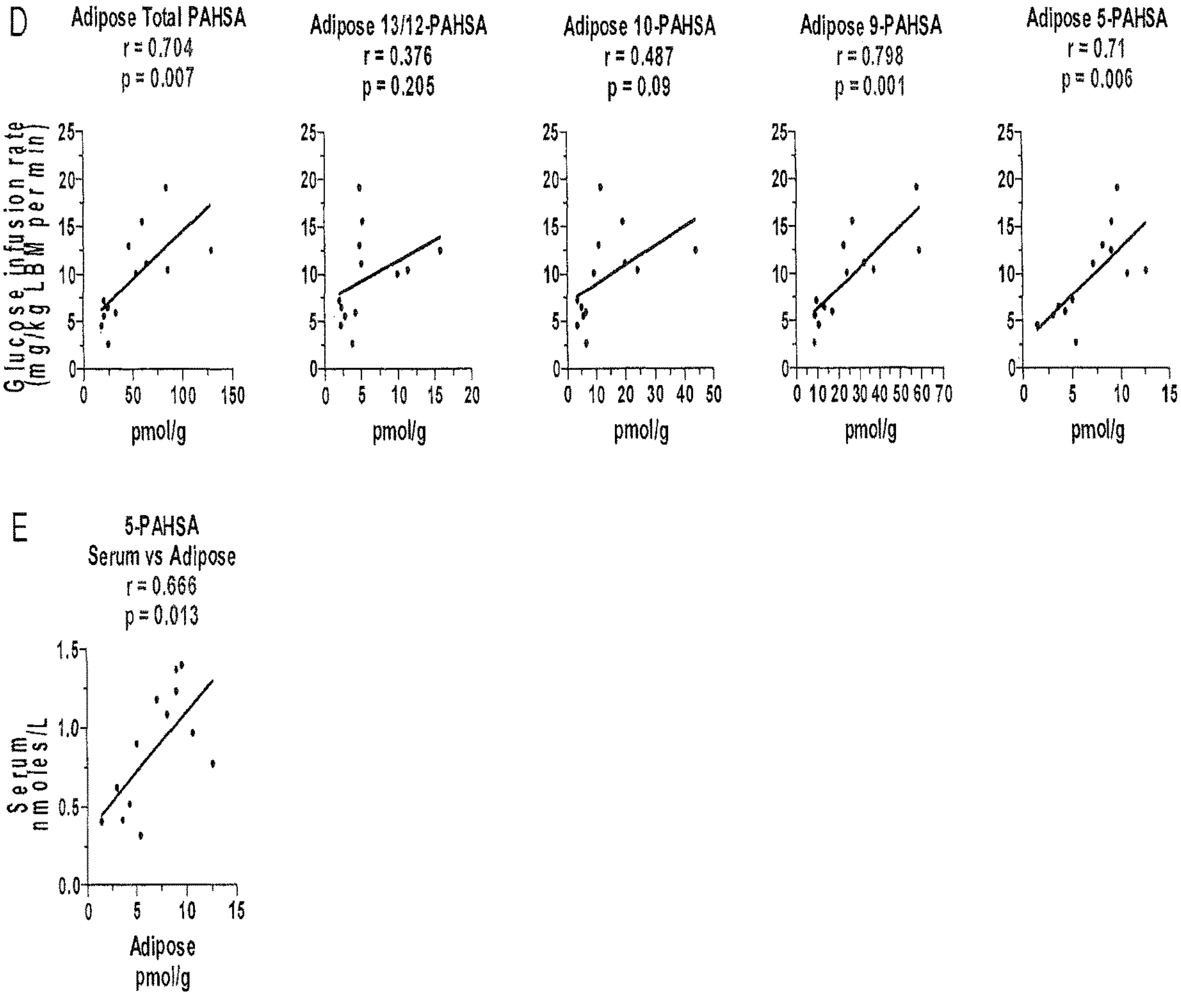
FIG. 52D-E

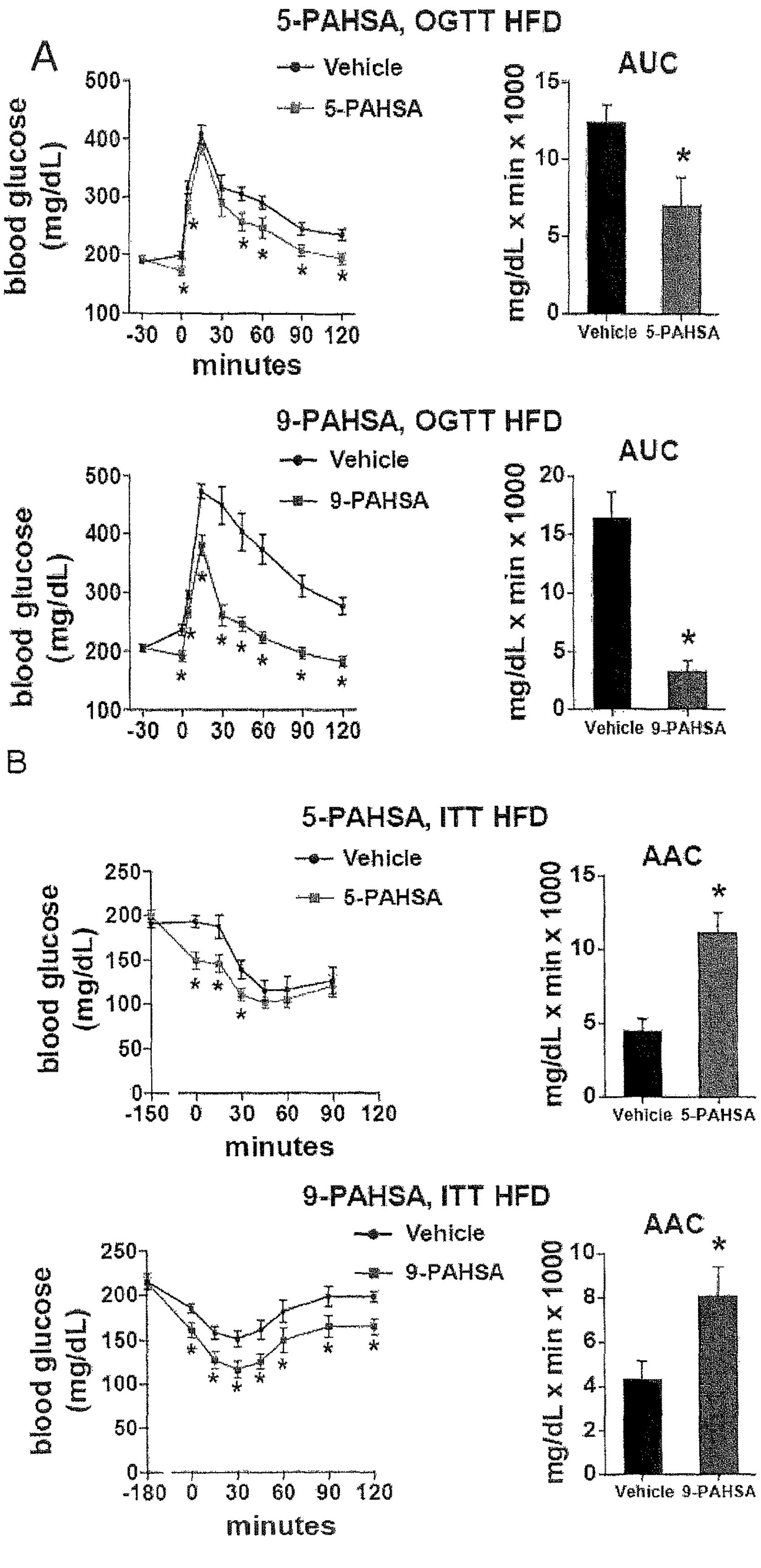
FIG. 53A-B

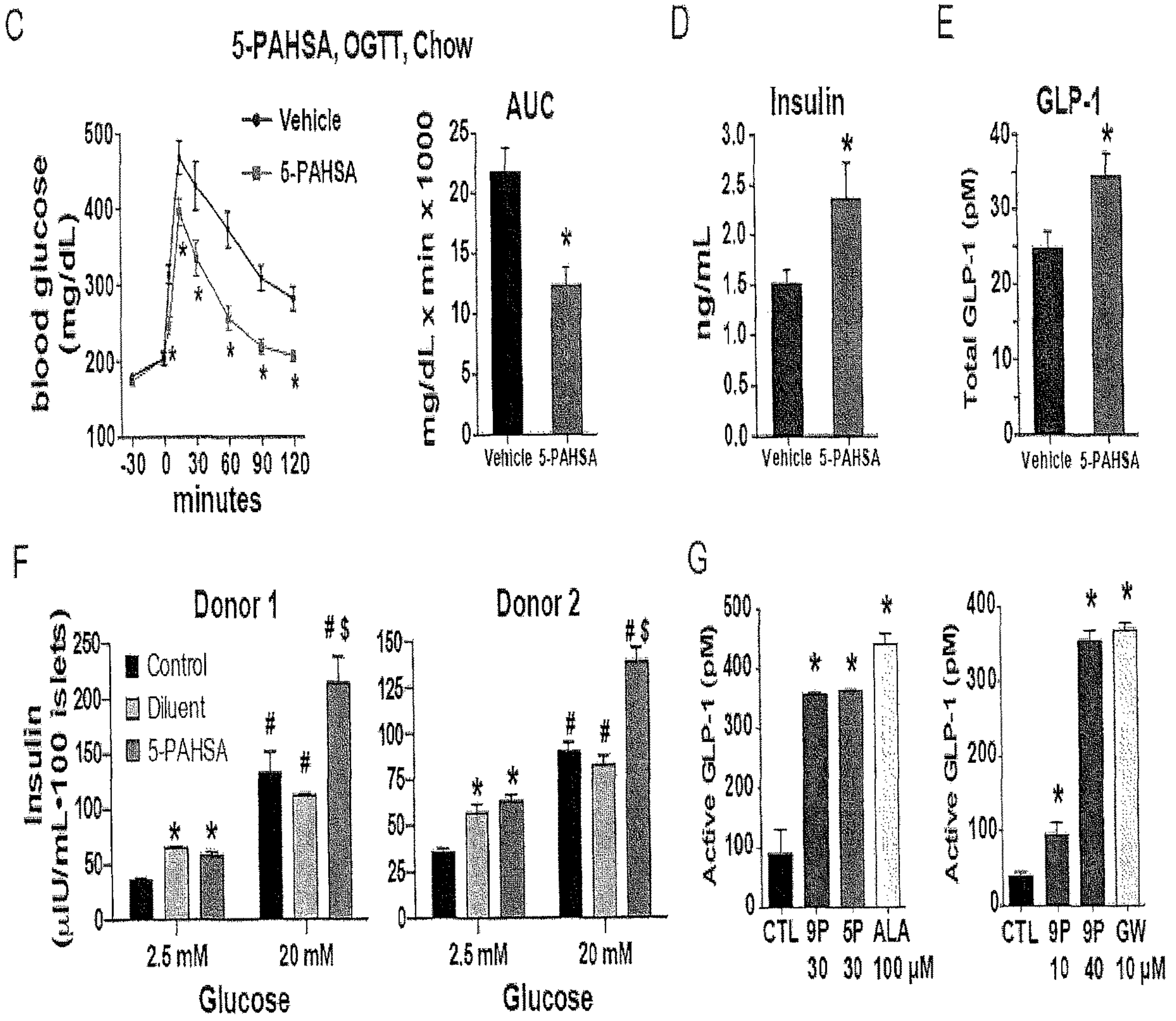
FIG. 53C-G

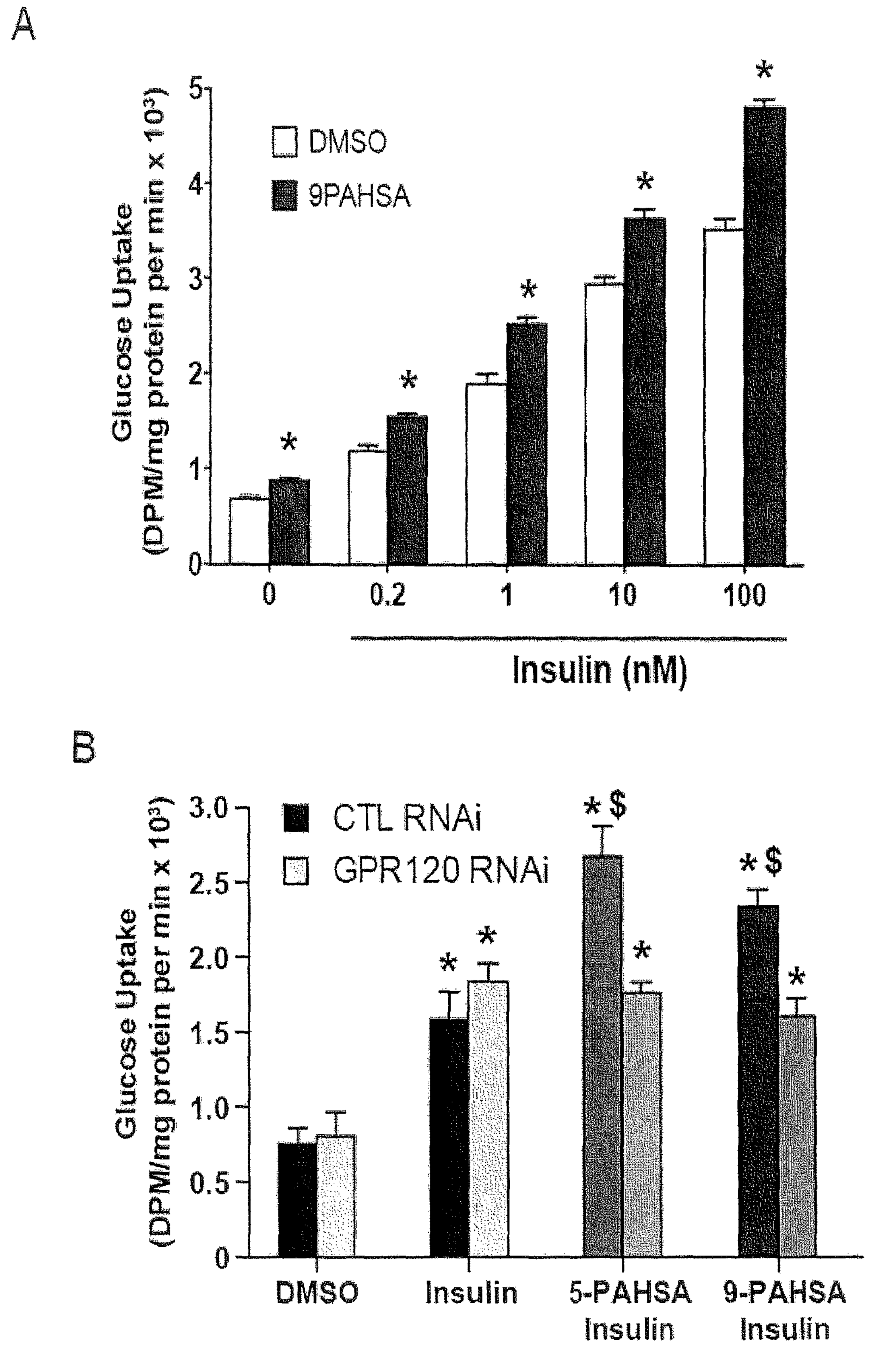
FIG. 54A-B

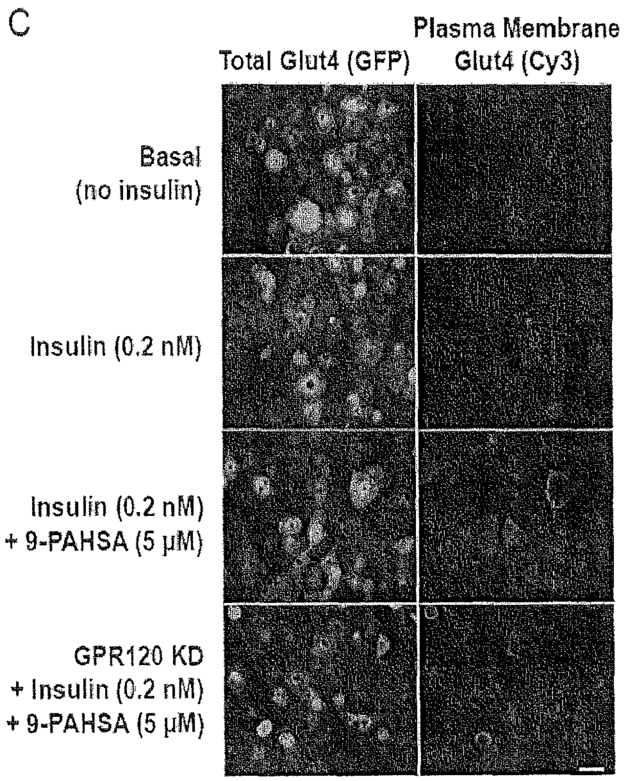
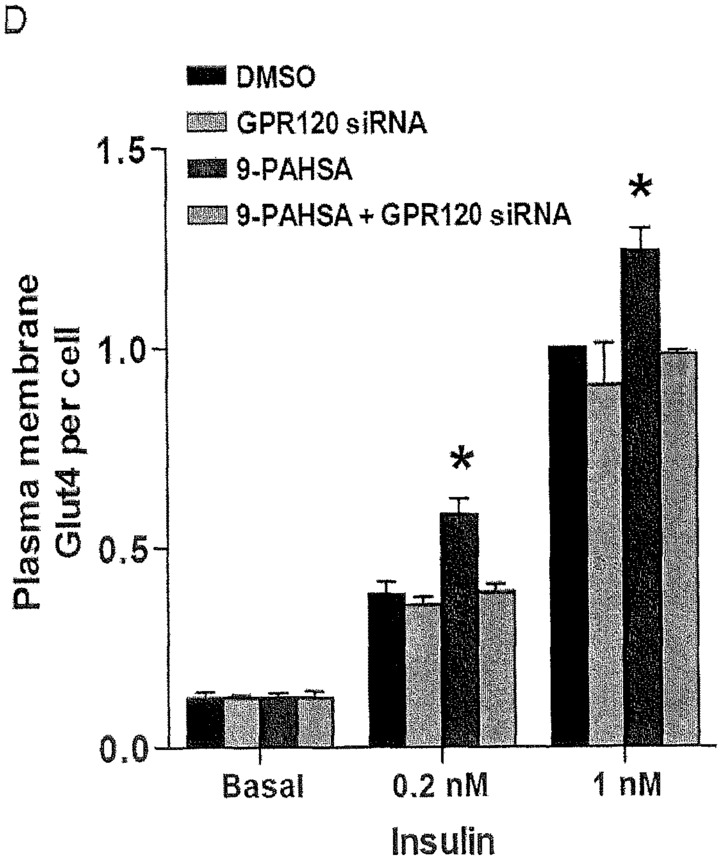
FIG. 54C-D

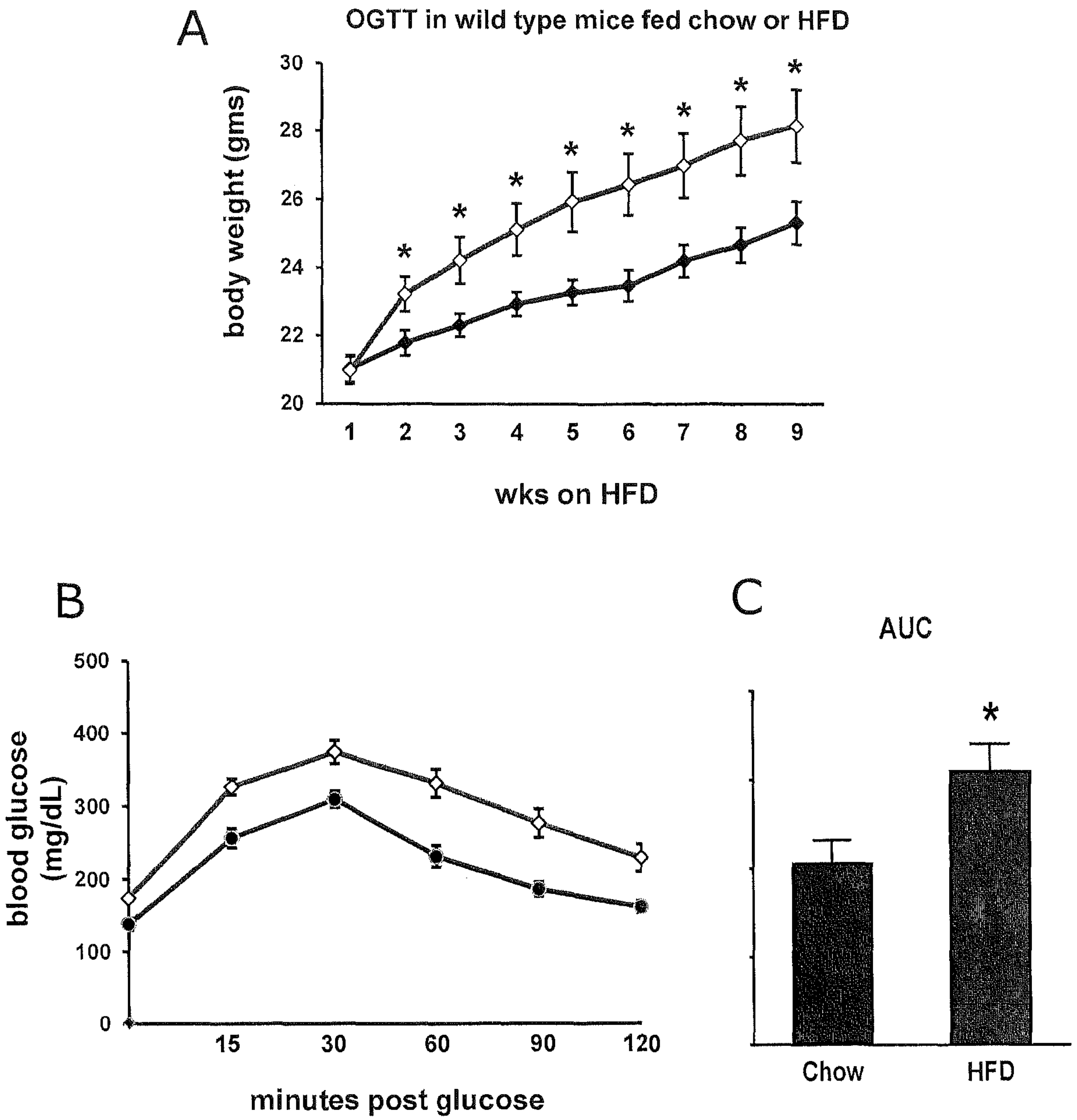
FIG. 55A-C

SEQUENCE LISTING

<160> NUMBER OF SEQ ID NOS: 12

<210> SEQ ID NO 1
<211> LENGTH: 25
<212> TYPE: RNA
<213> ORGANISM: Artifical Sequence
<220> FEATURE:
<223> OTHER INFORMATION: synthetic oligonucleotide

<400> SEQUENCE: 1
ggaguuaacu ucaaggaaag cccac 25

<210> SEQ ID NO 2
<211> LENGTH: 27
<212> TYPE: RNA
<213> ORGANISM: Artifical Sequence
<220> FEATURE:
<223> OTHER INFORMATION: synthetic oligonucleotide

<400> SEQUENCE: 2
gugggcuuuc cuugaaguua acucccu 27

<210> SEQ ID NO 3
<211> LENGTH: 25
<212> TYPE: DNA
<213> ORGANISM: Artifical Sequence
<220> FEATURE:
<223> OTHER INFORMATION: synthetic oligonucleotide

<400> SEQUENCE: 3
cccaaccgca uaggagaaau cucat 25

<210> SEQ ID NO 4
<211> LENGTH: 27
<212> TYPE: RNA
<213> ORGANISM: Artifical Sequence
<220> FEATURE:
<223> OTHER INFORMATION: synthetic oligonucleotide

<400> SEQUENCE: 4
augagauuuc uccuaugcgg uugggcc 27

<210> SEQ ID NO 5
<211> LENGTH: 25
<212> TYPE: DNA
<213> ORGANISM: Artifical Sequence
<220> FEATURE:
<223> OTHER INFORMATION: synthetic oligonucleotide

<400> SEQUENCE: 5
gcaaauuaag gaaugaucgc ucagt 25

<210> SEQ ID NO 6
<211> LENGTH: 27
<212> TYPE: RNA
<213> ORGANISM: Artifical Sequence
<220> FEATURE:
<223> OTHER INFORMATION: synthetic oligonucleotide

<400> SEQUENCE: 6
acugagcgau cauuccuuaa uuugcug 27

<210> SEQ ID NO 7
<211> LENGTH: 24
<212> TYPE: RNA
<213> ORGANISM: Artifical Sequence

```
<220> FEATURE:
<223> OTHER INFORMATION: synthetic oligonucleotide

<400> SEQUENCE: 7

cguuaaucgc guauaauacg cgua                                    24


<210> SEQ ID NO 8
<211> LENGTH: 27
<212> TYPE: RNA
<213> ORGANISM: Artifical  Sequence
<220> FEATURE:
<223> OTHER INFORMATION: synthetic oligonucleotide

<400> SEQUENCE: 8

auacgcguau uauacgcgau uaacgac                                 27


<210> SEQ ID NO 9
<211> LENGTH: 19
<212> TYPE: DNA
<213> ORGANISM: Artifical  Sequence
<220> FEATURE:
<223> OTHER INFORMATION: synthetic oligonucleotide

<400> SEQUENCE: 9

cttctgcgcg gatttgctc                                          19


<210> SEQ ID NO 10
<211> LENGTH: 22
<212> TYPE: DNA
<213> ORGANISM: Artifical  Sequence
<220> FEATURE:
<223> OTHER INFORMATION: synthetic oligonucleotide

<400> SEQUENCE: 10

ccgctcattg tcatcacgta ga                                      22


<210> SEQ ID NO 11
<211> LENGTH: 20
<212> TYPE: DNA
<213> ORGANISM: Artifical  Sequence
<220> FEATURE:
<223> OTHER INFORMATION: synthetic oligonucleotide

<400> SEQUENCE: 11

ccctatcact cctgccacac                                         20


<210> SEQ ID NO 12
<211> LENGTH: 22
<212> TYPE: DNA
<213> ORGANISM: Artifical  Sequence
<220> FEATURE:
<223> OTHER INFORMATION: synthetic oligonucleotide

<400> SEQUENCE: 12

acgaagtgca atggtcttta gc                                      22
```

LIPIDS THAT INCREASE INSULIN SENSITIVITY AND METHODS OF USING THE SAME

RELATED APPLICATION

This application is the U.S. National Stage of International Application No. PCT/US2014/029329, filed Mar. 14, 2014, which designates the U.S., published in English, and claims the benefit of U.S. Provisional Application No. 61/794,930, filed on Mar. 15, 2013 and claims the benefit of U.S. Provisional Application No. 61/794,609, filed on Mar. 15, 2013. The entire teachings of the above applications are incorporated herein by reference.

GOVERNMENT SUPPORT

This invention was made with government support under grants DK057521, DK046200 and DK043051 awarded by NIH. The government has certain rights in the invention.

INCORPORATION BY REFERENCE OF MATERIAL IN ASCII TEXT FILE

This application incorporates by reference the Sequence Listing contained in the following ASCII text file:

a) File name: 14402077003 SEQLISTING.txt; created Feb. 16, 2016, 3 KB in size.

BACKGROUND

The prevalence of obesity and type 2-diabetes is increasing worldwide and threatens to shorten lifespan. Impaired insulin action in peripheral tissues is a major pathogenic factor. Insulin stimulates glucose uptake in adipose tissue through the Glut4-glucose transporter and alterations in adipose-Glut4 expression or function regulate systemic insulin sensitivity. Downregulation of adipose tissue-Glut4 occurs early in diabetes development. Complications from obesity and type-2 diabetes include vascular disease, which detracts from quality of life further and increases mortality. Other disorders, such as polycystic ovarian syndrome and some inflammatory disorders have higher prevalence in individuals with diabetes related disorders—and the signaling pathways driving certain diabetes related disorders cross-talk with pathways that regulate inflammation. In addition, cancer, a prevalent and devastating disorder can be characterized by changes in metabolic flux, e.g., via the so-called Warburg effect, by which cancer cells substantially upregulate the level of glycolysis. Many cancer cells also have increased de novo lipogenesis. In view of the prevalence of these disorders and their relation to changes in metabolism, a need exists for methods of detecting and monitoring disease states and/or treatment programs in subjects with diabetes-related disorders, obesity, polycystic ovarian syndrome (PCOS), gestational diabetes, inflammatory disorders, vascular disease, or cancer, as well as tools and method of identifying agents that modulate key metabolic pathways.

SUMMARY OF THE INVENTION

The invention provides, inter alia, methods of monitoring disease states and/or treatment responses for a variety of metabolic disorders, such as obesity and type 2 diabetes (and diabetes-related disorders) as well as common complications such as vascular disease, polycystic ovarian syndrome, gestational diabetes, inflammatory disorders and other disorders associated with changes in metabolic flux, such as cancer. The invention is based, at least in part, on Applicants' unexpected discovery of a novel class of lipids upregulated in AG4OX mice—termed fatty acyl fatty hydroxy acids, referred to herein as "FAHFAs"—as well as 1) human clinical data that indicates a strong correlation between levels of these lipids and insulin sensitivity and/or obesity and 2) the ability of these lipids to inhibit dendritic cell activation.

Accordingly, in one aspect, the invention provides an isolated fatty acyl hydroxy fatty acid (FAHFA) of formula (I):

(I)

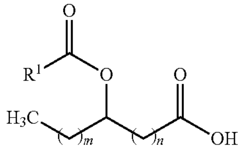

Wherein: m is an integer from 0 to 21;

n is an integer from 0 to 21;

the sum of m and n is an integer from 11 to 21;

$R^1$ is an alkyl group;

or a salt thereof.

In particular embodiments, $R^1$ of formula (I) is a ($C_{15}$-$C_{17}$) alkyl group. In other particular embodiments, n is 7; and $R^1$ is a $C_{15}H_{31}$ in of formula (I). In other particular embodiments of formula (I) m is 12; n is 3; and $R^1$ is a $C_{15}H_{31}$. In certain embodiments, any of the forgoing particular embodiments are detectably labeled. For example, the FAHFA can be isotopically labeled and/or ester- or amide-bound to a detectable moiety, such as biotin, streptavidin, GST, a fluorous affinity tag, an alkyne suitable for click chemistry, an epitope tag such as FLAG, 6× His, or another affinity tag. In certain embodiments, the invention also provides a FAHFA incorporated into structures such as phospholipids, glycerophospholipids, carbohydrates, polypeptides and proteins, di- and triglycerides, and conjugates to metabolic cofactors such as CoA or acyl carnitine. In further aspects, the invention provides compositions and formulations comprising any of the foregoing.

In another aspect, the invention provides methods of assessing the disease state and/or treatment response of a mammalian subject for a disease or disorder selected from obesity, type 2 diabetes (T2D), impaired glucose tolerance, maturity onset diabetes of the young (MODY), impaired fasting glucose, metabolic syndrome, insulin resistance, polycystic ovarian syndrome, gestational diabetes, cardiovascular disease, inflammatory disorders, and cancer and the like by determining the level of one or more FAHFAs, or a precursor or derivative thereof, in a biological sample from the subject (such as an isolated sample of, e.g., serum or plasma or a biopsy), where the level of the one or more FAHFAs indicates the subject's disease state and/or treatment response for the disease or disorder. Suitable biological samples include a blood fraction, bile salt, pancreas secretions, or a tissue biopsy. In more particular embodiments, the blood fraction is plasma or serum. In other particular embodiments, the tissue biopsy comprises adipose tissue. In still other particular embodiments, the tissue biopsy comprises pancreas, liver, kidney, or tumor tissue. In any of these methods, the FAHFA, or precursor or derivative thereof, is detected by any suitable means, including methods comprising MS/MS or an immunoassay.

Exemplary inflammatory disorders include sepsis, rheumatoid arthritis (RA), ulcerative colitis, inflammatory bowel disease, Crohn's disease, systemic lupus erythematosus, celiac disease, uveitis, pancreatitis, adult respiratory distress syndrome, asthma, multiple sclerosis, graft-versus host disease, atopic dermatitis, ankylosing spondylitis, and the like. MODY can be one or more of MODY 1, 2, 3, 4, 5, 6, 7, 8, 9, 10, or 11 and, in some embodiments, the subject is determined to be heterozygous or homozygous for a germline mutation in one or more genes selected from HNF4A, GCK, HNF1A, PDX1, TCF2, NEUROD1, KLF11, CEL, PAX4, INS, or BLK.

In another aspect, the invention provides methods of decreasing pro-inflammatory signaling or increasing: glucose uptake, glucose tolerance, insulin secretion, or insulin sensitivity in a cell, by contacting the cell with an agent that increases the level of one or more FAHFAs. In a related aspect, the invention also provides methods of decreasing pro-inflammatory signaling or increasing: glucose uptake, glucose tolerance, insulin secretion, or insulin sensitivity in a mammalian subject in need thereof, by administering to the subject a therapeutically effective amount of an agent that increases the level of one or more FAHFAs. In either of these related aspects, the agent that increases the level of one or more FAHFAs can be an exogenous FAHFA, or a substrate of carboxyl ester lipase (CEL), an inhibitor of CEL, a CHREBP expression product, or a PPAR agonist, such as an agonist of one or more of PPAR α, PPAR β, or PPAR γ. In particular in vivo embodiments, the subject has type 2 diabetes (T2D). In some embodiments, the biologic effect of the FAHFA is to block dendritic cell maturation, activation, or proliferation; macrophage maturation, activation, or proliferation; T lymphocyte maturation, activation, or proliferation; and pro-inflammatory signaling, as well as combinations thereof. In more particular embodiments, the dendritic cell maturation, activation or proliferation comprises an increase in CD40+, CD80+, CD86+, MHCII+ cells, or combinations thereof. In still more particular embodiments, the increased number of CD40+, CD80+, CD86+, or MHCII+ cells are also CD11c+. In other particular embodiments, the pro-inflammatory signaling is release of a proinflammatory cytokine selected from TNF-α, IL-1β, IL-12p70, or combinations thereof.

In another aspect, the invention provides methods of identifying an agent that modulates the level of one or more FAHFAs. These methods include the steps of contacting a candidate agent with a cell and measuring the level of one or more FAHFAs, where a change in the level of one or more FAHFAs in the cell, relative a control cell not contacted with the agent, indicates that the agent modulates the level of one or more FAHFAs. In particular embodiments, the agent increases the levels of one or more FAHFAs in the cell. In other particular embodiments, the agent decreases the levels of one or more FAHFAs in the cell. In other particular embodiments, the agent modulates the level of a FAHFA synthase. In still other particular embodiments, the agent modulates the level of a FAHFA esterase.

In particular embodiments, the cell used in these methods is an isolated, cultured animal cell, such as a macrophage (such as a RAW cell), an islet cell (such as Ins1 cell line), or a hepatic cell (such as a HepG2 cell). In more particular embodiments, the cell is cultured in the presence of low glucose. In other particular embodiments, the cell is cultured in the presence of a modulator of PPAR α, γ, or δ.

In other particular embodiments, the cell is located in a non-human animal—i.e. the method is performed, at least in part, in vivo. In more particular embodiments, the non-human animal is a mammal and in still more particular embodiments, is murine, e.g., an AG4OX mouse, an AG4KO mouse, a ChREBPKO mouse, or a ChREBPOX mouse, and combinations thereof, et cetera.

In another aspect, the invention provides a detectable biotinylated amino-FAHFA of formula (II):

(II)

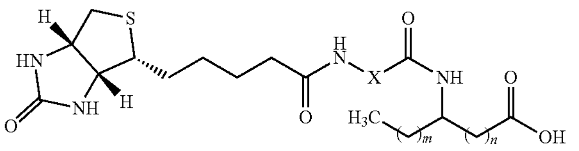

Wherein: m is an integer from 0 to 21;

n is an integer from 0 to 21;

the sum of m and n is an integer from 11 to 21;

X is selected from $(OCH_2CH_2)_p$ or $(CH_2)_p$, wherein p is an integer from 2 to 20;

or a salt thereof.

In another aspect, the invention provides methods of identifying FAHFA-binding molecules, such as FAHFA-binding proteins. In some embodiments, detectably labeled FAHFAs are used. In particular embodiments, one or more detectably labeled FAHFAs are contacted with whole cells, cell extracts, or synthetic biomixtures, including, for example isolated proteins. After a suitable amount of time to allow binding of the one or more FAHFAs to other molecules in the mixture, a complex of the detectably labeled one or more FAHFAs and any binding partners is detected—optionally including isolation of the complex. Molecules bound to one or more FAHFAs are then identified by any suitable means, including MS/MS (e.g., proteolyic digestion of FAHFA-bound proteins, and detection of peptides by MS/MS). In other embodiments, FAHFAs are detected in co-IP or other pull-down assay; e.g., either the binding partner is isolated by suitable means and one or more FAHFAs are detected by any suitable means or vice versa. One exemplary methodology of identifying FAHFA binding partners, using SILAC (stable isotope labeling by/with amino acids in cell culture), is shown in FIG. 34.

In another aspect, the invention provides methods of identifying FAHFA-binding molecules, such as FAHFA-binding proteins. In some embodiments, detectably labeled FAHFAs are used. In particular embodiments, one or more detectably labeled FAHFAs are contacted with whole cells, cell extracts, tissues, serum or plasma, or synthetic biomixtures, including, for example isolated proteins. After a suitable amount of time to allow binding of the one or more FAHFAs to other molecules in the mixture, a complex of the detectably labeled one or more FAHFAs and any binding partners is detected—optionally including isolation of the complex. Molecules bound to one or more FAHFAs are then identified by any suitable means, including MS/MS (e.g., proteolyic digestion of FAHFA-bound proteins, and detection of peptides by MS/MS). In other embodiments, FAHFAs are detected in co-IP or other pull-down assay; e.g., either the binding partner is isolated by suitable means and one or more FAHFAs are detected by any suitable means or vice versa. One exemplary methodology of identifying FAHFA binding partners, using SILAC (stable isotope labeling by/with amino acids in cell culture), is shown in FIG. 34.

In yet another aspect, the invention provides methods of identifying a modulator of FAHFA-mediated signaling and/or FAHFA-mediated biological effects. The methods include forming a mixture with an isolated mammalian cell that expresses a G-protein coupled receptor (GCPR), one or more FAHFAs, and a test compound and monitoring the FAHFA-mediated signaling. A change in the FAHFA-mediated signaling indicates that the test compound is a modulator of FAHFA-mediated signaling. In certain embodiments, the GCPR is GPR120 (human GeneID No. 338557, see also OMIM 609044) or GPR40 (human GeneID No. 2864; OMIM 603820). In some embodiments, the one or more FAHFAs comprise 9-PAHSA, 5-PAHSA, 9-OAHSA, or a combination thereof. In other embodiments, the FAHFA-mediated biologic effect is selected from decreasing pro-inflammatory signaling, stimulating insulin secretion, stimulating glucagon like peptide-1 (GLP1; see human GeneID No. 2641 and OMIM 138030) or other incretin secretion, stimulating calcium flux into the cell or from intracellular organelles into the cytoplasm, G-protein activation, and combinations thereof. In more particular embodiments, the FAHFA-mediated biological effect is stimulating insulin secretion and, in more particular embodiments, the isolated mammalian cell is a pancreatic islet cell. In other particular embodiments the FAHFA-mediated biological effect is stimulating GLP1 secretion and, in more particular embodiments, the cell is an enteroendocrine cell from the intestine of a mammal (such as STC-1 cells). In any of these related embodiments, the mammalian cell may be a human cell.

In another aspect, the invention provides an isolated fatty acyl hydroxy fatty acids (FAHFAs) and derivatives thereof, having the structure of Formula (III):

(III)

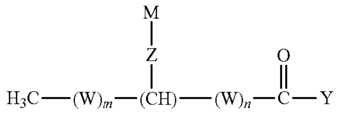

or a salt thereof, wherein:

m is an integer from 0 to 21;

n is an integer from 0 to 21;

the sum of m and n is an integer from 11 to 21;

W, for each occurrence, is independently $(CR^1R^2)$ or $(C(R^3)=C(R^4))$;

Z is —NH(CO)—, —O—, —O(CO)—, —S—, —NH—, —NO—, —O(CO)O—, —O(CO)NH—, —NH(CO)O—, $—SO_2—$, $—OP(O)(OR^{11})O—$, —Se—, —SeO—, $—N(R^{11})—$, or $—O(CO)N(R^{11})—$;

Y is H, OH, $OR^5$, $NHR^6$, $N(R^7)_2$, $SR^8$, or halo;

$R^1$, $R^2$, $R^3$ and $R^4$ for each occurrence, are independently selected from H, $(C_6-C_{12})$aryl, $(C_5-C_{12})$heteroaryl, $—(CO)(C_1-C_6)$alkyl, $(C_1-C_{12})$alkyl, $(C_1-C_{12})$alkoxy, or hydroxyl;

M is selected from $(CR^9R^{10})_{11-23}CH_3$, $(C_6-C_{12})$aryl, $(C_5-C_{12})$heteroaryl, or $(C_{12}-C_{24})$alkenyl, wherein each $(C_6-C_{12})$aryl, $(C_5-C_{12})$heteroaryl, and $(C_{12}-C_{24})$alkenyl is optionally and independently substituted at any one or more substitutable positions by $(C_1-C_{12})$alkyl, $(C_1-C_{12})$alkoxy, hydroxyl, $—NH_2$, $—N((C_1-C_{12})alkyl)_2$, or $—S—(C_1-C_{12})$alkyl;

$R^5$, $R^6$, $R^7$, and $R^8$ are each $(C_1-C_{12})$alkyl, $(C_6-C_{12})$aryl, $(C_5-C_{12})$heteroaryl, or $(C_{12}-C_{24})$alkenyl;

$R^9$ and $R^{10}$, for each occurrence, are H, $(C_1-C_{12})$alkyl, $(C_1-C_{12})$alkoxy, hydroxyl, $—NH_2$, $—N[(C_1-C_{12})alkyl]_2$, or $—S(C_1-C_{12})$alkyl;

provided that:

when any one of $R^1$ or $R^2$ is hydroxyl or $(C_1-C_{12})$alkoxy, then not all $R^9$ and $R^{10}$ are H;

when any one of $R^9$ or $R^{10}$ is hydroxyl or $(C_1-C_{12})$alkoxy, then not all $R^1$ and are H; and $(C_{12}-C_{24})$alkenyl is not $(C_{17})$alkenyl or $(C_{19})$alkenyl.

In particular embodiments, $R^1$ and $R^2$ of Formula (I), for each occurrence, are independently selected from H, $(C_6-C_{12})$aryl, or $(C_1-C_{12})$alkyl; Z is —NH(CO)—, —O, —O(CO)—, —O(CO)O—, —O(CO)NH—, or —NH(CO)O—; Y is OH or $OR^5$; and M is $(CH_2)_{11-23}CH_3$.

In other particular embodiments, the compound of Formula (I) has one of the following structures, or a salt thereof:

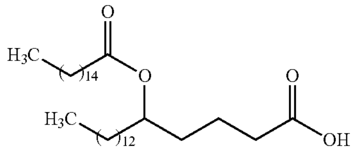

or

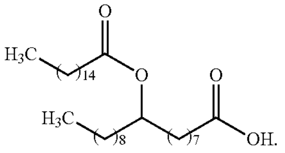

In still other particular embodiments, the compound of Formula (I) is not a compound of one of the following structures:

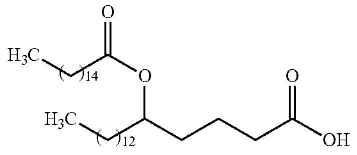

or

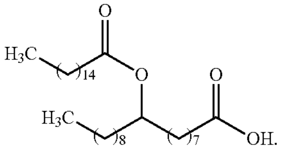

In certain embodiments, any of the forgoing particular embodiments are detectably labeled. For example, the FAHFA derivative can be isotopically labeled and/or ester- or amide-bound to a detectable moiety, such as biotin, streptavidin, GST, a fluorous affinity tag, an alkyne suitable for click chemistry, an epitope tag such as FLAG, 6× His, or another affinity tag. In certain embodiments, the invention also provides a FAHFA derivative incorporated into structures such as phospholipids, glycerophospholipids, carbohydrates, polypeptides and proteins, di- and triglycerides, and conjugates to metabolic cofactors such as CoA or acyl carnitine. In further aspects, the invention provides compositions and formulations comprising any of the foregoing.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 14 shows two exemplary biotinylated FAHFAs, Biotin-FAHFA-2 (BF-2) and Biotin-FAHFA-3 (BF-3).

FIG. 15 shows that adipose tissue ChREBP gene expression in obese humans correlates highly with systemic insulin sensitivity.

See the methodology of Norseen et al. *Mol Cell Biol.* 32(10):2010-9 (Epub 2012), which is incorporated by reference in its entirety, for additional description of these subjects.

Figures 18, 19:
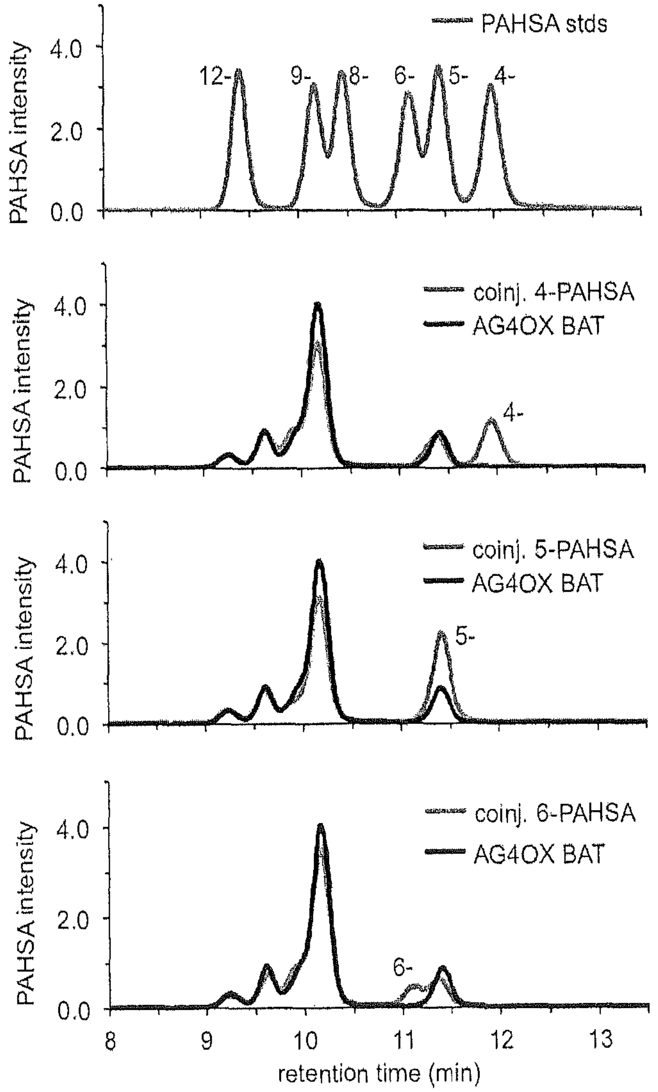
FIG. 18 is a table that shows baseline characteristics of human subjects undergoing a euglycemic-hyperinsulinemic clamp study, a test of insulin sensitivity. Serum samples were from the Lundberg Laboratory for Diabetes Research in Gothenburg, Sweden. Serum samples used in this analysis were obtained from individuals prior to the study. Percent glycosylated hemoglobin (HbA1c) was measured to assess the subject's average recent blood glucose levels (ref. range=4.0-5.9%) and to confirm the absence of frank diabetes (≥6.0%). Body mass index is calculated by dividing the subject's total mass in kilograms by the square of the height in meters. The glucose infusion rate reflects the steady-state rate of glucose infusion, normalized to lean body mass or to body weight, that is required to maintain euglycemia over a period between 60-180 minutes during which insulin is infused at a fixed rate (240 pmol/$m^2$/min).

FIG. 19 shows the resolution of positional isomers of PAHSA via a high-resolution chromatographic method. Coelution studies with 4-, 5- or 6-PAHSA synthetic standards showed that the later eluting peak in AG4OX brown adipose tissue was 5-PAHSA, and not 4- or 6-PAHSA.

Figure 20:
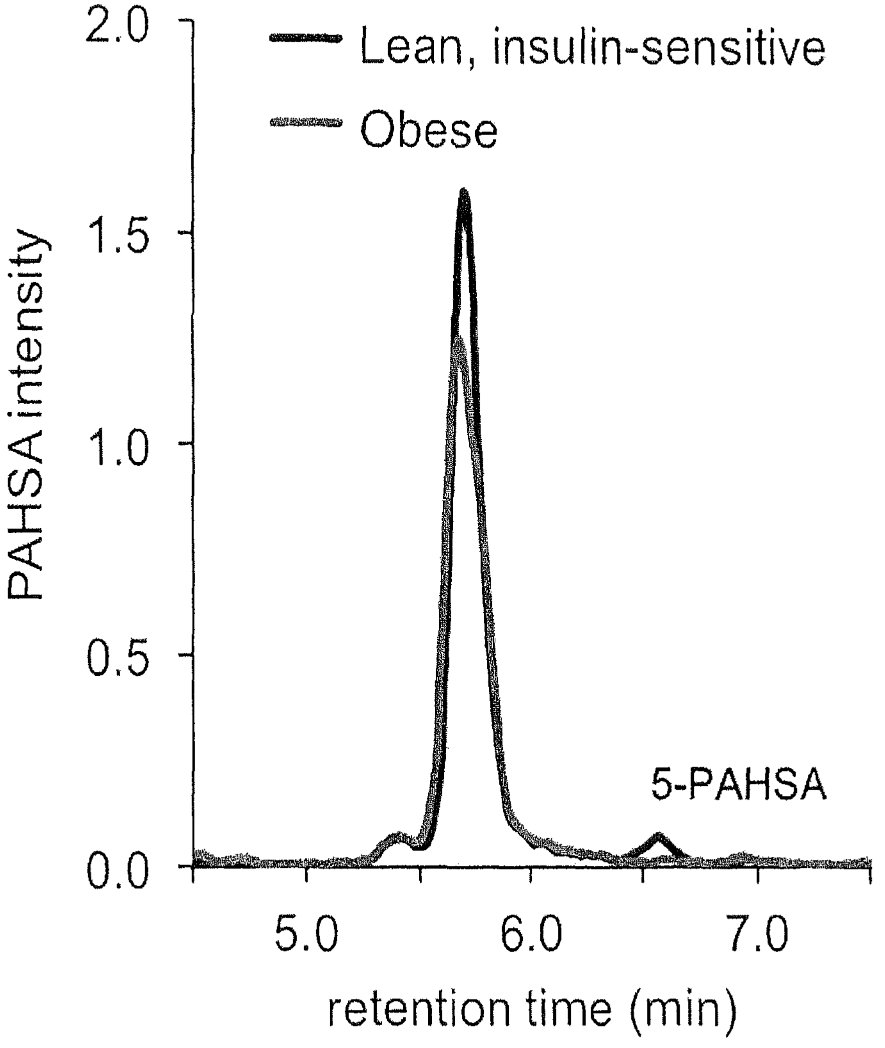

FIG. 20 shows a representative LC-MS trace of 5-PAHSA in serum from fasted human subjects. The lean insulin-sensitive subject had a body mass index (BMI) of 24.0 kg/$m^2$ and a glucose infusion rate normalized to lean body mass (GIR/LBM) of 23.6 mg/min/kg. The obese insulin-resistant subjected had a BMI of 31.2 kg/$m^2$ and a GIR/LBM of 8.6 mg/min/kg. Extracted serum samples were analyzed on an isocratic LC-MS method in MRM mode.

Figure 21:
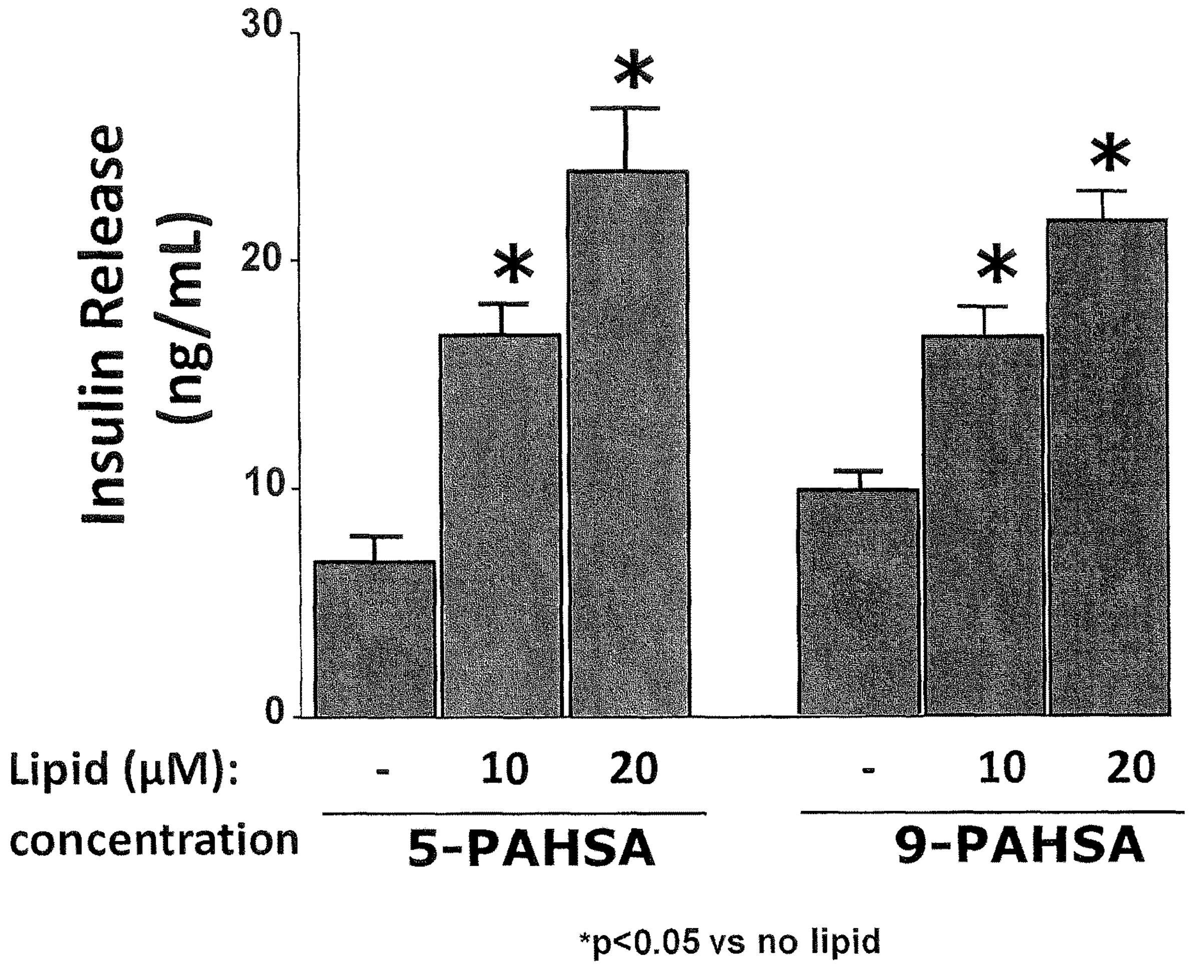
Figure 22:
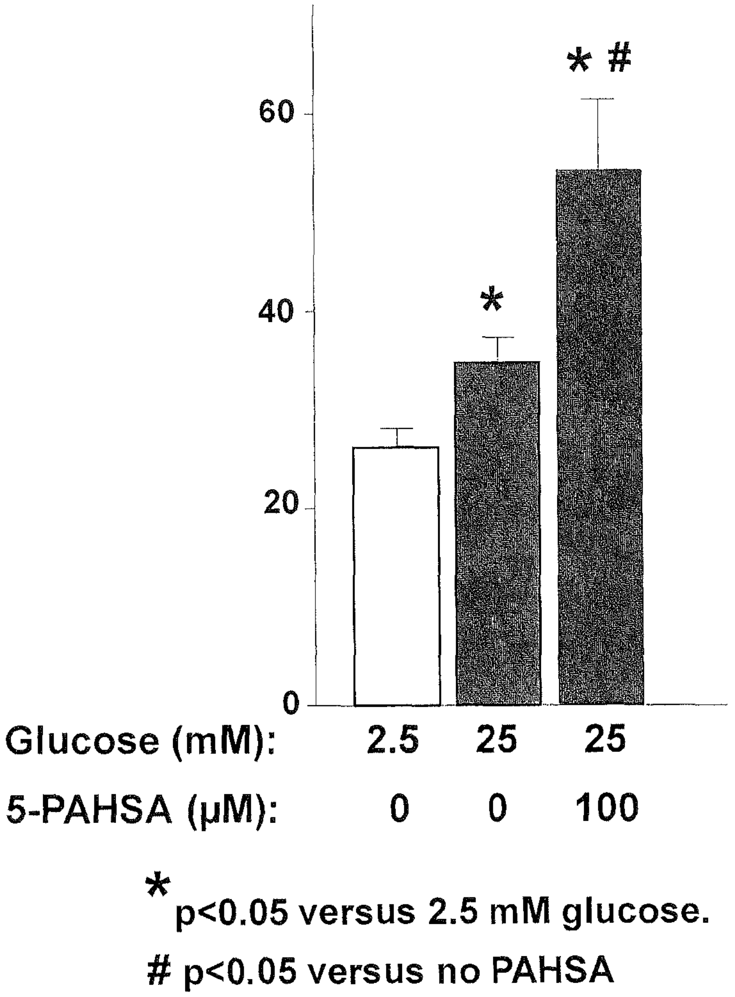

FIGS. 21 and 22 are bar graphs that illustrate the effects of FAHFAs on insulin release from islet cells. FIG. 21 shows that 5- and 9-PAHSA potentiate insulin secretion in Ins1 cells with 25 mM glucose in the media. FIG. 22 shows that 5-PAHSA potentiates glucose-stimulated insulin secretion in isolated rat islets with 25 mM glucose in the media. While FAHFAs increase insulin secretion from Ins1 cells at both low and high glucose under this particular set of cell culture conditions, in human islets FAHFAs stimulate insulin secretion only at high glucose levels (see FIGS. 37 and 38). Thus, the effect of FAHFAs on insulin secretion in human islets is physiologic.

Figure 23:
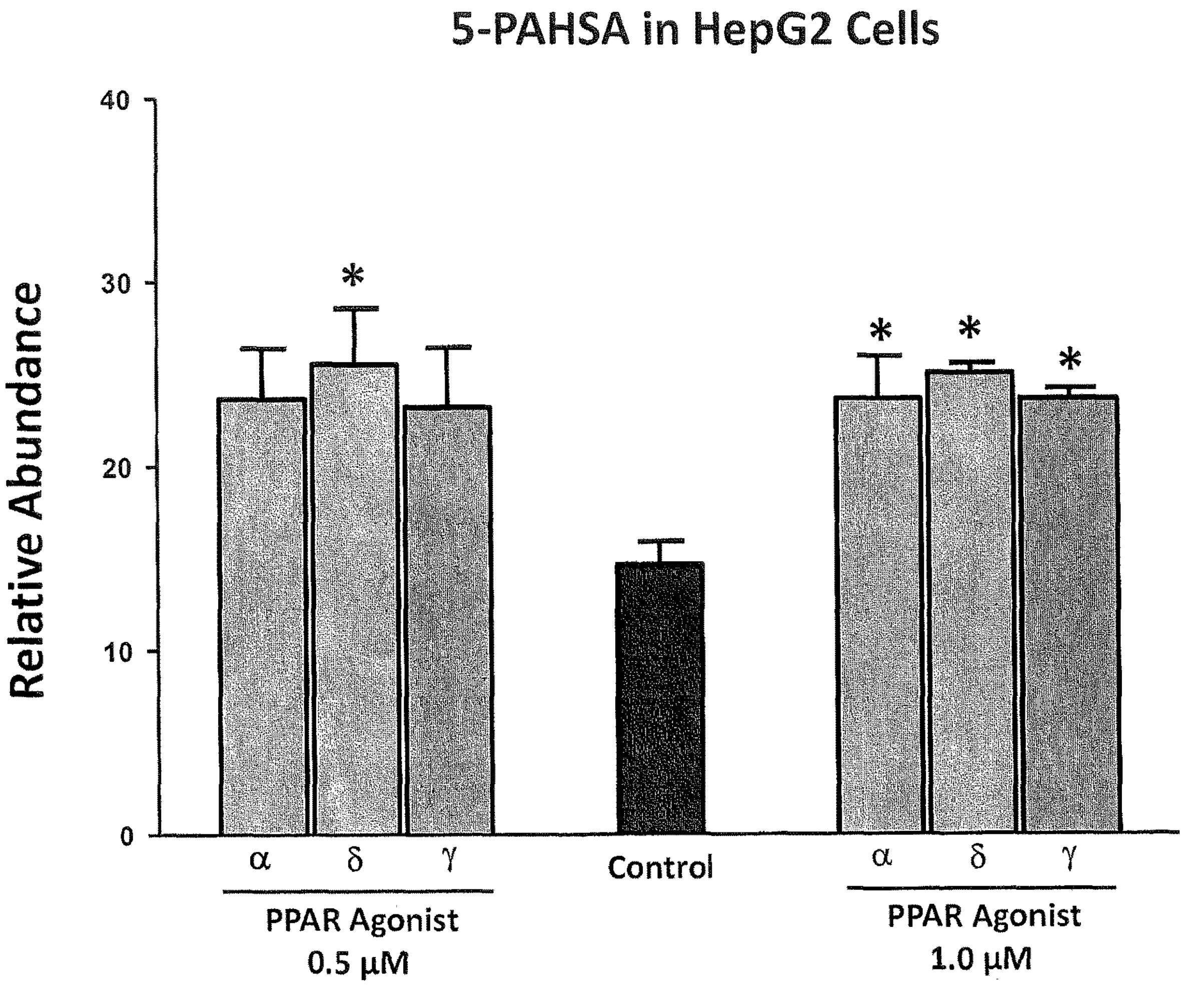
Figure 24:
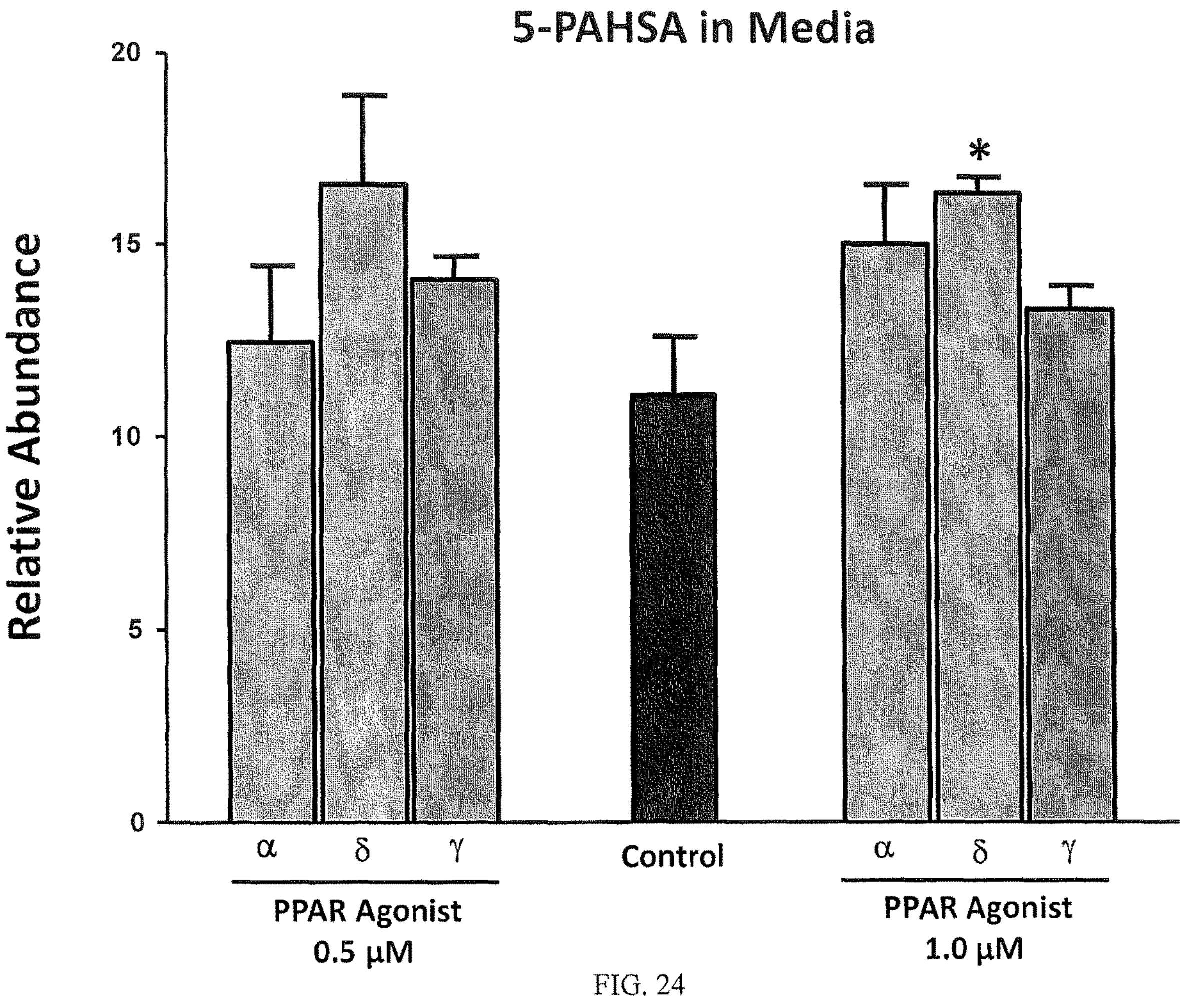

FIGS. 23 and 24 are bar graphs that summarize the effect of different PPAR agonists on FAHFA levels in a cultured liver cell line.

Figure 25:
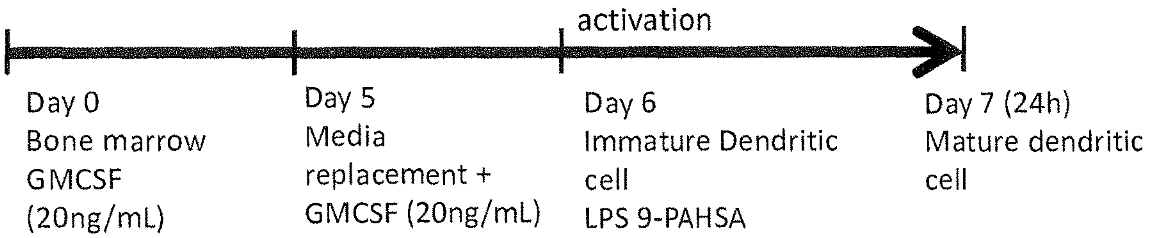

FIG. 25 is a graphical representation of the experimental design used to examine the effect of FAHFAs on the inflammatory cytokine cascade.

Figures 26A, 26B:
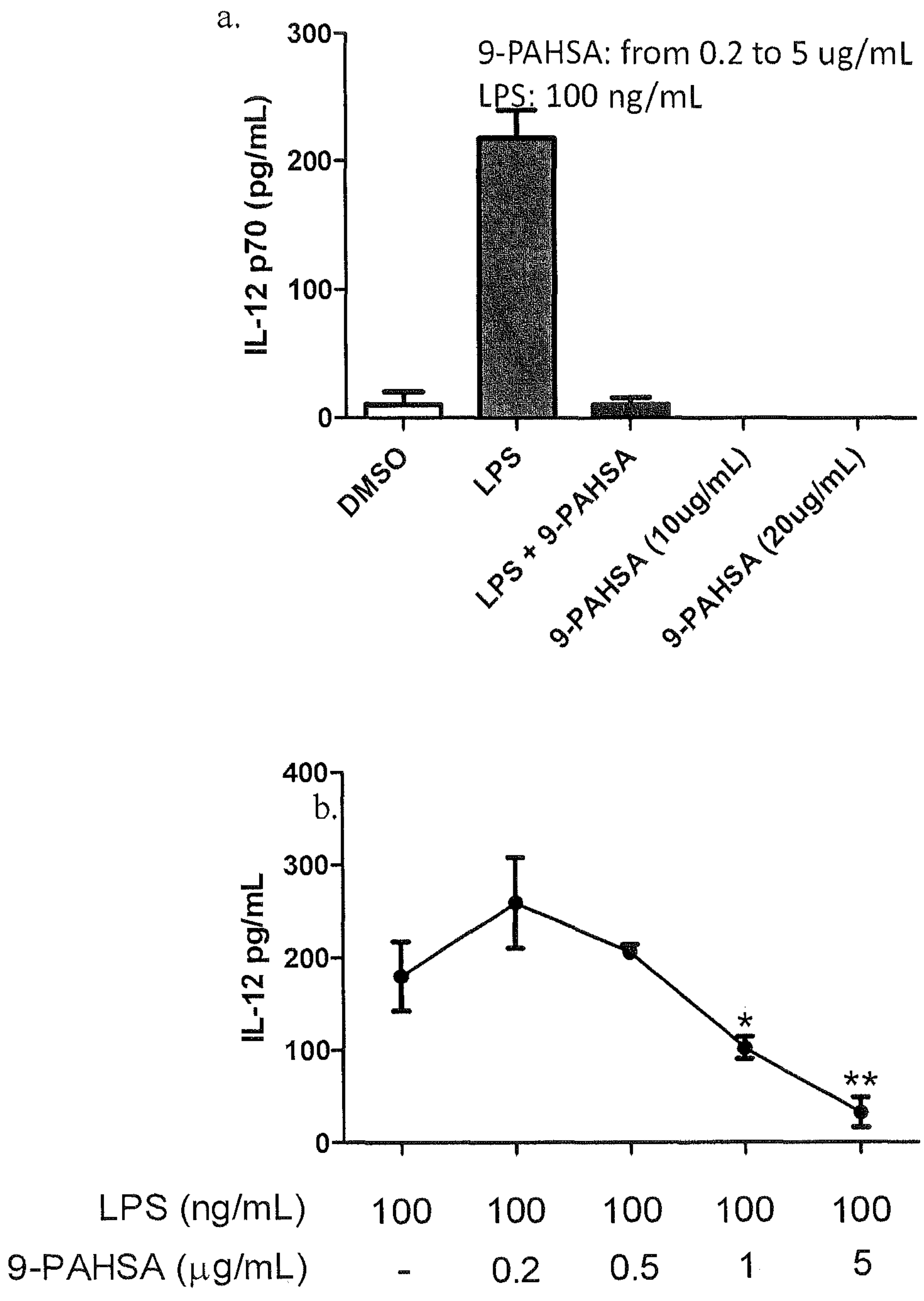

FIGS. 26A and 26B are graphs of secreted IL-12 levels from LPS-stimulated macrophages treated with different levels of FAHFAs.

Figure 27:
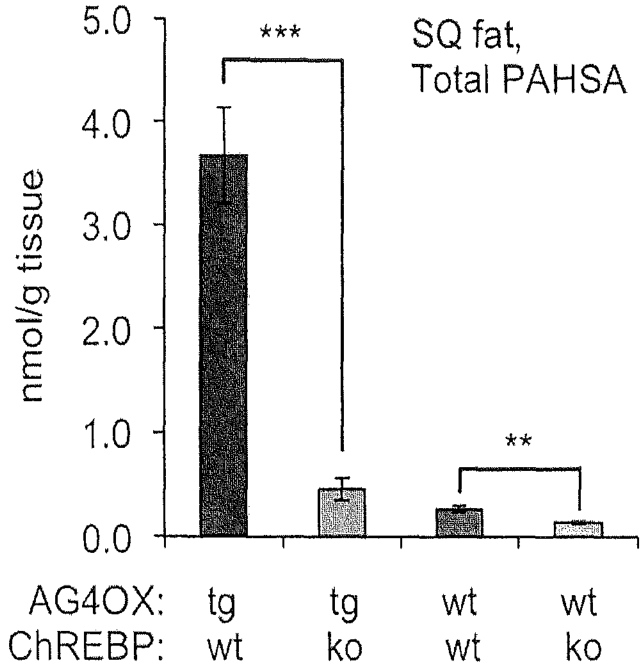

FIG. 27 shows that upregulation of FAHFA levels in subcutaneous white adipose tissue (SQ fat) upon GLUT4 overexpression (AG4OX) requires ChREBP. To determine whether adipose ChREBP is required for the increased PAHSA levels in adipose tissue resulting from GLUT4 overexpression, AG4OX mice were crossbred with whole-body ChREBP KO mice. Total PAHSA levels normalized in adipose tissue after deletion of ChREBP in AG4OX mice. Statistical significance was assessed by a Student's t test (, p<0.01; *, p<0.001; n=4).

Figure 28:
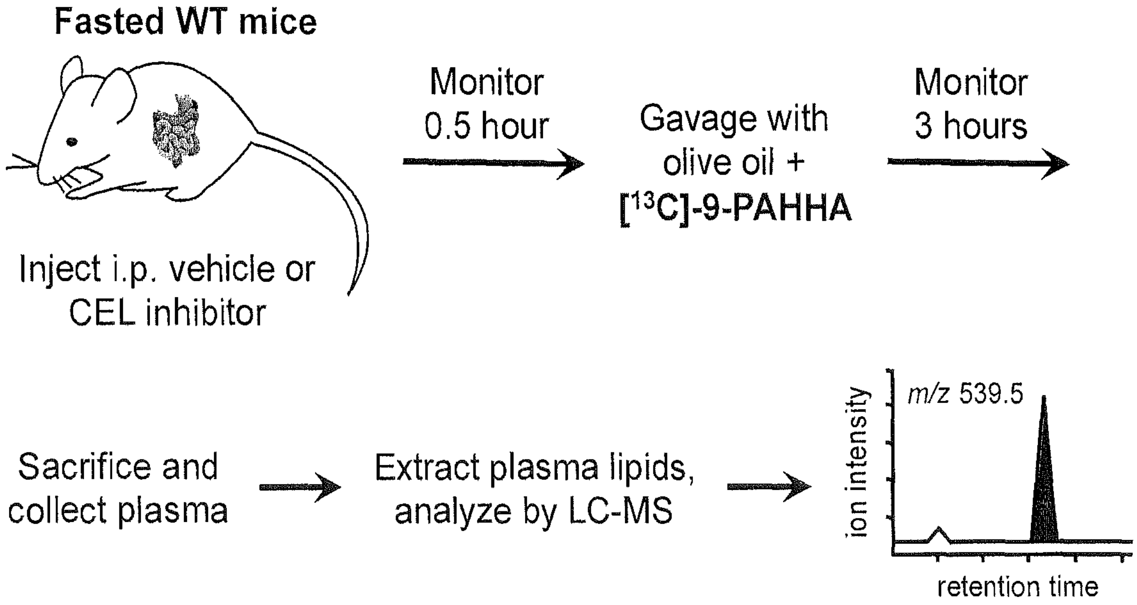

FIG. 28 shows a FAHFA gavage experiment workflow. Mice were fasted overnight then injected with WWL92. After 30 minutes, the were gavaged with the double-labeled FAHFA, [$^{13}$C]-9-PAHHA, dissolved in olive oil. After three hours, mice were sacrificed and plasma is collected and extracted with chloroform-methanol. Lipid extracts were analyzed by LC-MS in targeted MRM mode to look for either intact [$^{13}$C]-9-PAHHA (m/z 539.5) or reesterified lipids containing HHA. Analysis of 9-HHA itself can be performed in selected ion monitoring (SIM) mode (m/z 285.3).

Figure 29:
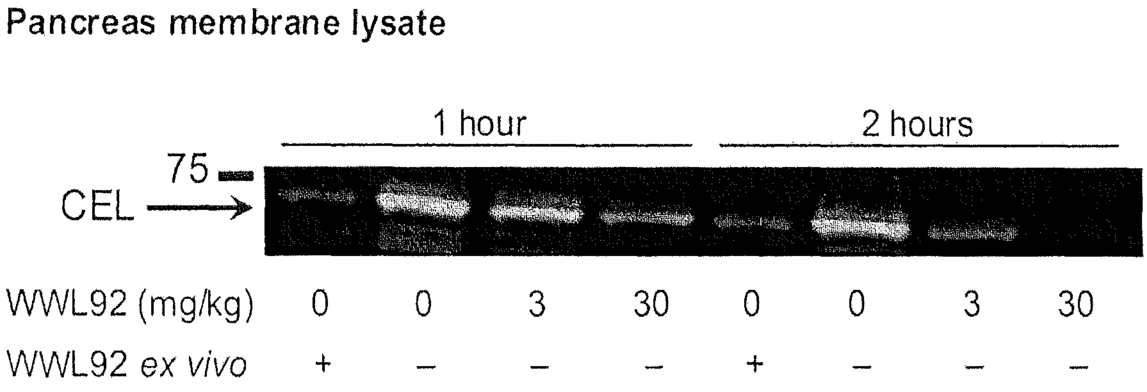

FIG. 29 shows complete inhibition of CEL by WWL92 in vivo. Labeling of CEL was by an activity-based probe was inhibited in mice treated with WWL92. Mice were fasted overnight and an intraperitoneal injection of WWL92 was administered at the indicated doses. After either 1 or 2 hours, the mice were sacrificed and the pancreas was harvested. Membrane lysates of the pancreas tissue were prepared, and they were first reacted with either WWL92 (20 μM) or DMSO to ensure that WWL92 could inhibit CEL ex vivo. Reaction with an activity-based probe (FP-Rh) followed by separation of proteins by SDS-PAGE permitted fluorescent detection of FP-Rh-labeled proteins. The lower intensity of bands in WWL92-treated mice indicated that a greater proportion of the CEL was pre-labeled with WWL92 and not available for labeling by FP-Rh.

Figure 30:
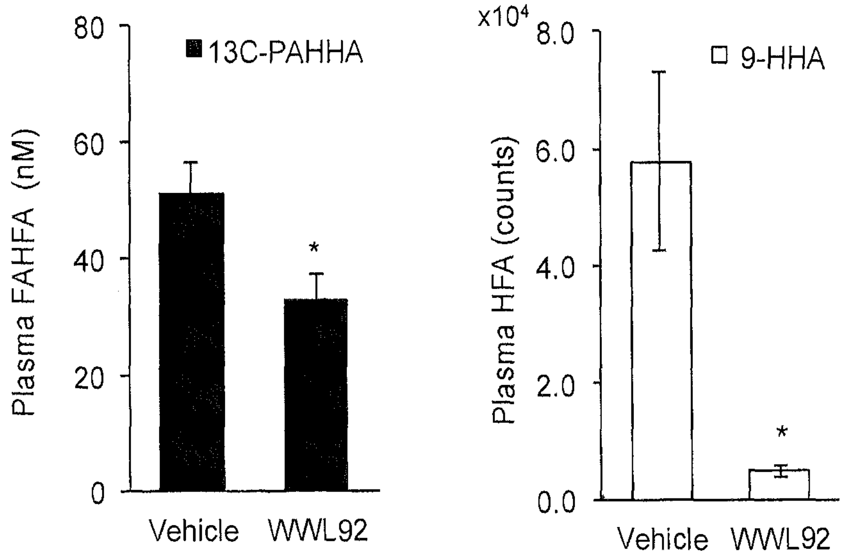

FIG. 30 shows bar graphs illustrating that plasma levels of [$^{13}$C]-9-PAHHA and its hydrolyzed product 9-HHA in mice after treatment with 40 mg/kg WWL92. Mice were injected intraperitoneally with an aqueous solution of the inhibitor 0.5 hour prior to gavage with 0.1 mL olive oil containing 0.15 mg [$^{13}$C]-9-PAHHA. Mouse plasma was collected after 3 hours and the levels of the metabolites were measured by QQQ-MS using [$^{13}$C]-9-PAHSA as an internal standard. Values for 9-HHA are presented as average signal intensity. Statistical significance was determined by an unpaired Student's t test (*, n<0.05; n=3-4).

Figure 31:
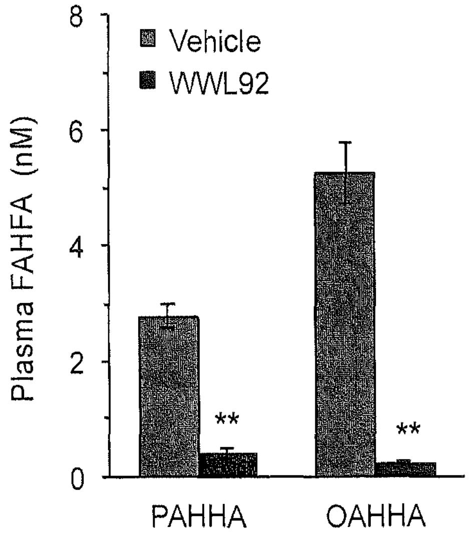

FIG. 31 shows a bar graph illustrating that plasma levels of transesterified products of [$^{13}$C]-9-PAHHA. The levels of PAHHA and OAHHA were measured by QQQ-MS using [$^{13}$C]-9-PAHSA as an internal standard, all of which possessed unique MRM transitions. Statistical significance was determined by an unpaired Student's t test (**, n<0.01; n=3-4).

Figure 32:
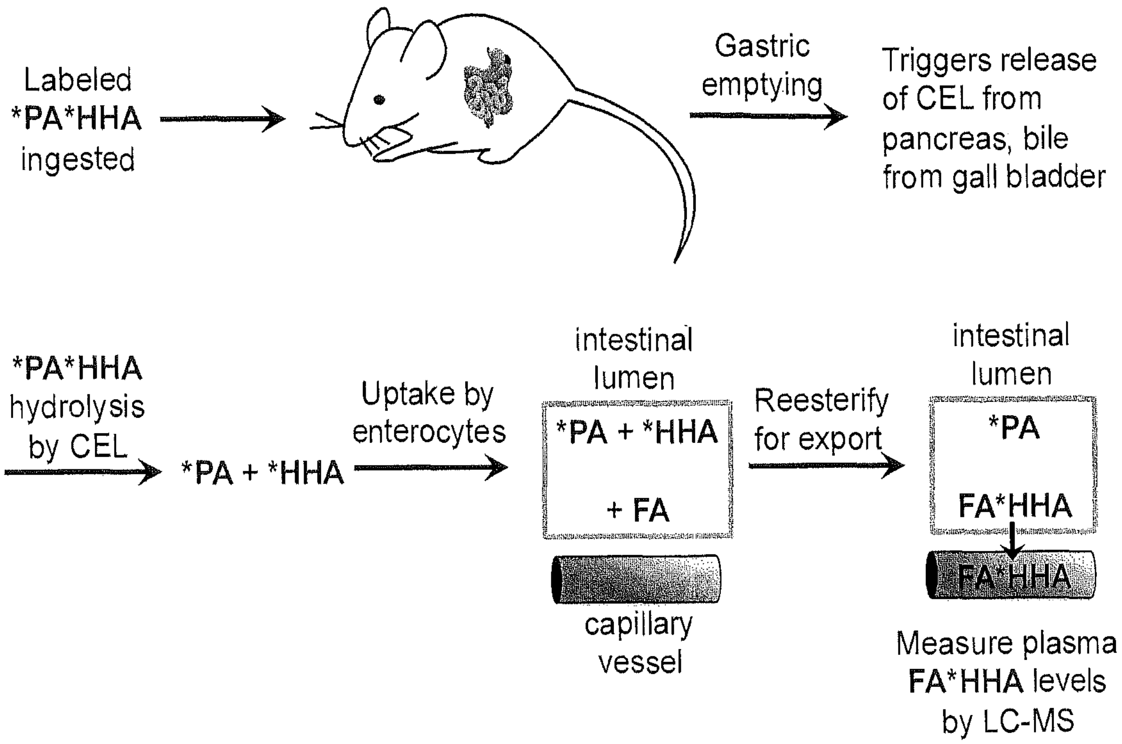

FIG. 32 shows CEL degradation of FAHFAs may follow a model similar to the canonical lipid absorption pathway. Double-labeled FAHFA (*PA*HHA) dissolved in extra light olive oil is ingested and proceeds from the stomach to the duodenum via gastric emptying. Lipid content in the chyme triggers release of bile and pancreatic enzymes, which include CEL. Labeled FAHFA is hydrolyzed in intestinal lumen to *PA and *HHA, permitting uptake by the enterocytes lining the lumen wall. Once inside, *HHA can be re-esterified with a natural fatty acyl group (FA) to give FA*HHA or exported directly to bloodstream as *HHA.

Figure 33:
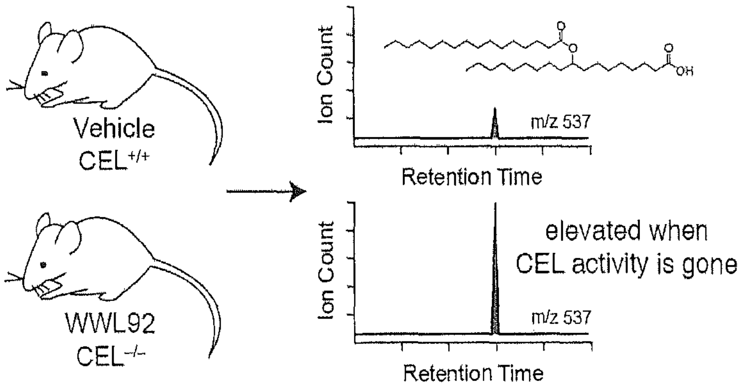

FIG. 33 illustrates an experimental design for in vivo experiments to show that CEL is an endogenous FAHFA-hydrolase.

Figure 34:
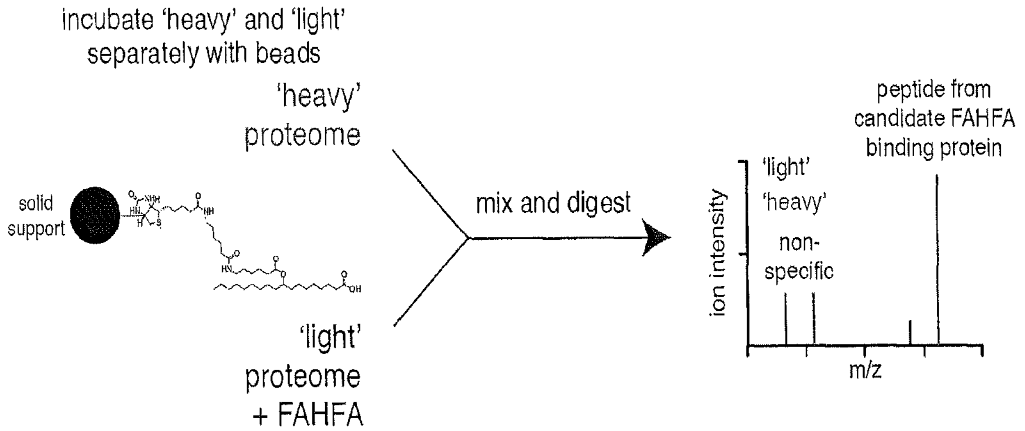

FIG. 34 illustrates an experimental design for enrichment of FAHFA-binding proteins using SILAC.

Figure 35:
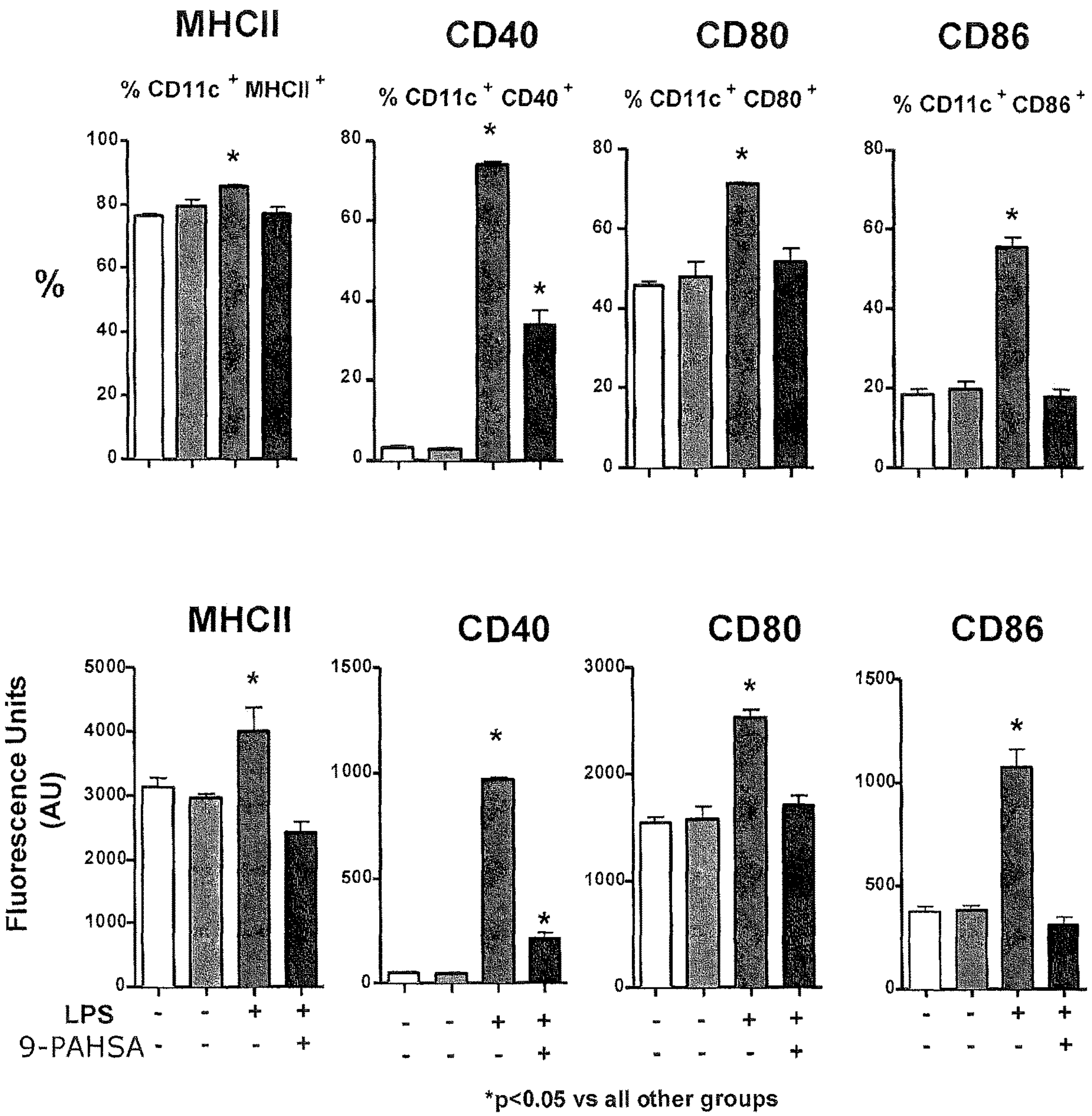

FIG. 35 shows bar graphs that illustrate that 9-PAHSA prevents LPS-induced dendritic cell activation by reducing expression of MHCII and co-stimulatory molecules (CD40, CD80, CD86) by dendritic cells as a percentage of activated dendritic cell (top row) and in fluorescence units (bottom row). *p<0.05 vs all other groups.

Figure 36:
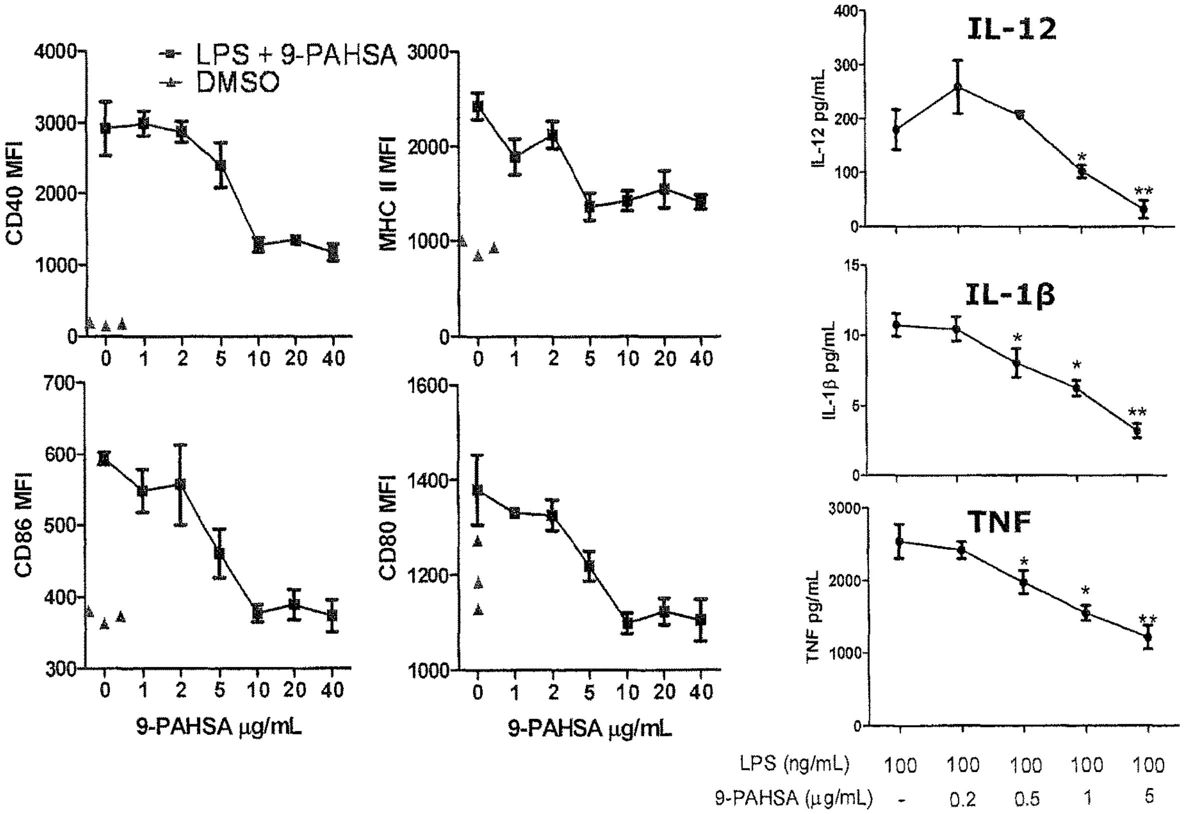

FIG. 36 shows line graphs that illustrate 9-PAHSA prevents LPS-induced dendritic cell activation in a dose dependent manner.

Figure 37:
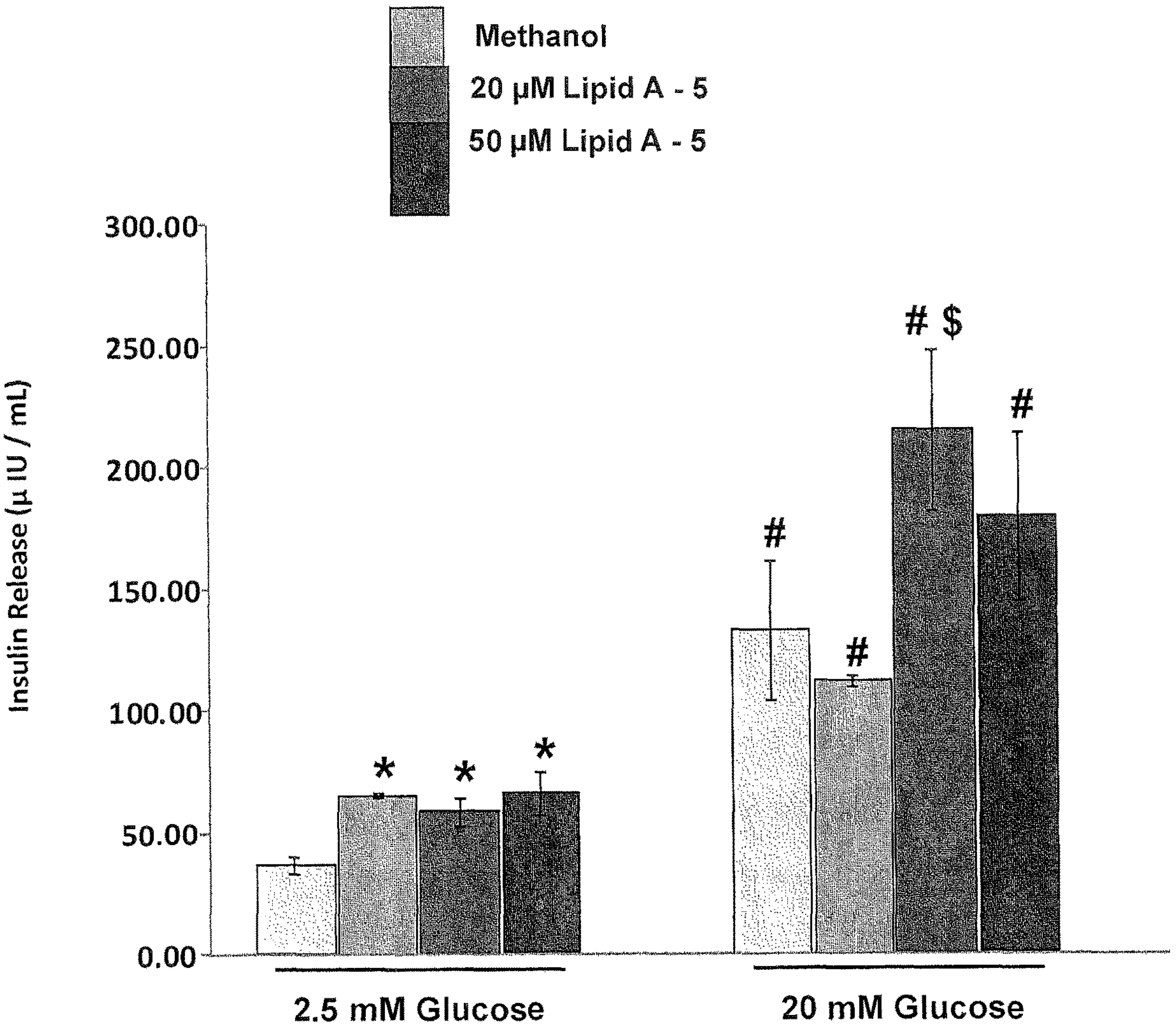

FIG. 37 is a bar graph evidencing that 5-PAHSA (Lipid A-5) induces Glucose Stimulated Insulin Secretion in Human islets from Donor 1. *p<0.05 vs. 2.5 mM glucose alone; #p<0.05 vs. respective 2.5 mM glucose controls; $p<0.05 vs. 20 mM glucose alone.

Figure 38:
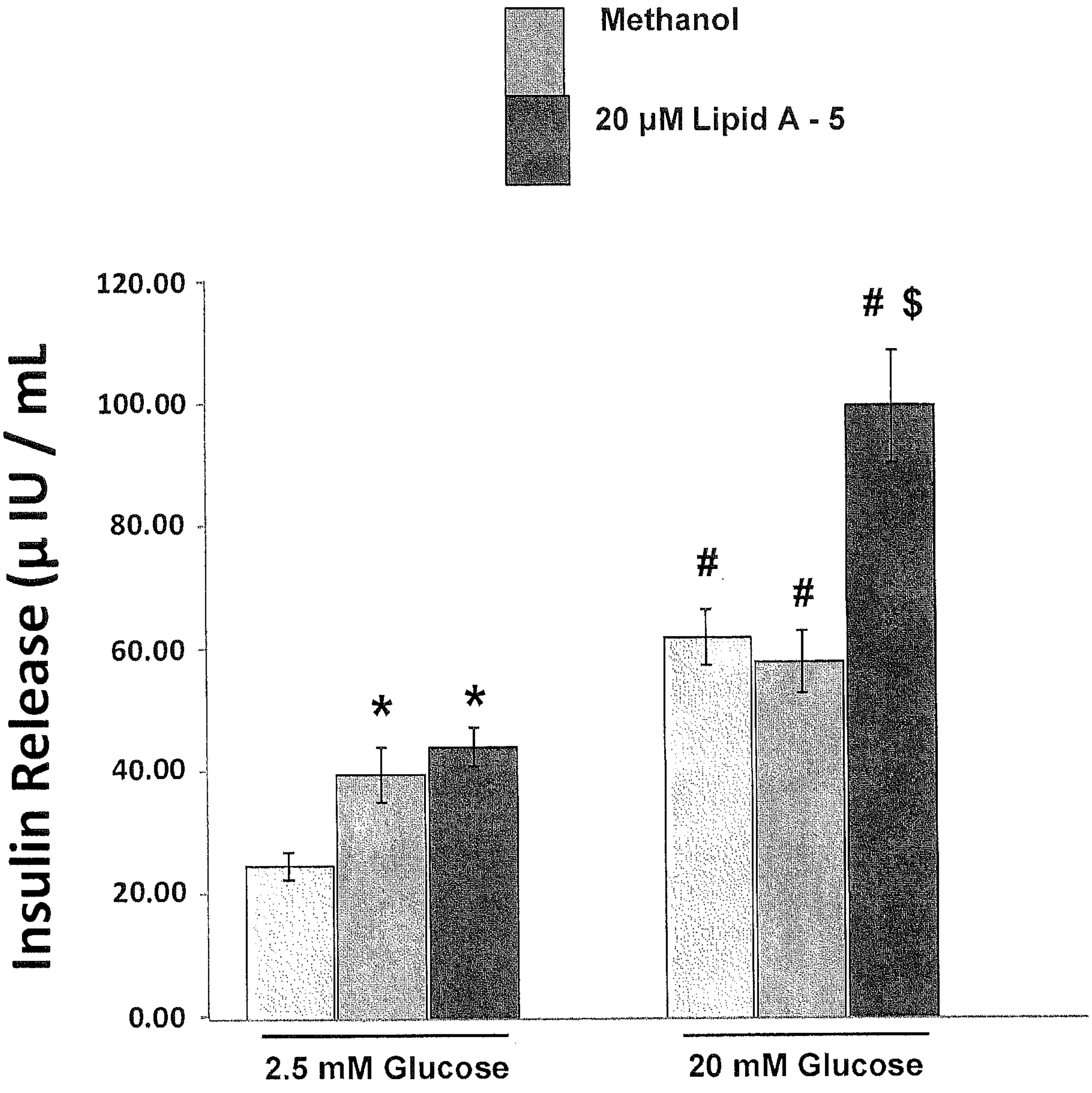

FIG. 38 is a bar graph evidencing that 5-PAHSA (Lipid A-5) induces Glucose Stimulated Insulin Secretion in Human islets from Donor 2. *p<0.05 vs. 2.5 mM glucose alone; #p<0.05 vs. respective 2.5 mM glucose controls; $p<0.05 vs. 20 mM glucose alone.

FIGS. 39A-C are line graphs showing that lipids A9 (9-PAHSA) and A5 (5-PAHSA) induce Ca2+ flux from intracellular stores in STC-1 cells. Lipids were applied at t=3 min, Results=average of 10 cells. 49A is STC-1 Linoleic Acid 100 uM (positive control for Ca2+ flux) No Ca2+; 49B is STC-1 Lipid A9 100 uM No Ca2+; 49C is STC-1 Lipid A5 100 uM No Ca2+.

Figure 40:
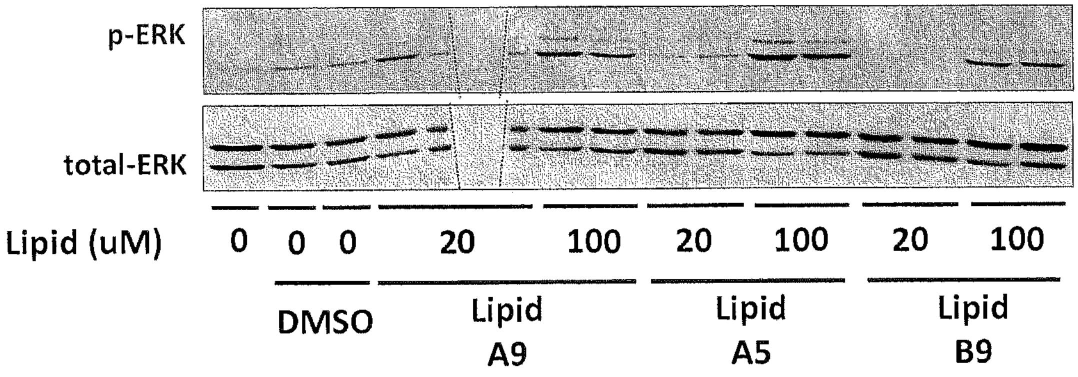

FIG. 40 is a Western Blot illustrating that lipids A9 (9-PAHSA), B9 (9-OAHSA), and A5 (5-PAHSA) induce ERK phosphorylation in STC-1 cells.

Figure 41:
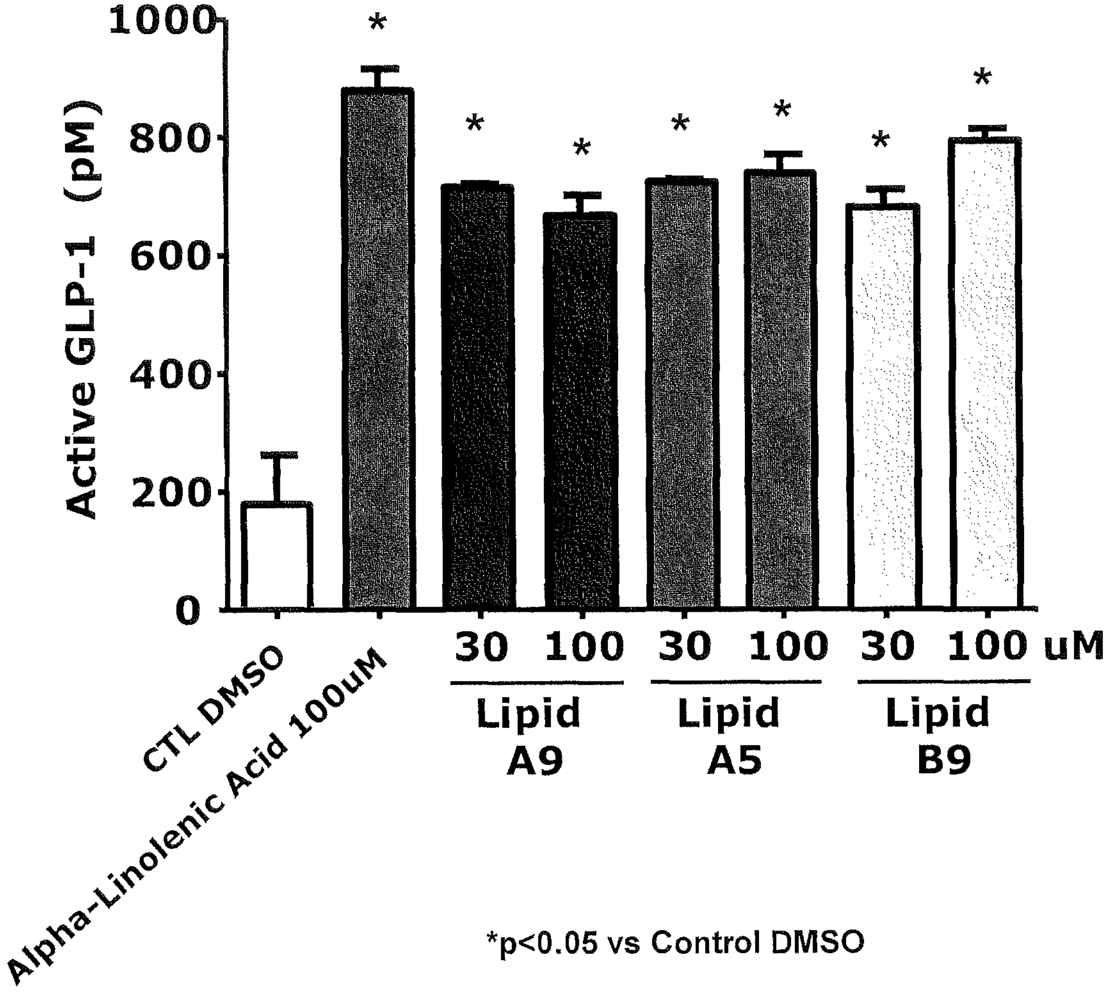

FIG. 41 is a bar graph illustrating that lipids (9-PAHSA), B9 (9-OAHSA), and A5 (5-PAHSA) induce GLP-1 secretion in Stc-1 enteroendocrine cells.

Figure 42:
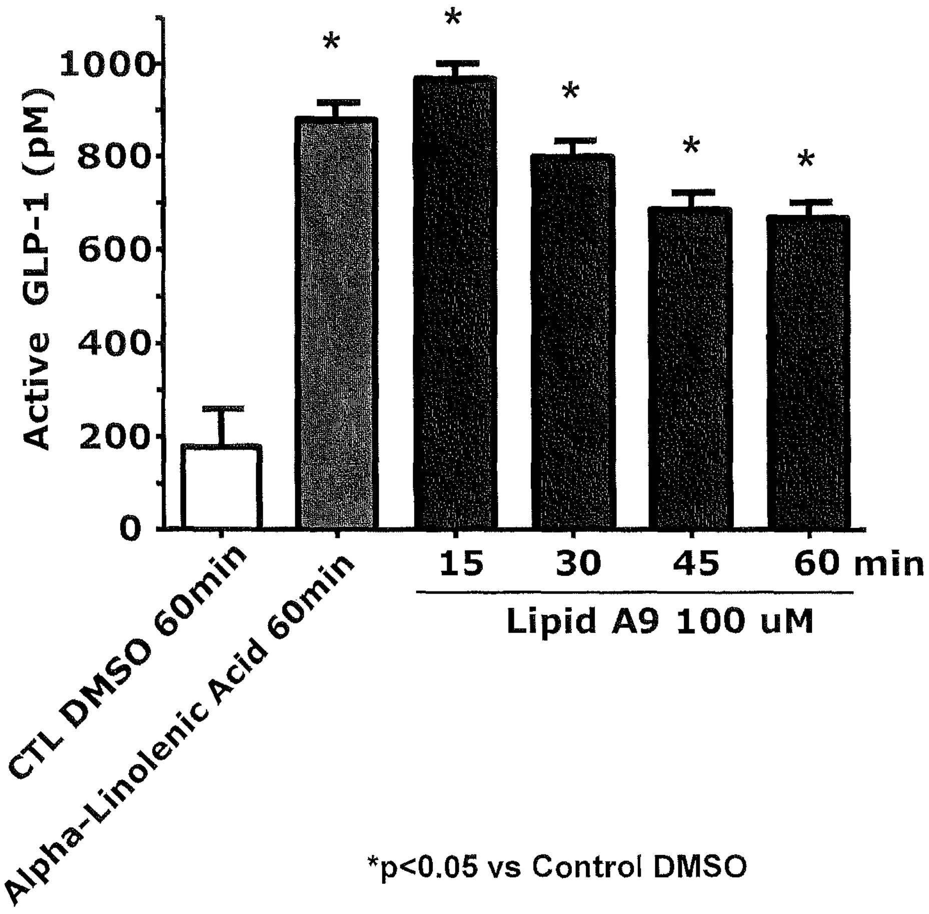

FIG. 42 is a bar graph time series illustrating that the time course for GLP-1 secretion by 9-PAHSA in Stc-1 cells is very rapid and sustained.

Figure 43:
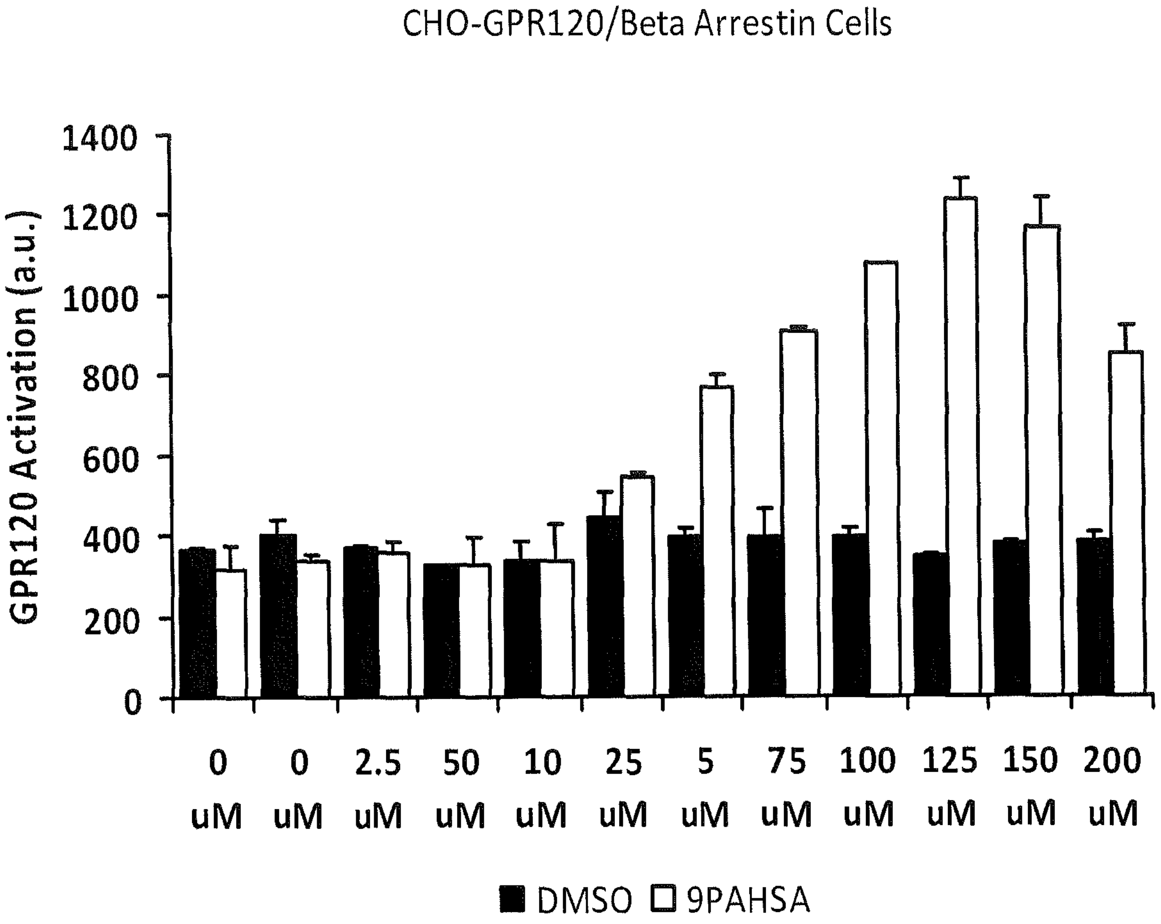

FIG. 43 is a bar graph evidencing that lipid A9 (9-PAHSA) is a ligand for the GPCR, GPR120.

Figure 44:
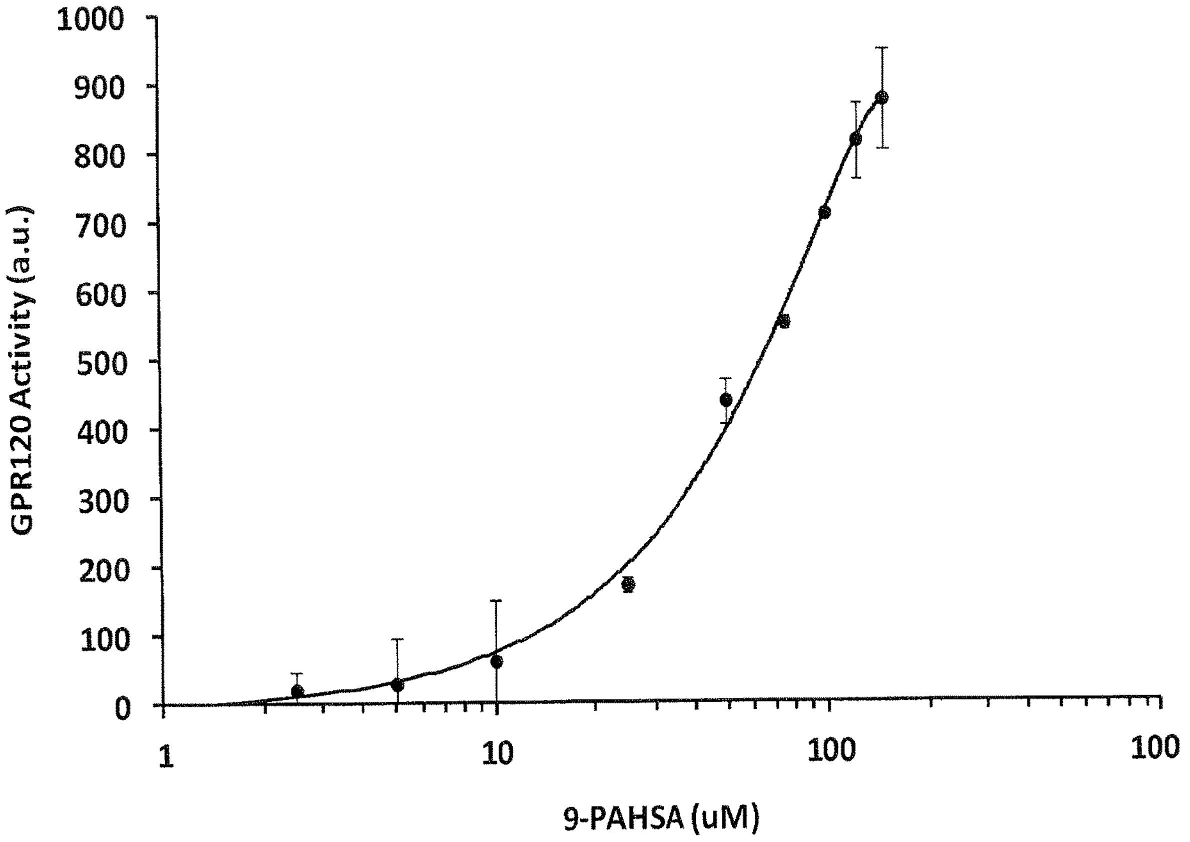

FIG. 44 is a titration curve, further illustrating that lipid A9 (9-PAHSA) is a ligand for the GPCR, GPR120.

Figure 45:
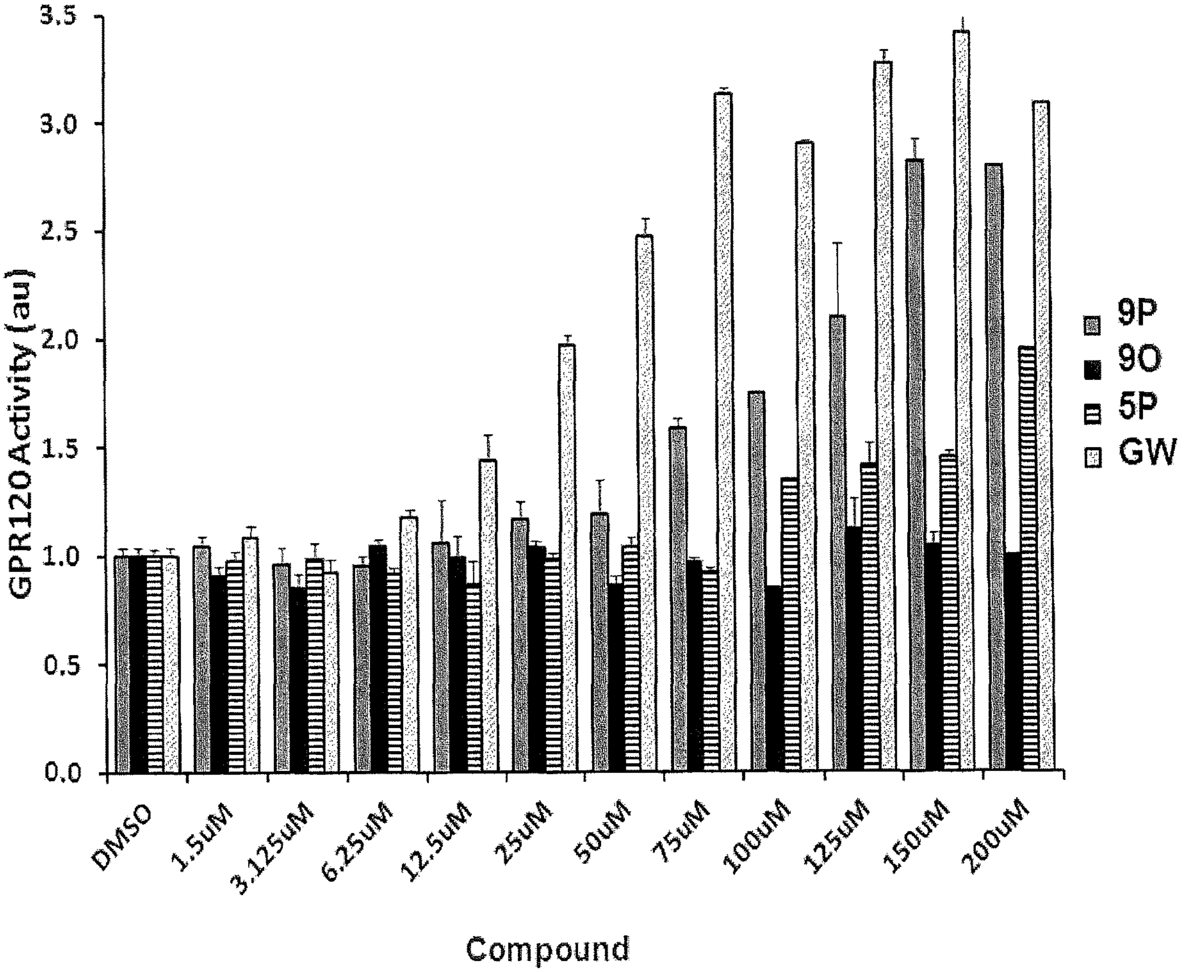

FIG. 45 is a series of bar graphs illustrating that 9-PAHSA and 5-PAHSA, but not 9-OAHSA, activate GPR120.

Figure 46:
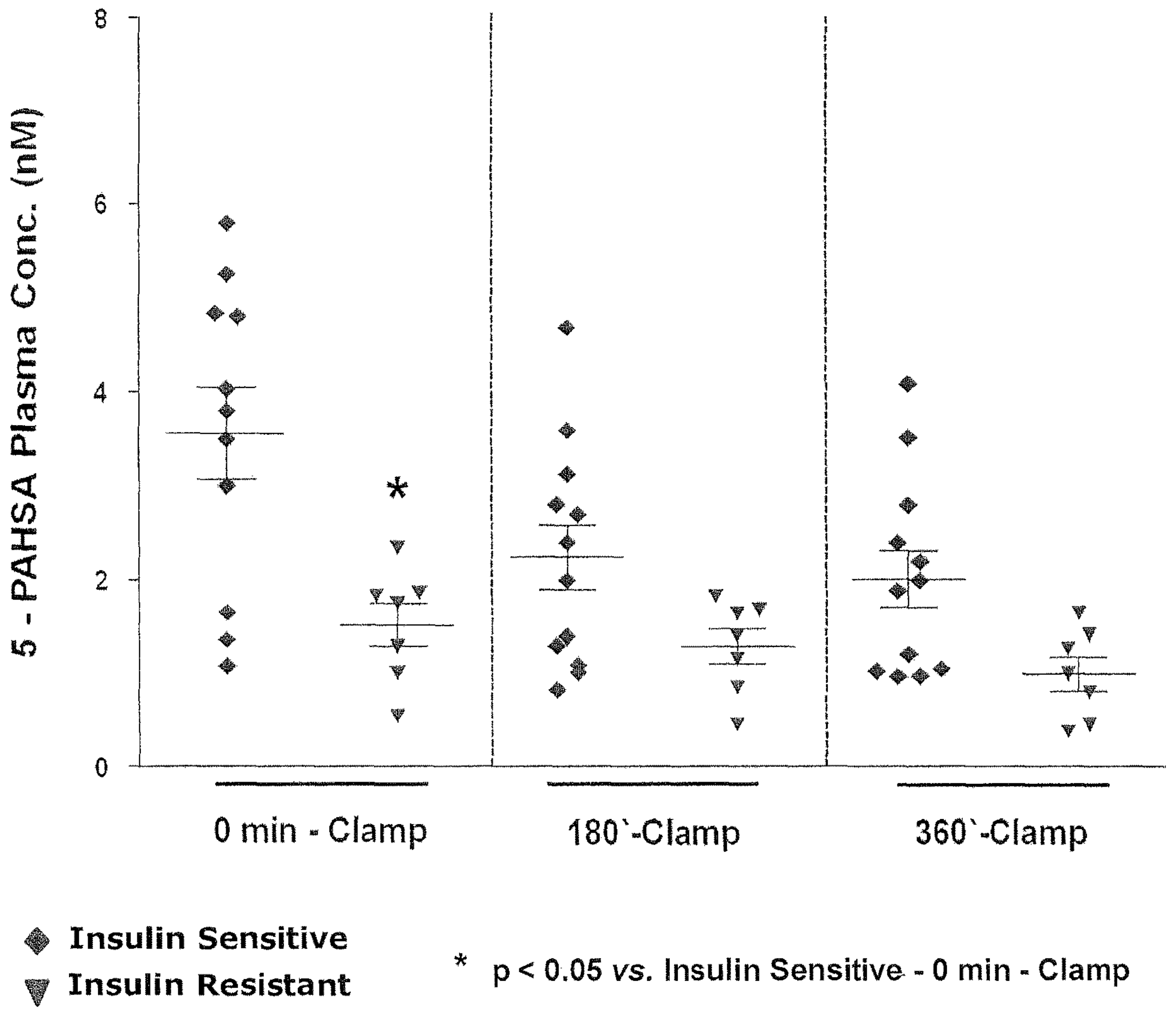

FIG. 46 illustrates that the levels of 5-PAHSA in plasma of insulin sensitive and insulin resistant subjects were lower after clamp that at baseline.

Figure 47:
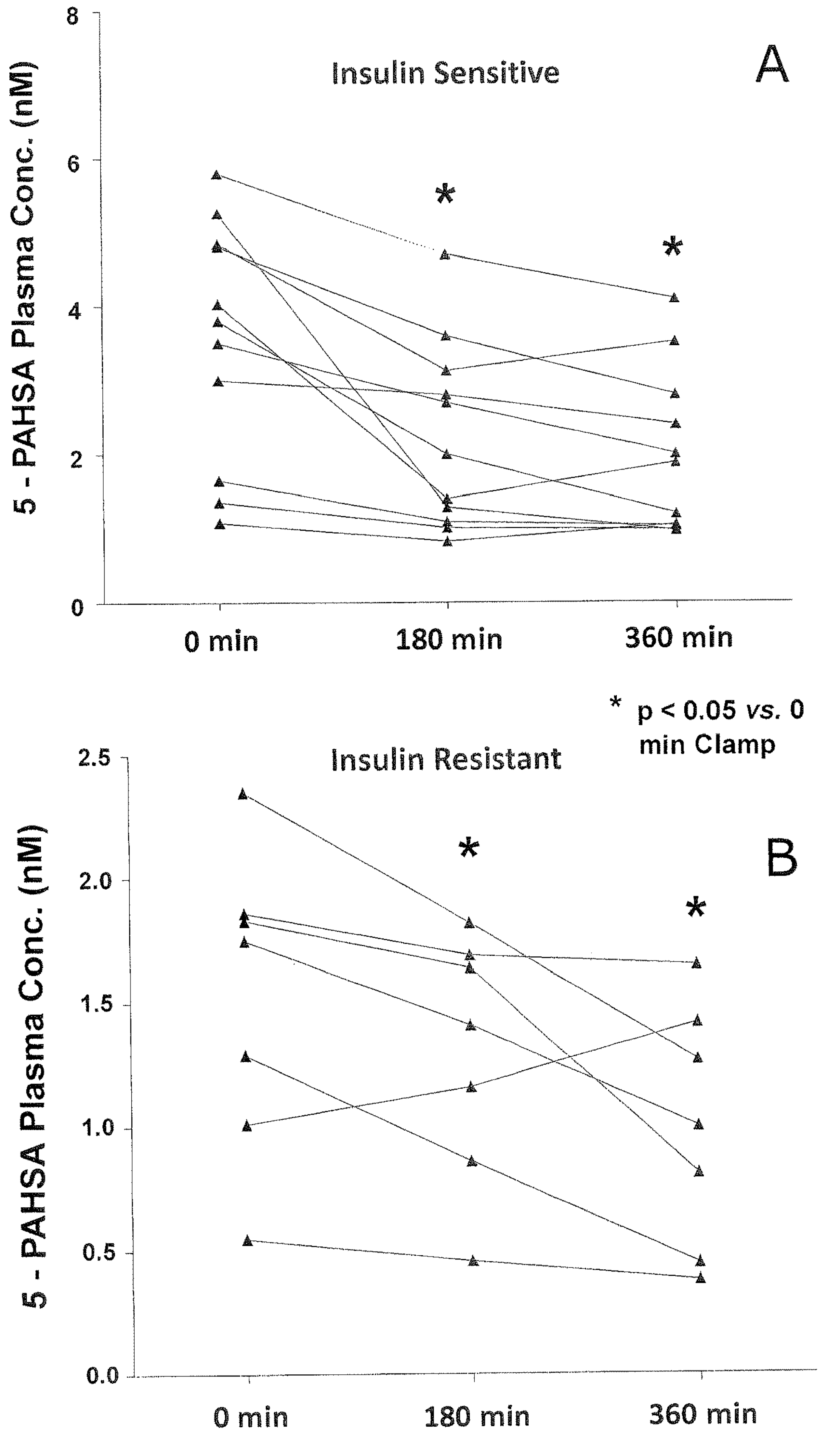

FIGS. 47A and 47B illustrate that glucose-insulin infusion (clamp) lowers 5-PAHSA levels in plasma of insulin sensitive (FIG. 47A) and insulin resistant (FIG. 47B) human subjects.

Figure 48:
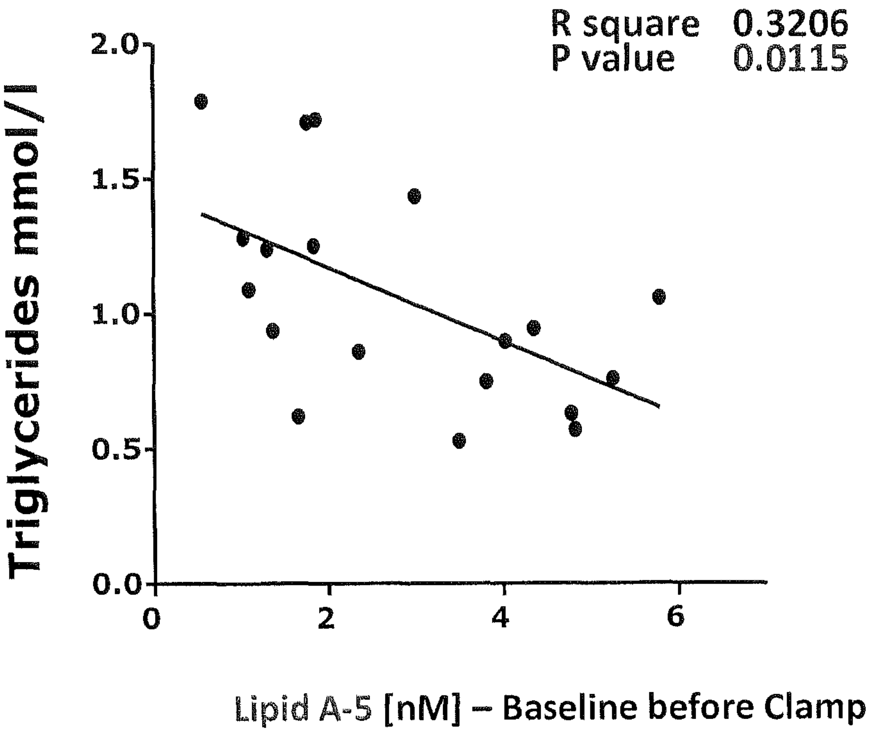

FIG. 48 is a scatterplot illustrating the inverse correlation between the levels of 5-PAHSA in plasma from humans with plasma triglycerides in the fasting state.

FIG. 49A is a volcano plot showing comparative lipidomics of SQ WAT from AG4OX and WT mice, which reveals the presence of a group FAHFA-derived ions that are significantly elevated in AG4OX mice. FIG. 49B shows structural analysis of the FAHFA ion. FIGS. 49C-D show exemplary FAHFA structures and their quantification in serum of WT and AG4OX mice. FIG. 49E shows total PAHSA levels in serum and tissues of WT and AG4OX mice.

Figure 50E:
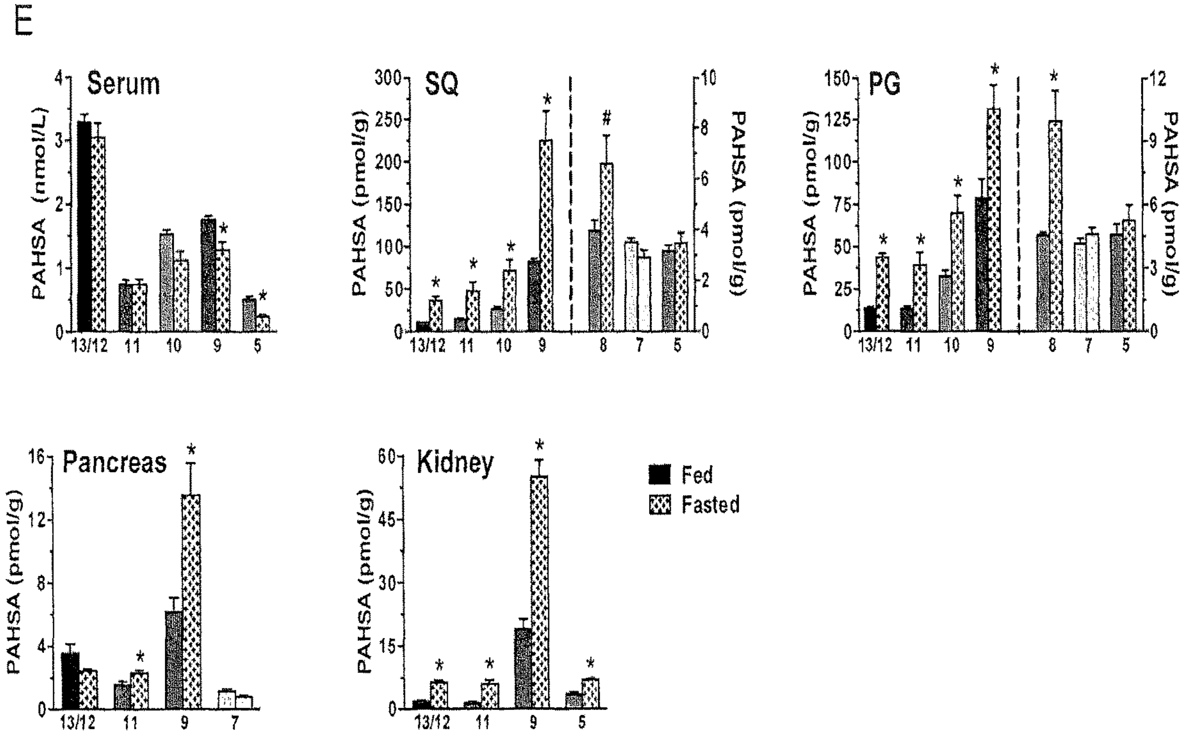

FIGS. 50A-E relate to the identification and quantification of PAHSA isomers in mouse serum and tissues. Specifically, FIG. 50A is a chromatogram showing co-elution of PAHSA isomers from serum and SQ WAT of WT and AG4OX mice with synthetic 12-, 11-, 10-, 9-, 8-, 6-, 5-, and 4-PAHSA standards. FIG. 50B shows the distribution and quantification of PAHSA isomers in serum and tissues of WT and AG4OX mice. n=3-5 per group, *p<0.05 compared to WT (t-test). FIG. 50C shows distribution and quantification of 13/12-, 9- and 5-PAHSA isomers in serum and tissues of WT mice. n=3-5 per group, tissues with same letter not significantly different from other tissues within the same group (p>0.05, ANOVA), tissues with different letters significantly different from all other tissues within the same group (p<0.05, ANOVA). FIG. 50D shows total PAHSA levels in serum and tissues of WT mice in fed or fasted (16 h) states. *p<0.05 compared to fed (t-test), $^{a,b,c,d}$tissues with same letter are not different from other tissues within the same group (p>0.05, ANOVA), tissues with different letters are different from all other tissues within the same group (p<0.05, ANOVA). FIG. 50E shows quantification of PAHSA isomers in serum and tissues of WT mice in fed or fasted (16 h) states. n=3-5 per group, *p<0.05, $^{\#}$<0.07 compared to fed (t-test). All data are means±s.e.m.

FIGS. 51A-C are bar graphs showing levels of PAHSA isomers in tissues of mice on chow and HFD and in mouse and human food types. Specifically, FIG. 51A shows quantification of PAHSA isomers in serum, SQ WAT, PG WAT, BAT and liver of WT mice fed on chow or HFD. n=3-6 per group, *p<0.05 compared to chow by t-test. FIG. 51B shows quantification of PAHSA isomers in chow and HFD. n=3 per group. FIG. 51C shows quantification of PAHSA isomers in human foods. n=3 per group. Data are presented as mean±s.e.m.

FIGS. 52A-E are plots correlating decreased PAHSA levels with insulin-resistance in humans. FIG. 52A shows quantification of total PAHSA and individual PAHSA isomers in serum of insulin-sensitive and insulin-resistant non-diabetic humans (see table S1 for metabolic characteristics of participants). n=6-7 per group. FIG. 52B is a plot showing correlation between insulin-sensitivity (glucose infusion rate) and serum total PAHSA and individual PAHSA isomers. n=13. FIG. 52C shows quantification of total PAHSA and individual PAHSA isomers in SQ WAT of insulin-sensitive and insulin resistant humans. n=6-7 per group. FIG. 52D is a plot showing correlation between insulin-sensitivity (glucose infusion rate) and SQ WAT total PAHSA and individual PAHSA isomers. n=13. FIG. 52E is a plot showing correlation between SQ WAT and serum 5-PAHSA levels. p values are depicted on individual graphs (t-test). All data are presented as mean±s.e.m.

FIGS. 53A-G shows that PAHSAs improve glucose tolerance and insulin sensitivity in vivo and induce insulin and GLP-1 secretion. FIG. 53A shows the results of an oral glucose tolerance test (OGTT) with HFD-fed mice gavaged with 5-PAHSA (upper panel), 9-PAHSA (lower panel) or vehicle control 30 min prior to the (OGTT). n=12-14 per group, *p<0.05 compared to vehicle at same time. Area under the curve (AUC), *p<0.05 compared to vehicle. FIG. 53B shows HFD-fed mice gavaged with 5-PAHSA (upper panel), 9-PAHSA (lower panel) or vehicle control 2.5 hours (5-PAHSA) or 3 hours (9-PAHSA) prior to an insulin tolerance test (ITT). n=12-14 per group, *p<0.05 compared to vehicle at same time. Area above the curve (AAC). *p<0.05 compared to vehicle. FIG. 53C shows aged, chow-fed mice (45-weeks old) gavaged with 5-PAHSA 30 min prior to an oral glucose tolerance test (OGTT) n=12-14 per group, *p<0.05 compared to vehicle at same time. Area under the curve (AUC). *p<0.05 compared to vehicle. FIG. 53D is a bar graph showing serum insulin levels 5 min post glucose challenge in chow-fed mice gavaged with 5-PAHSA or vehicle (glucose values shown in FIG. 53C). n=12-14 per group, *p<0.05 compared to vehicle by t-test. FIG. 53E is a bar graph showing serum GLP-1 levels 5 min post glucose challenge from chow-fed mice gavaged with 5-PAHSA or vehicle (glucose levels in FIG. 53C). n=12-14 per group, *p<0.05 compared to vehicle by t-test. FIG. 53F are bar graphs showing insulin secretion from primary human islets from two independent donors. Islets were incubated with low (2.5 mM) or high (20 mM) glucose ex vivo in the presence of 5-PAHSA (20 μM) or vehicle control. n=100 islets per condition, *p<0.05 compared to control 2.5 mM glucose, $^{\#}$p<0.05 compared to respective treatments at 2.5 mM glucose, $^{\$}$p<0.05 compared to control or diluents at 20 mM glucose by t-test. FIG. 53G are bar graphs showing active GLP-1 secretion from STC-1 cells in response to 5-PAHSA (5-P), 9-PAHSA (9P), α-Linolenic Acid (LA), GW9508 (GW) or vehicle control (DMSO). n=4 per group, *p<0.05 compared to vehicle by t-test. All data are mean±s.e.m. See also FIG. 56.

Figure 57:
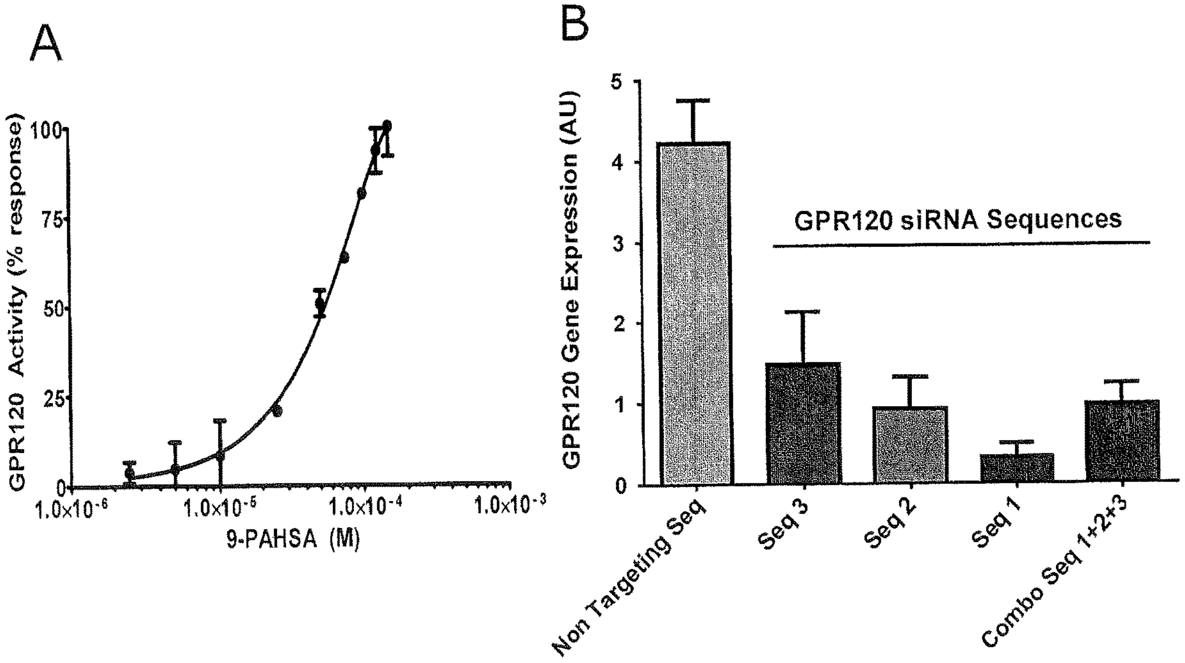

FIGS. 54A-D show glucose uptake regulation by PAHSAs and Glut4 translocation via GPR120. FIG. 54A is a bar graph showing insulin-stimulated glucose transport in 3T3-L1 adipocytes treated 9-PAHSA (20 μM) or vehicle (DMSO) control for 6 days. n=6 per group, *p<0.05 compared to vehicle by t-test. FIG. 54B is a bar graph showing insulin (10 nM)-stimulated glucose transport in 3T3-L1 adipocytes transfected with control siRNA or GPR120 siRNA and treated 5-PAHSA (10 μM), 9-PAHSA (10 μM) or vehicle (DMSO) control for 2 days. n=3 per group, *p<0.05 compared to DMSO+control siRNA or GPR120 siRNA alone, $p<0.05 compared to control siRNA or GPR120 siRNA+insulin and GPR120 siRNA+insulin+PAHSA by t-test. FIG. 54C is a panel showing Glut4 plasma membrane translocation in 3T3-L1 adipocytes transfected with control siRNA or GPR120 siRNA and treated with 9-PAHSA in the presence or absence of insulin. 6 separate experiments were carried out without RNAi and 3 experiments with RNAi; each experiment had greater than 50 cells per experimental condition. FIG. 54D is a bar graph showing quantification of Glut4 translocation in panel C. *p<0.05 compared to control siRNA+insulin and GPR120 siRNA+insulin+9-PAHSA by t-test. All data are presented as mean±s.e.m. See also FIG. 57.

FIGS. 55A-C show insulin resistance in mice fed HFD for 9 weeks. Body weight of the mice fed chow or HFD for 9 weeks. Oral glucose tolerance test 6 h after food removal in female mice fed chow or HFD. Area under the OGTT curve (AUC) measured from time 0 to 120 minutes. Data are presented as mean±s.e.m. *p<0.05 vs. by t-test. N=9-12 mice per group. For lipid measurements in FIG. 51A, tissues from 4 chow and 3 HFD mice were used.

Figure 56:
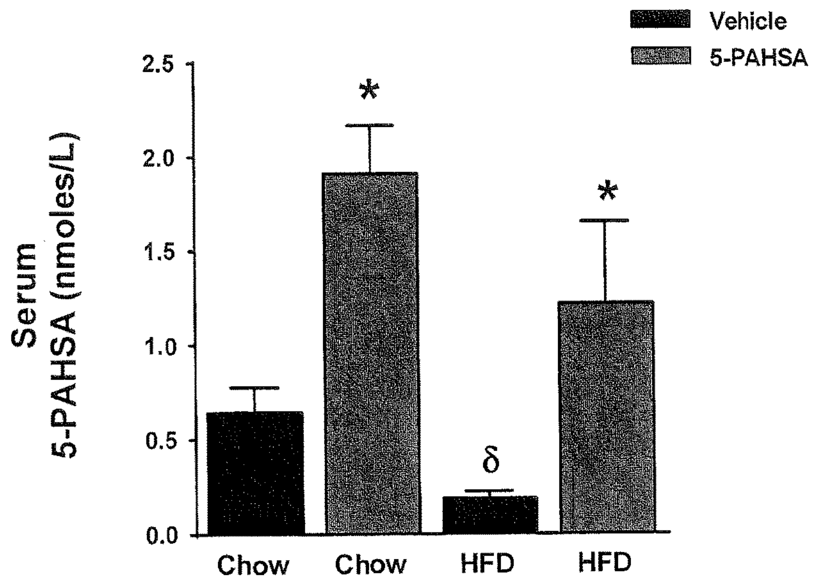

FIG. 56 is a bar graph showing serum 5-PAHSA levels after oral administration of synthesized 5-PAHSA. 3 h after food removal, mice were gavaged with 30 mg/kg body weight (chow-fed) or 45 mg/kg body weight (HFD-fed) of 5-PAHSA. 5 h post gavage, blood was collected via tail vein and serum 5-PAHSA was analyzed by mass spectrometry. n=3 mice per group. Data are expressed as mean±s.e.m. *p<0.05 vs. vehicle treated on the same diet; and δp<0.05 vs. chow vehicle.

FIGS. 57A and 57B are graphs showing GPR120 activation by 9-PAHSA and GPR120 knockdown in 3T3-L1 adipocytes. Specifically, FIG. 57A depicts a GPR120 activity assay using the PathHunter® eXpress GPR120L β-Arrestin GPCR Assay (DiscoverX). n=3 wells per condition. FIG. 57B is a bar graph showing validation of GPR120 knockdown in differentiated 3T3-L1 adipocytes. 3T3-L1 adipocytes (Day 8 post differentiation) were transfected with non-targeting (control) siRNA or three individual GPR120 targeting siRNA's individually or in combination. 48 h post-transfection GPR120 mRNA levels were measured by qPCR and normalized to TBP mRNA levels. n=3 wells per condition.

DETAILED DESCRIPTION OF THE INVENTION

The present invention provides methods for assessing the disease state and/or treatment response of a mammalian subject for a disease or disorder selected from obesity, type 2 diabetes (T2D), impaired glucose tolerance, maturity onset diabetes of the young (MODY), impaired fasting glucose, metabolic syndrome, insulin resistance, polycystic ovarian syndrome (PCOS), gestational diabetes, cardiovascular disease, inflammatory disorders, cancer, and other neoplastic disorders. To assess the disease state, a biological sample is obtained from the mammalian subject, and the level of one or more fatty acyl hydroxy fatty acids (FAHFAs) is determined. The invention also provides methods of treating the foregoing disorders, which, in particular embodiments, comprise administering an agent that increases the levels of one or more FAHFAs. The invention also provides isolated or purified preparations comprising FAHFAs.

I. Certain Definitions

As used herein, a "fatty acyl hydroxy fatty acid" or "FAHFA" means an estolide having an estolide number of 1, in which a hydroxy fatty acid is esterified at the hydroxyl group by another fatty acid. In the present invention, the hydroxyl group of the fatty acid is not on the terminal carbon of the fatty acid. A FAHFA may exist as a salt (e.g., a pharmaceutically acceptable salt, such as described below) or may be incorporated into other structures, including, but not limited to, phospholipids, glycerophospholipids, carbohydrates, polypeptides, proteins (e.g. analogues to cysteine palmitoylation and myristoylation), di- and triglycerides, and may be conjugates to CoA or acyl carnitine. In some embodiments, the terms "fatty acyl hydroxy fatty acid" or "FAHFA" also encompass any derivative according to the compound of Formula (I). FAHFAs within the scope of Formula (I) can be derivatized at one or more positions including the carboxylic moiety of the hydroxy fatty acid, the hydroxyl group, or the alkyl chain of the fatty acid, and can be derivatized by an oxygenated species, another heteroatomic species, or a hydrocarbon species.

"Estolide number" or "EN" is the number of fatty acid units added to the primary fatty acid.

All definitions of substituents set forth below are further applicable to the use of the term in conjunction with another substituent.

"Alkyl" means a saturated or unsaturated aliphatic branched or straight-chain hydrocarbon radical having the specified number of carbon atoms that can be substituted or unsubstituted. Thus, "$(C_1-C_6)$ alkyl" means a radical having from 1-6 carbon atoms in a linear or branched arrangement "$(C_1-C_6)$alkyl" includes methyl, ethyl, propyl, butyl, pentyl and hexyl. In some embodiments, "Alkyl" as used alone or as part of a larger moiety as in "arylalkyl" or "aryloxyalkyl" means a saturated aliphatic branched or straight-chain monovalent hydrocarbon radicals, for example, a radical having $C_1$-$C_{30}$ carbon atoms, in particular $C_{12}$-$C_{30}$, such as $C_{12}$-$C_{24}$, or alternately $C_1$-$C_{12}$ such as $C_1$-$C_6$.

"Alkylene" means a saturated aliphatic straight-chain divalent hydrocarbon radical. Thus, "$(C_1-C_6)$alkylene" means a divalent saturated aliphatic radical having from 1-6 carbon atoms in a linear arrangement. "$(C_1-C_6)$alkylene" includes methylene, ethylene, propylene, butylene, pentylene and hexylene.

"Heterocyclyl" means a saturated or partially unsaturated (3-7 membered) monocyclic heterocyclic ring containing one nitrogen atom and optionally 1 additional heteroatom independently selected from N, O or S. When one heteroatom is S, it can be optionally mono- or di-oxygenated (i.e., —S(O)— or —$S(O)_2$—). Examples of monocyclic heterocycle include, but not limited to, azetidine, pyrrolidine, piperidine, piperazine, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, or isothiazolidine 1,1-dioxide.

"Cycloalkyl" means saturated aliphatic cyclic hydrocarbon ring. Thus, "$C_3$-$C_8$ cycloalkyl" means (3-8 membered) saturated aliphatic cyclic hydrocarbon ring. $C_3$-$C_8$ cycloalkyl includes, but is not limited to, cyclopropyl, cyclobutyl, cyclopentyl, cyclohexyl, cycloheptyl, and cyclooctyl. Preferably, cycloalkyl is $C_3$-$C_6$ cycloalkyl.

The term "alkoxy" means —O-alkyl; "arylalkoxy" means an alkoxy group substituted at any carbon by an aryl group; "hydroxyalkyl" means alkyl substituted with hydroxy; "arylalkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)-A*, wherein A* is alkyl; "alkoxycarbonyl" means —C(O)—OA*, wherein A* is alkyl; and where alkyl is as defined above. Alkoxy is preferably $O(C_1-C_{12})$alkyl and includes methoxy, ethoxy, propoxy, butoxy, pentoxy and hexoxy.

"Cycloalkoxy" means an cycloalkyl-O— group wherein the cycloalkyl is as defined above. Exemplary $(C_3-C_7)$ cycloalkyloxy groups include cyclopropoxy, cyclobutoxy, cyclopentoxy, cyclohexoxy and cycloheptoxy.

"Hetero" refers to the replacement of at least one carbon atom member in a ring system with at least one heteroatom selected from N, S, and O. A hetero ring system may have 1 or 2 carbon atom members replaced by a heteroatom.

"Halogen" and "halo" are interchangeably used herein and each refers to fluorine, chlorine, bromine, or iodine.

"Cyano" means —C≡N.

"Nitro" means —$NO_2$.

As used herein, an amino group may be a primary (—$NH_2$), secondary (—$NHR_x$), or tertiary (—$NR_xR_y$), wherein $R_x$ and $R_y$ may be any alkyl, aryl, heterocyclyl, cycloalkyl or alkenylene, each optionally and independently substituted with one or more substituents described above. The $R_x$ and $R_y$ substituents may be taken together to form a "ring", wherein the "ring", as used herein, is cyclic amino groups such as piperidine and pyrrolidine, and may include heteroatoms such as in morpholine.

The terms "haloalkyl", "halocycloalkyl" and "haloalkoxy" mean alkyl, cycloalkyl, or alkoxy, as the case may be, substituted with one or more halogen atoms. The term "halogen" or "halo" means F, Cl, Br or I. Preferably the halogen in a haloalkyl or haloalkoxy is F.

The term "acyl group" means —C(O)B*, wherein B* is an optionally substituted alkyl group or aryl group (e.g., optionally substituted phenyl).

An "alkylene group" is represented by —$[CH_2]_z$—, wherein z is a positive integer, preferably from one to eight, more preferably from one to four.

An "alkenylene group" is an alkylene in which at least a pair of adjacent methylenes are replaced with —CH═CH—.

The term "$(C_6-C_{12})$aryl" used alone or as part of a larger moiety as in "arylalkyl", "arylalkoxy", "aryloxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-12 ring atoms. A "substituted aryl group" is substituted at any one or more substitutable ring atom. The term "$C_6$-$C_{12}$ aryl" as used herein means a monocyclic, bicyclic or tricyclic carbocyclic ring system containing from 6 to 12 carbon atoms and includes phenyl (Ph), naphthyl, 1,2-dihydronaphthyl, 1,2,3,4-tetrahydronaphthyl, fluorenyl, indanyl, indenyl and the like. The $(C_6-C_{10})$aryl$(C_1-C_6)$alkyl group connects to the rest of the molecule through the $(C_1-C_6)$alkyl portion of the $(C_6-C_{10})$aryl$(C_1-C_6)$alkyl group.

The term benzyl (Bn) refers to —$CH_2$Ph.

The term "heteroaryl", "heteroaromatic", "heteroaryl ring", "heteroaryl group" and "heteroaromatic group", used alone or as part of a larger moiety as in "heteroarylalkyl" or "heteroarylalkoxy", refers to aromatic ring groups having five to fourteen total ring atoms selected from carbon and at least one (typically 1-4, more typically 1 or 2) heteroatoms (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5 to 14 total atoms of which, unless otherwise specified, one, two, three, four or five are heteroatoms independently selected from N, NH, N($C_{1-6}$alkyl), O and S. ($C_5$-$C_{12}$)heteroaryl includes furyl, thiophenyl, pyridinyl, pyrrolyl, imidazolyl, and in preferred embodiments of the invention, heteroaryl is ($C_5$-$C_{12}$)heteroaryl.

The term "Alkenyl" means a straight or branched hydrocarbon radical having a specified number of carbon atoms and includes at least one double bond. In some embodiments, an alkenyl group has between 12 and 24 carbon atoms. The ($C_6$-$C_{10}$)aryl($C_{12}$-$C_{24}$)alkenyl group connects to the remainder of the molecule through the ($C_{12}$-$C_{24}$)alkenyl portion of ($C_6$-$C_{10}$)aryl($C_{12}$-$C_{24}$)alkenyl.

Salts, such as pharmaceutically acceptable salts, of the compounds of the present invention are also included. In particular embodiments, the salts of FAHFAs do not exist in nature, e.g., non-naturally-occurring salts of either naturally-occurring FAHFAs or non-naturally-occurring FAHFAs.

For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

A "subject" is a mammal, including primates (e.g., humans or monkeys), cows, sheep, goats, horses, dogs, cats, rabbits, guinea pigs, rats, mice or other bovine, ovine, equine, canine, feline, rodent or murine species. Examples of suitable subjects include, but are not limited to, human patients (e.g., obese, diabetic, non-diabetic, having a diabetes-related disorder, cancer or vascular disease) and in more particular embodiments human patients (e.g., obese, non-obese) who have, or are at risk for developing, a diabetes-related disorder, PCOS, an inflammatory disorder, vascular disease or cancer. Examples of high-risk groups for the development of PCOS, metabolic syndrome, insulin resistance or type 2 diabetes include medically overweight and obese individuals. In preferred embodiments, the subject is human. In particular embodiments, the subjects to be tested or treated by the methods provided by the invention have, or are at increased risk for developing obesity or a diabetes-related disorder, PCOS, an inflammatory disorder, cancer or vascular disease. In more particular embodiments, the vascular disease may be secondary to either obesity and/or a diabetes-related disorder. Similarly, the diabetes-related disorder may be secondary to obesity, or vice-versa. While subjects may be of any stage of life and any age, e.g., neonate, infant, toddler, child, young adult, adult, or geriatric; in particular embodiments the subject is an adult, e.g. a human adult, i.e. 18 years old, or older, e.g., 18-70, 20-60, 25-55, 25-50, 30-50, 25-65 years old, as well as greater than 30, 40, 50, 60, 70, 80 or 90 years old.

"Determining" a level of a FAHFA, requires contacting a sample (e.g. an isolated biological sample) with isolated analytic tools, such as laboratory equipment (e.g. a mass spectrometer) for measuring the level, and, in certain embodiments, additional isolated reagents, such as chemical solutions, isolated oligonucleotides (e.g. aptamers, optionally including a detectable label and/or non-natural functional groups), cloned enzymes, et cetera), antibodies (including antigen-binding fragments thereof; optionally where the antibody or antigen-binding fragment thereof is detectably labeled) to measure the level of a FAHFA by an analytical laboratory method. Reagents for determining a level of a FAHFA, in some embodiments, are products of man that do not exist in nature. Determining a level of a FAHFA may be done directly in the course of the analytical laboratory methods or, in some embodiments, by evaluating the quantitative output of the analytical laboratory methods.

As used herein, the terms "treat," "treating," or "treatment," mean to counteract a medical condition (e.g., obesity, a diabetes-related disorder, PCOS, an inflammatory disorder, cancer, vascular disease) to the extent that the medical condition is improved according to a clinically-acceptable standard. For example, an improvement in a medical condition related to obesity can be determined according to one or more of the following: 1) reduction of body weight, 2) reduction of body mass index (BMI), 3) reduction of waist-to-hip ratio (WHR); improvement relative to diabetes can include 1) improved glucose tolerance, 2) reduced glycated hemoglobin, 3) improved insulin sensitivity, 4) improved glycemia; improvement in PCOS can include: 1) increased fertility, 2) reduced ovary volume 3) resolution of hirsutism, 4) resolution of amenorrhea, 5) reduced levels of PSA; improvement in an inflammatory disorder can include: 1) reduced levels of pro-inflammatory cytokines, 2) increased levels of anti-inflammatory cytokines, 3) reduced pain, 4) reduced macrophage or dendritic cell counts at sites of inflammation; improvement in cancer can include: 1) reduced tumor growth, 2) tumor shrinking, 3) remission, 4) reduction in metastases, 5) reduced glucose uptake or utilization; improvement in vascular disease can include 1) reduced blood pressure, 2) lowered LDL cholesterol, 3) increased HDL cholesterol, 4) lowered triglycerides, 5) reduced atherosclerotic burden, 6) improved cardiac output. "Treatment response" is the change in a clinically-acceptable standard in response to a treatment, as defined above.

The terms "prevent," "preventing," or "prevention," as used herein, mean reducing the probability/likelihood, progression, onset, risk or severity of a disorder—including, for example, obesity or a diabetes-related disorder, PCOS, an inflammatory disorder, cancer or vascular disease—in a subject. In general, a subject undergoing a preventative regimen most likely will be categorized as being "at-risk" for a given disorder, e.g., the risk for the subject developing obesity, a diabetes-related condition, PCOS, an inflammatory disorder, vascular disease or cancer is higher than the risk for an individual represented by the relevant baseline population.

As used herein, a "therapeutically effective amount" is an amount sufficient to achieve the desired therapeutic or prophylactic effect under the conditions of administration, such as an amount sufficient to inhibit (e.g., reduce, prevent), e.g., obesity, diabetes-related disorder, vascular disease or cancer. The effectiveness of a therapy can be determined by one skilled in the art using standard measures and routine methods.

The term "obese" or "obesity" refers to the condition of a subject having a body mass index (BMI) of about 30 $kg/m^2$ or higher, e.g., a BMI of 25, 26, 27, 28, 29, 30, 31, 32, 33, 34, 35, 36, 37 $kg/m^2$, or more. In particular embodiments, an obese subject has a BMI within the ranges defined as "obese" by the Center for Disease Control. See, //www.cdc.gov/obesity/defining.html. For example, in some embodiments, an adult who has a BMI>=30.0 $kg/m^2$ is obese.

"Type 2 diabetes" or "T2D" (OMIM 125853), in some embodiments, is defined as provided by the World Health Organization and the International Diabetes Federation in "Definition and diagnosis of diabetes mellitus and intermediate hyperglycaemia," published in 2006, which is incorporated by reference in its entirety. In more particular embodiments, a diabetic subject exhibits a fasting plasma glucose of >=126 mg/dL or a 2-hour plasma glucose (2 hours after oral administration of 75 grams of glucose) >=200 mg/dL. In some embodiments a diabetic or pre-diabetic subject exhibits elevated levels of glycated hemoglobin, e.g., greater than 4.5, 4.6, 4.7, 4.8, 4.9, 5.0, 5.1, 5.2, 5.3, 5.4, 5.5, 5.6, 5.8, 6.0, 6.2, 6.4, 6.6., 6.8, 7.0, 7.2, 7.4, 7.6%, or more of total hemoglobin.

"Gestational diabetes" is a condition in which women without previously diagnosed diabetes exhibit high blood glucose levels during pregnancy, with a higher prevalence during the third trimester of pregnancy. Gestational diabetes typically resolves itself after pregnancy. In certain embodiments, gestational diabetes is classified as MODY 2.

"Insulin resistance," which may be identified by any means known in the art, and is characterized by a reduced ability of insulin to lower blood glucose levels.

The term "metabolic syndrome" refers to a group of symptoms that occur together and increase the risk for coronary artery disease, stroke and type 2 diabetes. In some embodiments the subject has central obesity (waist circumference>=80 cm for women; >=90 cm for Asian men, including ethnic South and Central Americans, and >=94 cm for all other males), BMI>30 $kg/m^2$, raised triglycerides (>=150 mg/dL, or specific treatment for this lipid abnormality), reduced HDL cholesterol (<40 mg/dL in males, <50 mg/dL in females or specific treatment for this lipid abnormality), raised blood pressure (sBP>=130 mm HG or dBP>=85 mm HG or treatment of previously diagnosed hypertension) or raised fasting plasma glucose (FPG>=100 mg/dL or previous type 2 diabetes diagnosis), including combinations thereof. In more particular embodiments, the subject to be treated by the methods provided by the invention has or is at increased risk for metabolic syndrome, as defined by the International Diabetes Federation in "The IDF consensus worldwide definition of the metabolic syndrome," published in 2006, which is incorporated by reference in its entirety, i.e., the subject has central obesity (as described above, and/or BMI>30 $kg/m^2$) AND any two of raised triglycerides, reduced HDL cholesterol, raised blood pressure, or raised fasting plasma glucose.

"Diabetes-related disorders" include T2D, gestational diabetes, MODY, impaired fasting glucose, impaired glucose tolerance, insulin resistance and metabolic syndrome.

"Cancer" refers to mammalian cancers, in some embodiments, human cancers, and carcinomas, sarcomas, adenocarcinomas, lymphomas, leukemias, et cetera, including solid and lymphoid cancers, kidney, breast, lung, kidney, bladder, colon, ovarian, prostate, pancreas, stomach, brain, head and neck, skin, uterine, testicular, esophagus, and liver cancer, including hepatocarcinoma, lymphoma, including non-Hodgkin's lymphomas (e.g., Burkitt's, Small Cell, and Large Cell lymphomas) and Hodgkin's lymphoma, leukemia, and multiple myeloma. Cancers embraced in the current application include both metastatic and non-metastatic cancers. In certain embodiments, a cancer cell may exhibit one or more of loss of contact inhibition when cultured, abnormal karyotype, abnormal cellular morphology or altered metabolic state consonant with what is termed the Warburg effect. Additional states that may be related to cancer and that can be diagnosed, monitored and/or treated by the methods provided by the invention include precancerous lesions and neoplasias.

"Vascular disease" is a pathological state of large, medium, or small sized arteries and may be triggered by endothelial cell dysfunction (e.g. including aneurisms, blockage, collapse) in central, peripheral or cerebral vasculature and can include angina, as well as severe complications such as stroke (ischemia), myocardial infarct (heart attack), arrhythmia, congestive heart failure, or ischemia resulting in gangrene or amputation.

"Polycystic ovarian syndrome" or "polycystic ovary syndrome" or "PCOS" is characterized by one or more of bilateral enlarged ovaries, abnormal 24-hour urinary ketosteroids, and evidence of virilization and, in particular embodiments, all three indications. In certain particular embodiments, PCOS is correlated with one or more of obesity, hirsutism, and amenorrhea, e.g., 1, 2, or all 3 indications. In other embodiments, a subject with PCOS exhibits elevated urinary levels of PSA (human GeneID No. 354) and/or kallikrein-2 (human GeneID No. 3817). In certain particular embodiments, PCOS is characterized by the presence of a mutation in any one of the loci identified in OMIM accession number 184700, which is incorporated by reference, including follistatin, CYP11A, CAPN10, or INSR (human GeneID No. 3643).

"Inflammatory disorders" are characterized by abnormally high levels of pro-inflammatory cytokines (e.g. IL-2, IL-3, GM-CSF, IL-6, IL-8, IL-18, HMGB1, TNF-$\alpha$, and IFN-$\gamma$) and/or abnormally low levels of anti-inflammatory cytokines (e.g. IL-10). Exemplary inflammatory disorders include sepsis, rheumatoid arthritis (RA), ulcerative colitis, inflammatory bowel disease, Crohn's disease, systemic lupus erythematosus, celiac disease, uveitis, pancreatitis, adult respiratory distress syndrome, asthma, multiple sclerosis, graft-versus host disease, atopic dermatitis, ankylosing spondylitis, and the like.

"Maturity onset diabetes of the young," "MODY," and the like are a group of disorders (see OMIM 606391, incorporated by reference)—autosomal dominants form of diabetes typically occurring before 25 years of age and caused by primary insulin secretion defects.

"Antibody" and the like refers to both whole immunoglobulins as well as antigen-binding fragments of immunoglobulins that contain an antigen-binding domain comprising at least 3, 4, 5, or 6 complementary determining regions (CDRs). Antibodies can be from any source including human, orangutan, mouse, rat, goat, sheep, rabbit and chicken antibodies, as well as synthetic, engineered antibodies. Antibodies may be polyclonal, monoclonal, monospecific, polyspecific, non-specific, humanized, camelized, single-chain, chimeric, synthetic, recombinant, hybrid, mutated, or CDR-grafted antibodies.

"Highly stringent hybridization" conditions refers to at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

II. FAHFAS

As noted above, in the present application a "fatty acyl hydroxy fatty acid" or "FAHFA" means an estolide having an estolide number of 1, in which a hydroxy fatty acid is esterified at the hydroxyl group by another fatty acid. In the present invention, the hydroxyl group of the fatty acid is not on the terminal carbon of the fatty acid. A FAHFA may exist as a salt or may be incorporated into other structures, including, but not limited to, phospholipids, glycerophospholipids, carbohydrates, polypeptides, proteins (e.g. analogous to cysteine palmitoylation and myristoylation), di- and triglycerides, and may be conjugated to other molecules involved in metabolism, particularly lipid metabolism, such as CoA or acyl carnitine.

In certain embodiments, FAHFAs and the like are estolides comprising a hydroxy fatty acid that is esterified at the hydroxyl group by a fatty acid. The FAHFAs provided by the invention are, in certain embodiments, structures of formula (I).

(I)

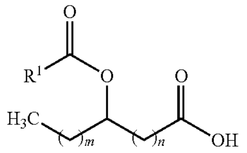

wherein: m is an integer from 0 to 21;

n is an integer from 0 to 21;

the sum of m and n is an integer from 11 to 21; and $R^1$ is an alkyl group.

In some embodiments of the invention, the FAHFA may exist as a salt or may be incorporated into other structures, including, but not limited to, phospholipids, glycerophospholipids, carbohydrates, polypeptides and proteins, di- and triglycerides, and other metabolic co-factors such as CoA or acyl carnitine.

In certain embodiments of the invention, the base unit of the FAHFA, the hydroxy fatty acid, is hydroxytetradecanoic acid (14 carbon atoms), hydroxypentadecanoic acid (15 carbon atoms), hydroxypalmitic acid (16 carbon atoms), hydroxyheptadecanoic acid (17 carbon atoms), hydroxystearic acid (18 carbon atoms), hydroxynonadecylic acid (19 carbon atoms), hydroxyicosanoic acid (20 carbon atoms), hydroxyhenicosanoic acid (21 carbon atoms), hydroxydocosanoic acid (22 carbon atoms), hydroxytricosanoic acid (23 carbon atoms), or hydroxytetracosanoic acid (24 carbon atoms), where, for each of the above, the hydroxyl group may substitute any of positions 2 through p−1, where p is the total number of carbons in the fatty acid. The fatty acid ester can be a saturated or unsaturated, linear or branched ($C_1$-$C_{23}$) alkyl group.

In particular embodiments, $R^1$ is a $C_{15}$ residue derived from palmitic acid, a $C_{16}$ residue derived from margaric acid, a $C_{17}$ residue derived from stearic acid, or an unsaturated $C_{17}$ residue derived from oleic acid.

In a more particular embodiment of the invention, the FAHFA is 9-PAHSA, and is 9-hydroxystearic acid esterified with palmitic acid. In the case of 9-PAHSA, m=8, n=7, and $R^1$ is $C_{15}H_{31}$ in formula (I). In another particular embodiment of the invention, the FAHFA is 5-hydroxystearic acid esterified with palmitic acid (5-PAHSA). In the case of 5-PAHSA, m=12, n=3, and $R^1$ is $C_{15}H_{31}$ in formula (I).

The present invention also discloses a method to identify specific protein-metabolite interactions through the synthesis of FAHFA derivatives, such as detectably labeled FAHFAs. For example, in some embodiments, FAHFAs are isotopically labeled and/or ester- or amide-bound to a detectable moiety, such as streptavidin, GST, an epitope tag such as FLAG, 6× His, or another affinity tag. In certain embodiments of the invention, the FAHFA is fluorinated for use in fluorous affinity chromatography, or bound to an alkyne for use with click chemistry. In a particular embodiment, FAHFAs are biotinylated FAHFAs. Because biotin binds tightly to strepavidin protein (e.g. immobilized strepavidin), the biotinylated FAHFA may be used in "pull down" assays that enable the identification of FAHFA binding partners, such a FAHFA-binding proteins. The FAHFA is biotinylated through an amide or ester linkage. In certain embodiments of the invention, the carboxylic acid of the FAHFA is amidated with a biotinylated alkyl amine (FIG. 14).

In a particular embodiment, hydroxyl group of the FAHFA is amidated and acylated with a biotin derivative. 9-hydroxystearic acid is protected as the ester with 2,4'-dibromoacetophenone. The product is mesylated with mesyl chloride, then the mesyl group is displaced by sodium azide. The azide is reduced with zinc dust in acetic acid to afford the aminated fatty acid. The amine is then acylated with a biotin derivative to afford a biotinylated FAHFA, as in Scheme 1.

Scheme 1.

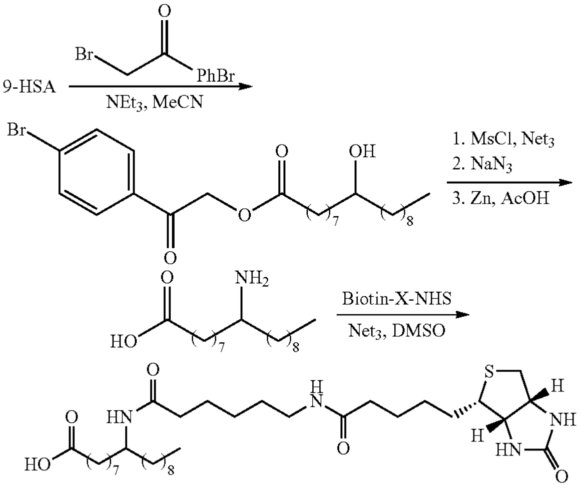

Biotin-X-9-HSA

III. Diagnostic Methods, Antibodies and Kits

The invention provides a variety of methods for the diagnosis, prognosis, and monitoring (e.g. disease progression and/or treatment efficacy) for a variety of disorders by determining the level of one or more FAHFAs in a biological sample from a subject and, e.g., comparing the level of the one or more levels to suitable controls, such as annotated reference values for a particular disease or disorder, as well as monitoring them over time in a subject. Accordingly, the invention also provides kits and antibodies for performing these methods.

For the diagnostic, prognostic, or monitoring methods provided by the invention, the one or more FAHFAs can be detected by measuring the level of precursors (such as a hydroxyl fatty acid), metabolites, or derivatives of the one or more FAHFAs. The one or more FAHFAs—or precursor, metabolite, or derivative thereof—need only be detected at resolution at which they are distinguishable from other molecules in the given biological sample (or derived fraction thereof), such as plasma, serum, total lipids, et cetera.

As defined above, any mammalian subject can be evaluated by the methods of the invention, while human subjects are one particular exemplification. Also, the subject may be of any age, with adult human subjects serving as particular exemplifications. However veterinary applications, particularly in a research context to develop treatments for human subjects are clearly encompassed by the invention as well.

Samples for use in the methods provided by the invention include any suitable biological sample or fraction thereof (e.g., extracted total lipids or further subfractions thereof). In particular embodiments, the biological sample may be isolated from blood (e.g. serum or plasma), liver, adipose tissue, brown adipose tissue, muscle, pancreas, islet cells, kidney, breast, small intestine, bone marrow, nervous tissue (central, including brain or spine, and/or peripheral), ovary, or prostate. In some embodiments, the biological sample includes cancerous, precancerous, or neoplastic tissue that may include tissue obtained from any of the foregoing tissues. In more particular embodiments, the biological sample comprises serum, plasma, liver or adipose tissue. Biological samples may be assayed from fresh or fixed (or otherwise preserved) samples.

The classification of a sample as normal (or well-controlled) or associated with a disease state (and/or requiring a modified treatment protocol) depends on the particular indication being assayed for (e.g., cancer versus obesity and diabetes-related disorders, including, in some embodiments, associated vascular disease). For example, in adipose tissue, levels of FAHFAs are negatively correlated with disease state—i.e. reduced levels FAHFAs in adipose tissue are associated with disease states such as diabetes-related disorders.

Levels of FAHFAs can be determined by any means known in the art, including tandem mass spectrometry (MS/MS) and in particular embodiments, MS/MS with multiple reaction monitoring (MRM). Additional detection methods include HPLC (high precision liquid chromatography; optionally coupled to MS/MS, with or without MRM), TLC (thin layer chromatography), NMR (Nuclear Magnetic Resonance) spectroscopy, IR (Infrared) spectroscopy, UV-VIS spectroscopy, GC (gas chromatography, optionally coupling to MS/MS), and capillary electrophoresis. Further detection methods include immune-methods employing antibodies that specifically bind to FAHFAs, including polyacrylimide electrophoresis, RIA, ELISA et cetera; nucleic acid-based or protein-based aptamer techniques), SPR (surface plasmon resonance), and SAT (suspension array technology—including both immune-based, aptamer-based, or combination methods).

Levels of one or more FAHFAs can be evaluated and classified by a variety of means such as general linear model (GLM), ANOVA, regression (including logistic regression), support vector machines (SVM), linear discriminant analysis (LDA), principal component analysis (PCA), k-nearest neighbor (kNN), neural network (NN), nearest mean/centroid (NM), and bayesian covariate predictor (BCP). Suitable cutoffs for evaluating levels of one or more FAHFAs (e.g., for classification as abnormal (obese; positive or at risks for a diabetes-related disorder, cancer, PCOS, an inflammatory disorder, or vascular disease; requiring modification of a treatment regime) or normal (or low risk, or positive response to treatment) can be determined using routine methods, such as ROC (receiver operating characteristic) analysis, and may be adjusted to achieve the desired sensitivity (e.g., at least about 50, 52, 55, 57, 60, 62, 65, 67, 70, 72, 75, 77, 80, 82, 85, 87, 90, 92, 95, 97, or 99% sensitivity) and specificity (e.g., at least about 50, 52, 55, 57, 60, 62, 65, 67, 70, 72, 75, 77, 80, 82, 85, 87, 90, 92, 95, 97, or 99% specificity).

For example, in particular embodiments, levels of one or more FAHFAs are converted to a disease index. In particular embodiments, a disease index can use raw or transformed (e.g. normalized to any suitable metabolite, log-normalized, percentile ranked, ranked as quartiles, et cetera) levels of FAHFAs. A disease index for a particular individual can be compared to reference values as, for example, a percentile rank. Using percentile ranks the skilled artisan can then diagnose, prognose, or otherwise clinically stratify a subject by comparing the subject's disease index to these reference values. For example, in certain embodiments, a subject with a disease index percentile rank of at least 40, 45, 50, 60, 65, 70, 75, 80, 85, 90, or 95 may be classified as having, being at an increased risk for developing, or needing additional/alternative treatment for obesity, a diabetes-related disorder, cancer, PCOS, an inflammatory disorder, or vascular disease. In more particular embodiments, a subject exhibiting a disease index in at least the $60^{th}$, e.g., at least $70^{th}$ or at least $75^{th}$ percentile is classified as having, being at an increased risk for developing, or needing additional/alternative treatment for obesity, a diabetes-related disorder, PCOS, an inflammatory disorder, cancer or vascular disease. A selected threshold for a disease index can be set to achieve a desired sensitivity or specificity, as described above, and/or to stratify subjects based on a relative hazard ratio between stratification groups. For example, in some embodiments, a disease index threshold is set to achieve a "hazard ratio" (ratio of frequency of a disorder between two stratification groups, e.g., high and low risk of disease or complication) of about 1.1, 1.2, 1.4, 1.6, 1.8, 2.0, 2.2, 2.4, 2.5, 2.6, 2.8, 3.0, 3.5, 4.0, or more. In more particular embodiments, the index threshold is set to achieve a hazard ratio of at least about 3.8, 3.9, 4.0, 4.1, 4.2, 4.3, 4.4, or more, e.g., 5, 6, 7, 8, 9, or 10. "Stratification groups" are the groups of a data set satisfying one or more stratification criteria—for example, a percentile rank of disease index, such as all group members with a disease index greater than or equal to the $60^{th}$ percentile. Stratification groups may be compared by any means by any statistic, such as, mean, median, mode, and/or standard deviation of any clinical parameter, such as age, duration of disease, frequency of death, et cetera.

Kits provided by the invention contain reagents to perform any of the methods provided by the invention, e.g. antibodies or other reagents to detect one or more FAHFAs, as described above. In particular embodiments, the kits include instructions for use. Optionally, the kits may include "suitable positive controls," which are compositions comprising (consisting essentially of, or consisting of) lipids that contain known concentrations of one or more FAHFAs. For example, suitable controls may be from a clinical source known to have obesity, a diabetes-related disorder, PCOS, an inflammatory disorder, cancer or vascular disease and may include either fixed or preserved but otherwise unprocessed biological sample, or, alternatively, isolated fractions from such samples, including fractions comprising (consisting of or consisting essentially of) lipids (e.g., at least 20, 40, 50, 60, 70, 80, 90, 95, 97, 99% by dry weight, or more, lipids). Alternatively, in certain embodiments, the suitable positive controls may comprise artificial mixtures of lipids, e.g., combined in proportions characteristic of an abnormal levels of one or more FAHFAs for a particular disorder and/or particular ranges of concentrations.

IV. Treatment Methods

In another aspect, the invention provides methods of treatment comprising administering a suitable prophylaxis or treatment to a subject in need thereof, as determined by the methods provided by the invention—e.g., according to any of the methods described under the previous subheading. Specifically, in certain embodiments, the subject is administered any clinically acceptable prophylaxis or treatment (including new regimens or modifications of existing regimens) for their given indication, based on the determination that the subject exhibits an abnormal level of one or more FAHFAs according to the methods provided by the invention. In more particular embodiments, any of the methods described in the claims or under the previous subheading further comprise the steps of follow-on diagnosis, prognosis or treatment. In other embodiments, the follow-on diagnosis, prognosis or treatment is performed by a provider advised of the presence of an abnormal level of one or more FAHFAs, but who did not necessarily make the determination. For example, where the subject has been identified as having, being at an increased risk for, or needing further treatment for obesity, a diabetes-related disorder, PCOS, an inflammatory disorder, cancer or vascular disease, at least in part, on the basis of abnormal levels of one or more FAHFAs, a provider administers or directs the subject to undergo a prophylactic and/or treatment regime (or a change in an existing treatment) suitable for the indication.

Suitable prophylaxes or treatments for diabetes-related disorders include, for example, weight loss programs, increased exercise, modified diet (e.g., reduced glycemic index), GLP-1R (human GeneID 2740) agonists (such as exenatide and liraglutide); DPP-4 antagonists (e.g., saxagliptin, vildagliptin); pramlintide; insulins (e.g., glulisine, detemir, glargine, lispro, aspart); SGLT2 (human GeneID No. 6524) inhibitors; inhibitors of glucose synthesis or release (FR-225654, CS-917 and MB07803; including starch blockers, such as acarbose); inhibitors of pyruvate kinase M2 (human GeneID No. 5315) (including agents described in U.S. Patent Application Publication No. 20100099726 A1, incorporated by reference in its entirety); insulin sensitizers (such as biguanidines, including metformin); adiponectin receptor 1 (human GeneID No. 51094) and adiponectin receptor 2 (human GeneID No. 79602) agonists; leptin receptor (human GeneID No. 3953) agonists; anoretics (e.g., sibutramine, rimonabant, bupropion); and the like, including combinations of the foregoing.

Suitable prophylaxes or treatments for obesity include weight loss programs, increased exercise, modified diet (e.g. reduced caloric, carbohydrate, or fat diets), gastric bypass or laproscopic banding, SGLT2 (human GeneID No. 6524) inhibitors; inhibitors of glucose synthesis or release (SB-204990, 2-deoxy-D-glucose (2DG), 3-bromopyruvate (3-BrPA, Bromopyruvic acid, or bromopyruvate), 3-BrOP, 5-thioglucose and dichloroacetic acid (DCA), FR-225654, CS-917 and MB07803); inhibitors of pyruvate kinase M2 (human GeneID No. 5315) (including agents described in U.S. Patent Application Publication No. 20100099726 A1, incorporated by reference in its entirety); leptin receptor (human GeneID No. 3953) agonists; anoretics (e.g., sibutramine, rimonabant, bupropion); fat absorption inhibitors (such as orlistat); and the like, including combinations of the foregoing.

Suitable prophylaxes or treatments for cancer include chemotherapy, hormonal therapy, immunotherapy, radiotherapy, surgery, targeted gene therapies (e.g., epidermal growth factor receptor-tyrosine kinase inhibitors, such as gefitinib; and agents targeting ALK mutations and rearrangements, such as crizotinib, et cetera), glycolytic inhibitors (e.g., SB-204990, 2DG, 3-BrOP, 5-thioglucose, DCA, as well as those agents described in U.S. Patent Application Publication No. 20100099726 A1), inhibitors of ATP-citrate lyase, inhibitors acetyl-CoA carboxylase, inhibitors fatty acid synthase, and combinations of the foregoing.

Suitable prophylaxes or treatments for vascular disease include weight loss programs (such as the pharmaceutical obesity treatments, above), increased exercise, modified diet (e.g. reduced salt), statin treatment (e.g. atorvastatin, fluvastatin, lovastatin, pitavastatin, pravastatin, rosuvastatin and simvastatin), bypass surgery and stenting; as well as combinations of the foregoing.

Suitable prophylaxes or treatments for PCOS include weight loss, hormonal therapy (e.g. birth control pills, progesterone), meformin, LH-releasing hormone analogs, thiazolidinediones, and cyproterone or spironolactone (or other antiandrogen), and clomifene (or other selective estrogen receptor modulator), including combinations of the foregoing.

Suitable prophylaxes or treatments for inflammatory disorders include immunomodulators, including immunosuppressants, such as methotrexate or steroids; NSAIDs; COX-2 inhibitors (coxibs); neutralizing antibodies directed to a pro-inflammatory cytokine; a soluble receptor for a pro-inflammatory cytokine; or exogenous anti-inflammatory cytokines, as well as agents that increase the levels of anti-inflammatory cytokines, e.g., at either the nucleic acid or protein level; including combinations of the above.

It is, of course, encompassed by the methods provided by the invention that a subject determined to have obesity, a diabetes-related disorder, PCOS, an inflammatory disorder, cancer or vascular disease may have one or more of these disorders, e.g. 2, 3 or 4 or more of these disorders, and may therefore provide an indication for treatment with combinations of prophylaxes or treatments for the different disorders, i.e. combinations of prophylaxes or treatments for obesity, a diabetes-related disorder, PCOS, an inflammatory disorder, cancer or vascular disease as described above.

In another aspect, the invention provides methods of treating a subject with any one or more of obesity, a diabetes-related disorder, PCOS, an inflammatory disorder, cancer or vascular disease, comprising administering to the subject a therapeutically effective amount of one or more agents that increase the level of one or more FAHFAs. In particular embodiments, the agent that increases the level of one or more FAHFAs is one or more exogenous FAHFAs—i.e., one or more of any of the FAHFAs described herein, e.g., a composition comprising 1, 2, 3, 4, 5, 6, 7, 8, 9, 10, or more FAHFA species. For example, in particular embodiments, the composition comprises 5-PAHSA and/or 9-PAHSA. In certain embodiments the one or more FAHFAs administered to the subject are detectably labeled, as described above.

In other embodiments, the agent that increases the level of one or more FAHFAs is an inhibitor (antagonist or negative agonist) of carboxyl ester lipase (CEL) (human GeneID No. 1056). Inhibitors of CEL include siRNAs (e.g., which target a mRNA at least 60%, e.g., 60, 65, 70, 75, 80, 85, 90, 95, 96, 97, 98, 99, or 100% identical to NM_001807, or a fragment thereof, e.g., a contiguous fragment of at least 20, 25, 30, 35, 40, 45, 50, 100, 200, 300, 400, 500, 1000, 1500, 2000, or 2384 bp of any of the foregoing; or a nucleic acid that hybridizes under highly stringent hybridization conditions to any of the foregoing); neutralizing antibodies (e.g., which specifically bind to polypeptide comprising an amino acid sequence at least 60%, e.g., 60, 65, 70, 75, 80, 85, 90, 95, 96, 97, 98, 99, or 100% identical to NP 001798, or a fragment thereof, e.g., a contiguous fragment of at least 5, 10, 20, 25, 30, 35, 40, 45, 50, 100, 200, 300, 400, 500, 600, 700, or 756 amino acids of any of the foregoing; in particular embodiments the antibody specifically binds a portion of CEL comprising one of the amino acid residues of the catalytic triad (see conserved domain cd00312; e.g. S217, D343, and H458 of NP_001798) or substrate binding pocket (see conserved domain cd00312); an aptamer (e.g. polypeptide or nucleic acid, including analogs of either) directed to the catalytic triad or substrate binding pocket of CEL, as exemplified above; or any of the compounds described in U.S. Patent Application Publication No. 20100324075, or U.S. Pat. Nos. 5,391,571; 5,512,565; 5,942,631; 6,034,255; 6,114,545 5,017,565; and 5,063,210, which are incorporated by reference; as well as natural, non-FAHFA substrates of CEL, which act as competitive inhibitors; and combinations of any of the foregoing.

In different embodiments, the agent that increases FAHFA levels is a ChREBP expression product, such as a ChREBP α expression product, a ChREBP β expression product, or a combination of ChREBP α and β expression products, (collectively "ChREBP expression products") as further described in U.S. Provisional Application No. 61/590,012, filed Jan. 24, 2012, which is incorporated by reference in its entirety. "ChREBP β expression product" or simply "ChREBP β" is a nucleic acid encoding an N-terminally truncated isoform of ChREBP that exhibits enhanced transcriptional activation relative to ChREBP protein that is not N-terminally truncated—termed "ChREBP α," here; "ChREBP β" and "ChREBP β expression product" also encompasses a protein expression product encoded by a nucleic acid that encodes an N-terminally truncated isoform of ChREBP that exhibits enhanced transcriptional activation relative to ChREBP α. The ChREBP expression products for use in the inventions can be either recombinant or non-recombinant. In a particular embodiment, ChREBP α is exemplified by the reference sequence NP_116569, and encompasses proteins comprising an amino acid sequence at least 60, 65, 70, 75, 80, 85, 90, 95, 96, 97, 98, 99, or 100% identical to this reference sequence. In some embodiments a ChREBP β expression product has (or, in the case of a nucleic acid, encodes) an N-terminal truncation, relative to ChREBP α, of at least about 10, 20, 30, 40, 50, 75, 100, 125, 150, 170, 171, 172, 173, 174, 175, 176, 177, 178, 179, or 180 amino acids. In certain embodiments, the ChREBP β expression product is encoded by a transcript lacking the first exon of a ChREBP transcript encoding a ChREBP α protein (such as the reference sequence NM_032951.2, as well as nucleic acids at least 60, 65, 70, 75, 80, 85, 90, 95, 96, 97, 98, 99, or 100% identical to this reference sequence or that hybridize to its complement under highly stringent hybridization conditions). In more particular embodiments, a ChREBP β expression product is encoded by a transcript comprising an alternative first exon, termed "exon 1b" herein, preferably wherein the exon 1b does not encode protein sequence. ChREBP expression products will typically retain the function of structurally conserved regions, including those depicted in FIG. 18 of Application No. 61/590,012 and, in more preferred embodiments, which preserve the function of the "P2" domain depicted in Li et al. 2006 (see FIG. 2 in Li, which is incorporated herein by reference, and is contained within the GRACE domain), which is required for ChREBP function.

In other embodiments, an agent that increases the level of one or more FAHFA is a PPAR agonist, such as an agonist of PPAR α (human GeneID No. 5465), PPAR γ (human GeneID No. 5468), or PPAR δ (human GeneID No. 5467) activity, and in particular embodiments, PPAR the PPAR agonist is WY14643, CAY10592, or Pioglitazone or other thiazolediendiones including rosiglitazone, troglitazone or other PPAR gamma agonists, or any of the agents described in Kahn and McGraw *N. Engl. J. Med.* 363(27):2667-9 (2010) or paragraph 301 of U.S. Patent Application Publication No. 20120052040, which are incorporated by reference in their entirety. In the examples of the present application, Applicants show that levels of the 5 PAHFA are highest in liver and brown fat and increase in serum and liver with fasting. PPAR α is a master metabolic regulator of the fasting state and in the liver upregulates FA oxidation, enhancing ketogenesis. PPAR α is also critical for FA oxidation required for BAT (brown adipose tissue) thermogenesis. The data in this application indicates that circulating 5 FAHFA levels are regulated in a PPAR α dependent manner. These data suggest that the 5 FAHFA might be important for mediating biological actions of PPAR α activation. In the liver, this may include activating FA oxidation which may be therapeutically useful for treating fatty liver disease. Increasing FA oxidation in BAT may enhance thermogenesis and whole-body energy expenditure which may help treat obesity and obesity associated metabolic diseases. 5 FAHFA may be one means by which BAT affects systemic metabolic controls.

The one or more agents that increase the level of one or more FAHFA is administered in a therapeutically effective amount to the subject, in any suitable formulation and by any suitably mode of administration. Suitable modes of administration include e.g., intra venous, or intra peritoneal, rectal, oral or nasal administration, with oral being a particular mode of administration. Appropriate formulations include tablets, gelcaps, syrups, oil mixtures, emulsions, et cetera. For example, oil mixtures include preparing the FAHFA in a formulation with a pharmaceutical or dietary oil, for example, in a gelcap or as a dietary supplement in cooking oil, salad oil, or in a dropper formulation for direct oral administration or mixing in, e.g., yogurt, milk, et cetera. In certain embodiments, the agent that increases FAHFA levels is e.g., supported by a solid carrier, such as starch, dextrose, yeast extract, wheat germ, et cetera, for sprinkling onto food. In other embodiments, one or more FAHFAs are delivered by slow release subcutaneous pellets or infrequent subcutaneous depot injection with release over months.

In other aspects, the invention provides methods of decreasing pro-inflammatory signaling or increasing: glucose uptake, glucose tolerance, insulin secretion, or insulin sensitivity in either an isolated cell or in a subject. These methods comprise contacting the cell, or administering to the subject, an agent that increases the level of one or more FAHFAs, as described, above. In particular embodiments, these methods comprise contacting the cell with one or more FAHFAs alone or in combination with any of the foregoing agents that increase the levels of one or more FAHFAs, e.g., a CEL antagonist, a ChREBP expression product, or a PPAR agonist.

V. Screening Methods

In another aspect, the invention provides screening methods for identifying an agent that modulates FAHFA levels. The methods comprise determining the level of one or more FAHFAs in a cell contacted with a candidate agent, where a change in the level of one or more FAHFAs in the cell relative to a control cell not contacted with the agent indicates that the agent modulates the level of one or more FAHFAs.

Any cell type may be useful in such methods including, yeast or insect cells, or a mammalian cell, e.g. a primate, murine, bovine, ovine, leporine, or porcine cell. The cell may be isolated, e.g., the method is performed in vitro, in a suitable culture, e.g., with either primary or established cell lines. Suitable cells include macrophages (such as a RAW cell), islet cells (such as the Ins1 cell line), or a hepatic cell (such as HepG2 cells). In some embodiments, the cells are recombinant while in other embodiments the cells are non-recombinant. In other embodiments, the cell is in situ, i.e., the method is performed in vivo in a non-human animal, and in more particular embodiments in a non-human mammal, such as a non-human primate, a leporine or murine. The non-human animal may be transgenic or non-transgenic and such animals may also serve as the source of cells for the in vitro screening methods provided by the invention. In particular embodiments, the non-human mammal is a mouse and in more particular embodiments is an AG4OX mouse, an AG4KO mouse, a ChREBPKO mouse, or a ChREBPOX mouse.

In some embodiments, the cell expresses ChREBP and, in particular embodiments, overexpress ChREBP α or β, and in still more particular embodiments, overexpress ChREBP α or β in adipose tissue. In other embodiments, the cell may express reduced levels of ChREBP α or β or express a hypomorphic or dominant negative form of ChREBP or a dominant negative form of its dimerization partner Mlx (human GeneID No. 6945), and in still more particular embodiments, the cell may be a ChREBP or Mlx knockout (ChREBPKO or MlxKO). In other embodiments, the cell expresses GLUT4 (SLC2A4, human GeneID No. 6517), and in more particular embodiments overexpresses GLUT4 and in still more particular embodiments, overexpresses GLUT4 in adipose tissue (AG4OX). In other embodiments, the cell may express reduced levels of GLUT4 or express a hypomorphic or dominant negative form of GLUT4 and in still more particular embodiments, the cell may be a GLUT4 knockout (GLUT4KO) or more particularly, a knockout in adipose tissue only, AG4KO).

The cell, in certain embodiments, further expresses Mlx. In other embodiments, the cell further expresses GLUT4 and in more particular embodiments, the cell further expresses both Mlx and GLUT4. Although not essential to all aspects of these screening methods, in some embodiments, the methods include incubating the cell in the presence of glucose or fructose or their metabolites or analogs such as glucose-6-phosphate, xyulose-5-phosphate, fructose-2,6-bisphosphate, mannoheptulose, 2-deoxyglucose (2DG), or fluorodeoxyglucose. In other embodiments, the cell is incubated in low glucose conditions (e.g. the cell is cultured in low glucose conditions or the non-human mammal is maintained on a low carbohydrate diet). For example, in particular embodiments, the cell is cultured in <25 mM glucose, e.g. less than 10 or 5 mM glucose, e.g. about 1-5 mM, 2-3 mM, or 2.5 mM glucose.

The screening methods provided by the invention can, in some embodiments, include screening the candidate agent in the presence of additional agents, e.g., a second (or more) candidate therapeutic. For example, second therapeutic agents can include one or more of any of the therapeutics described under the previous subheading in order to identify combinations of agents with synergistic interactions. In other embodiments, the cell is contacted with a modulator of PPAR α (human GeneID No. 5465), PPAR γ (human GeneID No. 5468), or PPAR δ (human GeneID No. 5467) activity, and in particular embodiments, PPAR agonists, such as WY14643, CAY10592, or Pioglitazone. Agents identified by these screening methods may either increase or decrease the level of one or more FAHFAs. Methods of treating obesity, a diabetes-related disorder, PCOS, an inflammatory disorder, cancer or vascular disease by administering an effective amount of one or more of the agents identified by these screening methods are contemplated and encompassed by the present invention.

VI. FAHFAs and Derivatives Thereof

As noted above, in the present application a "fatty acyl hydroxy fatty acid" or "FAHFA" means an estolide having an estolide number of 1, in which a hydroxy fatty acid is esterified at the hydroxyl group by another fatty acid, and also means any derivative according to the compound of Formula (I). FAHFAs within the scope of Formula (I) can be derivatized at one or more positions including the carboxylic moiety of the hydroxy fatty acid, the hydroxyl group, or the alkyl chain of the fatty acid, and can be derivatized by an oxygenated species, another heteroatomic species, or a hydrocarbon species. In the present invention, the hydroxyl group of the fatty acid is not on the terminal carbon of the fatty acid. A FAHFA may exist as a salt or may be incorporated into other structures, including, but not limited to, phospholipids, glycerophospholipids, carbohydrates, polypeptides, proteins (e.g. analogous to cysteine palmitoylation and myristoylation), di- and triglycerides, and may be conjugated to other molecules involved in metabolism, particularly lipid metabolism, such as CoA or acyl carnitine.

In certain embodiments of the invention, isolated fatty acyl hydroxy fatty acids (FAHFAs) and derivatives thereof are structures of Formula (III):

(III)

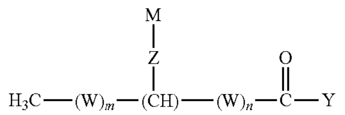

or a salt thereof, wherein:

m is an integer from 0 to 21;

n is an integer from 0 to 21;

the sum of m and n is an integer from 11 to 21;

W, for each occurrence, is independently $(CR^1R^2)$ or $(C(R^3){=}C(R^4))$;

Z is —NH(CO)—, —O—, —O(CO)—, —S—, —NH—, —NO—, —O(CO)O—, —O(CO)NH—, —NH(CO)O—, —$SO_2$—, —OP(O)($OR^{11}$)O—, —Se—, —SeO—, —N($R^{11}$)—, or —O(CO)N($R^{11}$)—;

Y is H, OH, $OR^5$, $NHR^6$, $N(R^7)_2$, $SR^8$, or halo;

$R^1$, $R^2$, $R^3$ and $R^4$ for each occurrence, are independently selected from H, $(C_6\text{-}C_{12})$aryl, $(C_5\text{-}C_{12})$heteroaryl, —(CO)$(C_1\text{-}C_6)$alkyl, $(C_1\text{-}C_{12})$alkyl, $(C_1\text{-}C_{12})$alkoxy, or hydroxyl;

M is selected from $(CR^9R^{10})_{11\text{-}23}CH_3$, $(C_6\text{-}C_{12})$aryl, $(C_5\text{-}C_{12})$heteroaryl, or $(C_{12}\text{-}C_{24})$alkenyl, wherein each $(C_6\text{-}C_{12})$aryl, $(C_5\text{-}C_{12})$heteroaryl, and $(C_{12}\text{-}C_{24})$alkenyl is optionally and independently substituted at any one or more substitutable positions by $(C_1\text{-}C_{12})$alkyl, $(C_1\text{-}C_{12})$alkoxy, hydroxyl, —$NH_2$, —$N((C_1\text{-}C_{12})alkyl)_2$, or —S—$(C_1\text{-}C_{12})$alkyl;

$R^5$, $R^6$, $R^7$, and $R^8$ are each $(C_1\text{-}C_{12})$alkyl, $(C_6\text{-}C_{12})$aryl, $(C_5\text{-}C_{12})$heteroaryl, or $(C_{12}\text{-}C_{24})$alkenyl;

$R^9$ and $R^{10}$, for each occurrence, are H, $(C_1\text{-}C_{12})$alkyl, $(C_1\text{-}C_{12})$alkoxy, hydroxyl, —$NH_2$, —$N[(C_1\text{-}C_{12})alkyl]_2$, or —$S(C_1\text{-}C_{12})$alkyl;

provided that:

when any one of $R^1$ or $R^2$ is hydroxyl or $(C_1\text{-}C_{12})$alkoxy, then not all $R^9$ and $R^{10}$ are H;

when any one of $R^9$ or $R^{10}$ is hydroxyl or $(C_1\text{-}C_{12})$alkoxy, then not all $R^1$ and are H; and $(C_{12}\text{-}C_{24})$alkenyl is not $(C_{17})$alkenyl or $(C_{19})$alkenyl.

In further embodiments of the invention, isolated fatty acyl hydroxy fatty acids (FAHFAs) and derivatives thereof are structures of Formula (IV):

(IV)

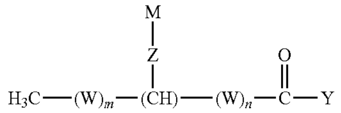

or a salt thereof, wherein:

m is an integer from 0 to 21;

n is an integer from 0 to 21;

the sum of m and n is an integer from 11 to 21;

W, for each occurrence, is independently $(CR^1R^2)$ or $(C(R^3)\!=\!C(R^4))$;

Z is —NH(CO)—, —O—, —O(CO)—, —S—, —NH—, —NO—, —O(CO)O—, —O(CO)NH—, —NH(CO)O—, —$SO_2$—, —$OP(O)(OR^{12})O$—, —Se—, —SeO—, —$N(R^{13})$—, or —$O(CO)N(R^{13})$—;

Y is H, OH, $OR^5$, $NHR^6$, $N(R^7)_2$, $SR^8$, or halo;

$R^1$, $R^2$, $R^3$ and $R^4$ for each occurrence, are independently selected from H, $(C_6\text{-}C_{12})$aryl, $(C_5\text{-}C_{12})$heteroaryl, —(CO)$(C_1\text{-}C_6)$alkyl, $(C_1\text{-}C_{12})$alkyl, $(C_1\text{-}C_{12})$alkoxy, or hydroxyl;

M is selected from $(CR^9R^{10})_{11\text{-}23}CH_3$, $(C_6\text{-}C_{12})$aryl, $(C_5\text{-}C_{12})$heteroaryl, or $(C_{12}\text{-}C_{24})$alkenyl, wherein each $(C_6\text{-}C_{12})$aryl, $(C_5\text{-}C_{12})$heteroaryl, and $(C_{12}\text{-}C_{24})$alkenyl is optionally and independently substituted at any one or more substitutable positions by $(C_1\text{-}C_{12})$alkyl, $(C_1\text{-}C_{12})$alkoxy, hydroxyl, —$NH_2$, —$N((C_1\text{-}C_{12})alkyl)_2$, or —S—$(C_1\text{-}C_{12})$alkyl;

$R^5$, $R^6$, $R^7$, and $R^8$ are each $(C_1\text{-}C_{12})$alkyl, $(C_6\text{-}C_{12})$aryl, $(C_5\text{-}C_{12})$heteroaryl, or $(C_{12}\text{-}C_{24})$alkenyl;

$R^9$ and $R^{10}$, for each occurrence, are H, $(C_1\text{-}C_{12})$alkyl, $(C_1\text{-}C_{12})$alkoxy, hydroxyl, —$NH_2$, —$N[(C_1\text{-}C_{12})alkyl]_2$, or —$S(C_1\text{-}C_{12})$alkyl;

$R^{12}$ is H, $(CR^9R^{10})_{0\text{-}23}CH_3$, $(C_6\text{-}C_{12})$aryl, $(C_5\text{-}C_{12})$heteroaryl, or $(C_2\text{-}C_{12})$alkenyl, wherein each $(C_6\text{-}C_{12})$aryl, $(C_5\text{-}C_{12})$heteroaryl, and $(C_2\text{-}C_{12})$alkenyl is optionally and independently substituted at any one or more substitutable positions by $(C_1\text{-}C_{12})$alkyl, $(C_1\text{-}C_{12})$alkoxy, hydroxyl, —$NH_2$, —$N((C_1\text{-}C_{12})alkyl)_2$, or —S—$(C_1\text{-}C_{12})$alkyl;

$R^{13}$ is $(C_1\text{-}C_{12})$alkyl, $(C_6\text{-}C_{12})$aryl, $(C_5\text{-}C_{12})$heteroaryl, $(C_3\text{-}C_6)$cycloalkyl, or $(C_2\text{-}C_{12})$alkenyl provided that:

when any one of $R^1$ or $R^2$ is hydroxyl or $(C_1\text{-}C_{12})$alkoxy, then not all $R^9$ and $R^{10}$ are H;

when any one of $R^9$ or $R^{10}$ is hydroxyl or $(C_1\text{-}C_{12})$alkoxy, then not all $R^1$ and are H; and $(C_{12}\text{-}C_{24})$alkenyl is not $(C_{17})$alkenyl or $(C_{19})$alkenyl.

In particular embodiments, $R^1$ and $R^2$ of Formula (I), for each occurrence, are independently selected from H, $(C_6\text{-}C_{12})$aryl, or $(C_1\text{-}C_{12})$alkyl; Z is —NH(CO)—, —O—, —O(CO)—, —O(CO)O—, —O(CO)NH—, or —NH(CO)O—; Y is OH or $OR^5$; and M is $(CH_2)_{11\text{-}23}CH_3$.

In other particular embodiments, the compound of Formula (I) has one of the following structures, or a salt thereof:

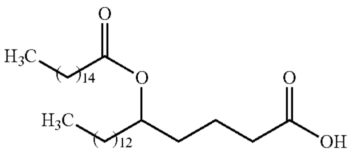

or

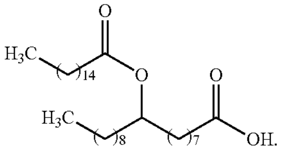

In still other particular embodiments, the compound of Formula (I) is not a compound of one of the following structures:

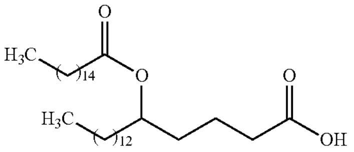

or

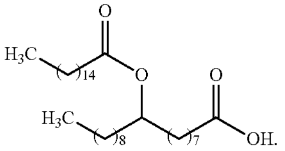

The FAHFAs of any one of Formulae (I)-(IV) may exist as a pharmaceutically acceptable salt, for example as any of the salts described in Section I. In certain embodiments, the FAHFAs of any of Formulae (I)-(IV) are detectably labeled. For example, the FAHFA derivative can be isotopically labeled and/or ester- or amide-bound to a detectable moiety, such as biotin, streptavidin, GST, a fluorous affinity tag, an alkyne suitable for click chemistry, an epitope tag such as FLAG, 6× His, or another affinity tag. In certain embodiments, the invention also provides a FAHFA derivative of any of Formula (I)-(IV) incorporated into structures such as phospholipids, glycerophospholipids, carbohydrates, polypeptides and proteins, di- and triglycerides, and conjugates to metabolic cofactors such as CoA or acyl carnitine. In further aspects, the invention provides compositions and formulations comprising a FAHFA of any of Formulae (I)-(IV). A FAHFA composition can further comprise one or more excipients such as an anti-adherents, binders, coatings, disintegrants, fillers, flavors, colors, lubricants, glidants, sorbents, osmolyte, alumina, preservatives, or sweeteners. FAHFA compositions can also further comprise one or more active ingredients, modifiers, or salts. A person of ordinary skill in the art would understand how to formulate a FAHFA composition in order to achieve a desired pharmacological effect. In certain embodiments, the pharmaceutical composition is suitable for administration to a human subject, e.g., meets guidelines set by the United States Pharmacopeia (USP) or U.S. Food and Drug Administration (FDA) under guidelines for one or more of new drugs, generic drugs, or over-the-counter drugs.

The present invention further provides methods of making the FAHFA compounds disclosed herein and derivatives thereof. Exemplary methods for the synthesis of FAHFA compounds are shown in Schemes 3 and 4. In example embodiments, such as that demonstrated by Scheme 3, a diol is oxidized to provide a compound having an aldehyde moiety and an acetal. In certain embodiments, the step of oxidation is oxidative desymmetrization. Nucleophilic addition to the aldehyde, for example, by a Grignard reagent or an organolithium reagent, yields a secondary alcohol. Sequential and selective protection, deprotection, oxidation, and deprotection steps yield a hydroxy-bearing ester compound. Further selective and sequential protection, esterification, and deprotection steps reveal the FAHFA. Such methods tolerate a variety of organic substituents.

In other example embodiments, such as that demonstrated by Scheme 4, nucleophilic addition to an aldehyde yields a secondary alcohol. In the example embodiment of Scheme 4, the nucleophile contains an alkene group, though a skilled artisan would recognize that in alternate embodiments, the alkene can be present in the aldehyde. The secondary alcohol is esterified, and the remaining alkene is converted to an oxidized group, for example a carboxylic acid, an amide, or a thioester. The step of conversion occurs through an oxidative method, such as ozonolysis and oxidation, or other methods known to those of ordinary skill in the art.

A person of ordinary skill in the art would be able to modify the experimental protocols exemplified in Schemes 3 and 4 to reach the FAHFA of the desired structure and configuration without undue experimentation.

EXAMPLES

The following examples serve to illustrate, and in no way to limit, the present invention.

Example 1

Identification of a Novel Class of Fatty Acid Conjugates by Metabolomics.

As described herein, a novel class of lipid metabolites has been identified through the application of metabolomics to the analysis of adipose tissue from transgenic mice that overexpress the insulin-responsive glucose transporter, GLUT4, in adipose tissue but not in muscle [1-3]. Glucose disposal was enhanced in isolated adipocytes from transgenic mice versus wild-type controls. This led to altered gene expression, including genes involved in lipid metabolism, and whole-body insulin sensitivity was improved despite the fact that GLUT4 overexpression was localized to adipose tissue. Furthermore, adipose GLUT4 overexpression can reverse the insulin resistance and diabetes in mice lacking GLUT4 in muscle [3]. These data suggested that a circulating factor, perhaps a lipid, may exert anti-diabetic effects on peripheral tissues in these mice.

Figure 1:
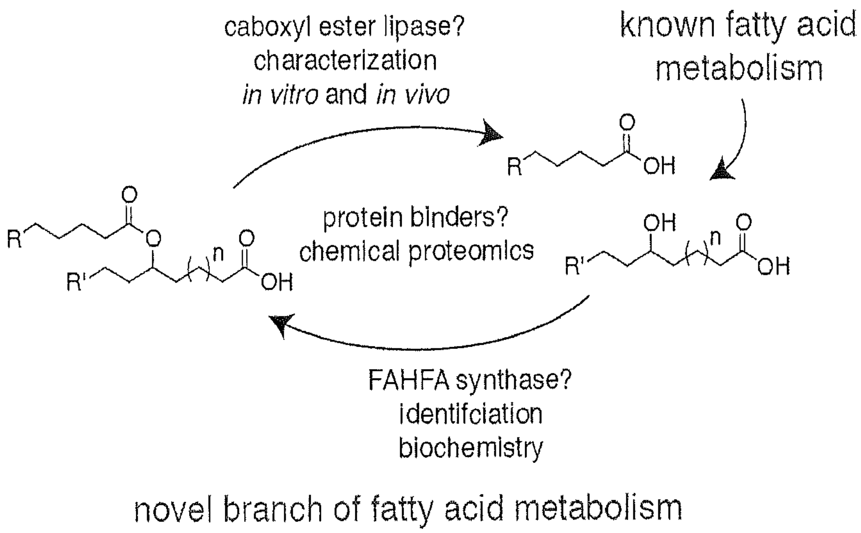
FIG. 1 shows a novel FAHFA pathway.
Figure 2:
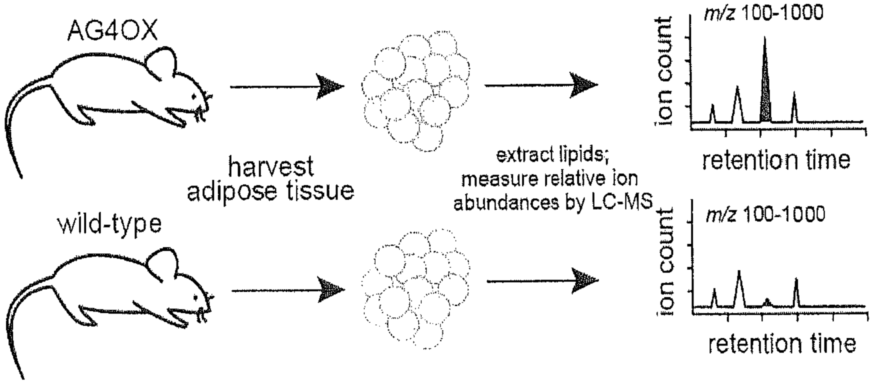
FIG. 2 shows comparative metabolite profiling of adipose GLUT4-overexpressing (AG4OX) and wild-type mice (WT) by LC-MS-based metabolomics.

Given the elevated expression of genes involved in lipid metabolism, it was decided to measure changes in adipose tissue from these mice to identify any specific changes in their lipid metabolism. Subcutaneous adipose tissue from GLUT4-overexpressing or wild-type mice was homogenized and extracted with chloroform-methanol-water [4-6] to yield lipid extracts that were analyzed by LC-MS (FIG. 2). The analysis was performed on a time-of-flight (TOF) mass spectrometer whose high mass accuracy permits the direct calculation of candidate molecular formulae [6]. The LC-MS chromatograms were aligned and compared by XCMS [7], a data analysis software for metabolomics applications. A cluster of ions in AG4OX AT was elevated≥16-fold. Metabolite ions were ranked by statistical significance and fold change to highlight changing ions of interest; these data were plotted on a volcano plot (FIG. 49A). The exact mass of these highly elevated metabolites was determined and their molecular formulas were deduced as $C_{32}H_{61}O_4$ (509.4575), $C_{34}H_{63}O_4$ (535.4732), $C_{34}H_{65}O_4$ (537.4888) and $C_{36}H_{67}O_4$ (563.5045). These formulas all contain a unique signature of four oxygen atoms indicating that these ions are members of a single lipid class. These ions were observed in both transgenic and wild type samples, though at 40-fold higher levels in the transgenic samples. These novel lipids were hypothesized to contribute to systemic insulin sensitivity because of their abundance in AG4OX mice, in which improved glucose tolerance and insulin sensitivity depends on enhanced lipogenesis in AT [24]. The molecular structures of these lipids and their biologic effects were next examined.

Structural Characterization of Novel Metabolite.

The most abundant ion in this family exhibited a mass-to-charge ratio of m/z 537.487 that was consistent with the molecular formula $C_{34}H_{66}O_4$. Analysis of the fragmentation pattern of each member of the ion family on a quadrupole TOF mass spectrometer revealed that these metabolites were likely fatty acyl-hydroxy fatty acid conjugates, herein abbreviated as FAHFA. Fragmentation of the m/z 537 species, in particular, generated several product ions with masses of 255, 281 and 299 (FIG. 49B), which correspond to palmitic acid (PA), octadecenoic acid, and hydroxy stearic acid (HSA), respectively. The molecular formula of the 537 ion ($C_{34}H_{65}O_4$) does not contain any double bonds. This indicates that octadecenoic acid, which contains a double bond, results from fragmentation in the MS and is not part of the natural metabolite. Based on the chemical formula and the fact that this metabolite ionized only in the negative mode, the most reasonable structure for the 537 ion is an ester that combines PA and HSA to yield Palmitic Acid-Hydroxy Stearic Acid (FIGS. 49B and 49C), abbreviated as PAHSA.

Based on this structural model and the masses detected for the other elevated ions, their structures are: Palmitic Acid-Hydroxy Palmitic Acid (PAHPA, m/z 509), Oleic Acid-Hydroxy Stearic Acid (m/z 563, OAHSA), and the 535 ion is a mixture of PalmitOleic Acid-Hydroxy Stearic Acid (POHSA) and Oleic Acid-Hydroxy Palmitic Acid (OAHPA) (FIG. 49C). Additional FAHFAs are shown in FIGS. 49C and 49D.

Using a targeted MS approach, 16 FAHFA family members were identified in mouse serum that consisted of four fatty acids and four hydroxy-fatty acids in different combinations (FIG. 49D).

FAHFAs with PO, PA or OA as the fatty acid moiety and HPA or HSA as the hydroxy-fatty acid were most highly increased in AG4OX compared to WT mice (FIG. 49D).

The precise isomer of hydroxystearic acid that was elevated in the transgenic mice was then determined. At high collisional dissociation energies (50 V), 12-hydroxystearic acid produced diagnostic fragment ions, m/z 113 and 169, resulting from bond cleavage at predictable locations near the hydroxyl group [8]. 12-PAHSA was synthesized from commercially available 12-HSA and, in both species, the same diagnostic fragment ions were observed. This indicated that the high energy HFA fragmentation method could extend to the identification of the position of the hydroxyl group of FAHFAs. From the fragmentation pattern of FAHFAs seen in vivo, it was determined that the major isomer of the upregulated lipid was 9-PAHSA. To confirm the structure [$^{13}$C]-labeled 9-PAHSA was synthesized from commercially available 9-HSA and all-[$^{13}$C]-palmitic acid, which was then coextracted with transgenic adipose tissue and analyzed without further purification. It was observed by LC-MS that the authentic standard coeluted at the same retention time with the major natural isomer.

Example 11 summarizes further characterization studies of FAHFA species.

Tissue Distribution of PAHSA Levels in Wild Type Mice.

In order to assess the relevance of these novel lipids in normal mammalian biology, PAHSA levels were measured in several wild-type tissues by isotope-dilution mass spectrometry (IDMS) using our [$^{13}$C]-9-PAHSA standard and a highly sensitive multiple reaction monitoring (MRM) method. Tissues were extracted in the presence of a known amount of internal standard, and the ion intensities were ratioed to obtain absolute levels of PAHSA in the tissues, expressed as nmol/g tissue. The presence of PAHSA was observed in all tissues measured, and PAHSA levels were highest in pancreas and kidney (~10 nmol/g tissue), indicating that their presence was not merely an artifact of the transgenic mouse model. These lipid levels are below those of unesterified saturated fatty acids such as stearate or palmitate but are comparable to the levels of some signaling molecules such as 2-arachidonoylglycerol or oleoylethanolamine in brain tissue [9-10]. Nevertheless, it is believed that these specific lipid structures have never been previously described, and they constitute a novel class of fatty acid conjugates.

Development of an Assay to Measure FAHFA Degradation Activity.

Figure 3:
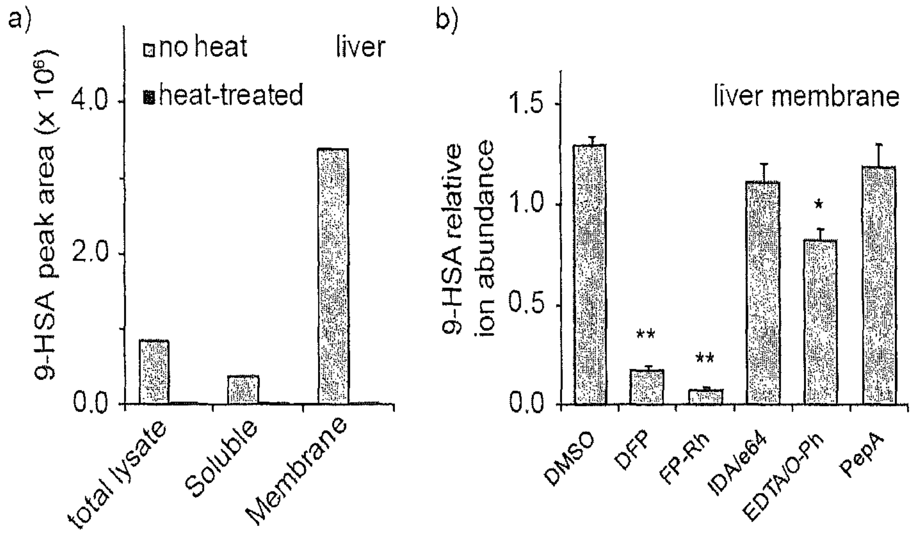
FIGS. 3*a* and 3*b* show (a) FAHFA hydrolysis activity enriched in liver membrane, and (b) the hydrolytic activity is a serine hydrolase.

To establish whether or not FAHFA can be enzymatically degraded, an LC-MS-based in vitro activity assay was developed to measure the hydrolysis of 9-PAHSA to 9-HSA. Liver tissue was initially profiled because it contains a large number and variety of hydrolytic enzymes [11-12]. Liver lysate (1 mg/ml protein) was incubated with 100 μM 9-PAHSA at 37° C. for two hours. The reaction mixture was then extracted with one volume ethyl acetate, concentrated under nitrogen gas stream, and reconstituted in 1:1 chloroform:methanol for MS analysis. Substantial 9-HSA production was observed that was enriched in the membrane fraction (isolated by ultracentrifugation) and depleted in the soluble fraction (FIG. 3*a*). To determine the class of enzyme responsible for FAHFA hydrolysis, several classes of enzyme inhibitors were screened. Only the serine hydrolase inhibitors demonstrated nearly complete abrogation of FAHFA hydrolysis (FIG. 3*b*), and inhibition by the fluorophosphonate inhibitor DFP was dose-dependent (not shown).

Identification of a FAHFA-Degrading Enzyme.

Figure 4:
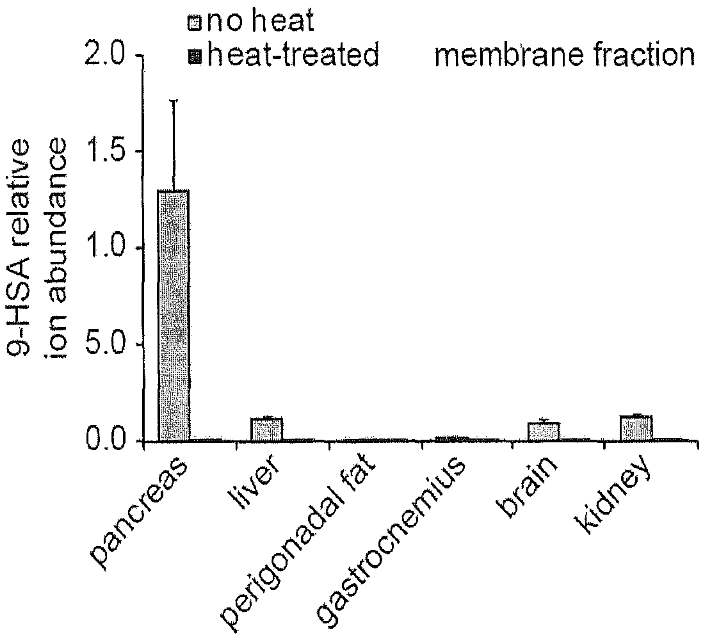
FIG. 4 shows tissue distribution of FAHFA hydrolysis activity (n=3).

A global database of serine hydrolases, complete with tissue distribution data, was recently assembled by Cravatt and colleagues [11]. The candidates were narrowed down further by comparing the tissue distribution of FAHFA hydrolysis activity to the tissue distribution of activity for every membrane-localized serine hydrolase. Membrane fractions were prepared from pancreas, liver, fat, muscle, brain and kidney, then diluted to 1 mg/ml protein concentration and incubated with 100 μM 9-PAHSA for 30 min at room temperature. Pancreas membrane exhibited the highest FAHFA hydrolysis activity and was ~10-fold higher than in liver membrane (FIG. 4).

Figure 5:
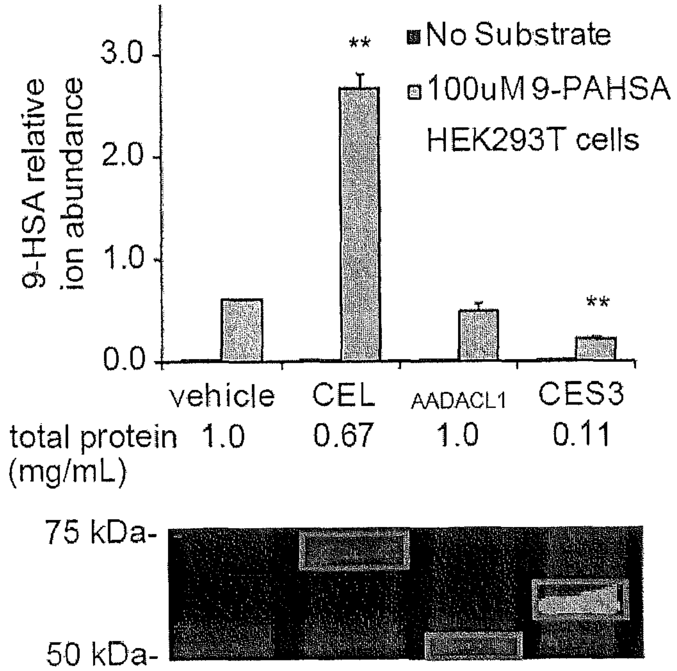
FIG. 5 shows hydrolysis of FAHFA by transfected HEK293T cell lysates (top) and expression levels by ABP gel (bottom).

Only three membrane-bound serine hydrolases were reported to possess significant activity in pancreas: carboxyl ester lipase (CEL), arylacetamide deacetylase-like 1 (AADACL1), and carboxylesterase 3 (CES3). Plasmid expression clones for these enzymes were obtained, which were under the control of the cytomegalovirus promoter (from the Cravatt lab), with which we transfected HEK293T cells to assess the ability of these enzymes to hydrolyze 9-PAHSA. For the activity assays, cell lysates were diluted according to the relative expression of the three clones according to ABP intensities. Remarkably, only CEL-transfected cell lysate was able to hydrolyze FAHFA above the level of background hydrolysis activity present in the untransfected HEK cell lysate (FIG. 5). The increased activity in CEL-transfected cell lysates was reversed by addition of the CEL-selective inhibitor, WWL92 [13] (not shown).

Figure 6:
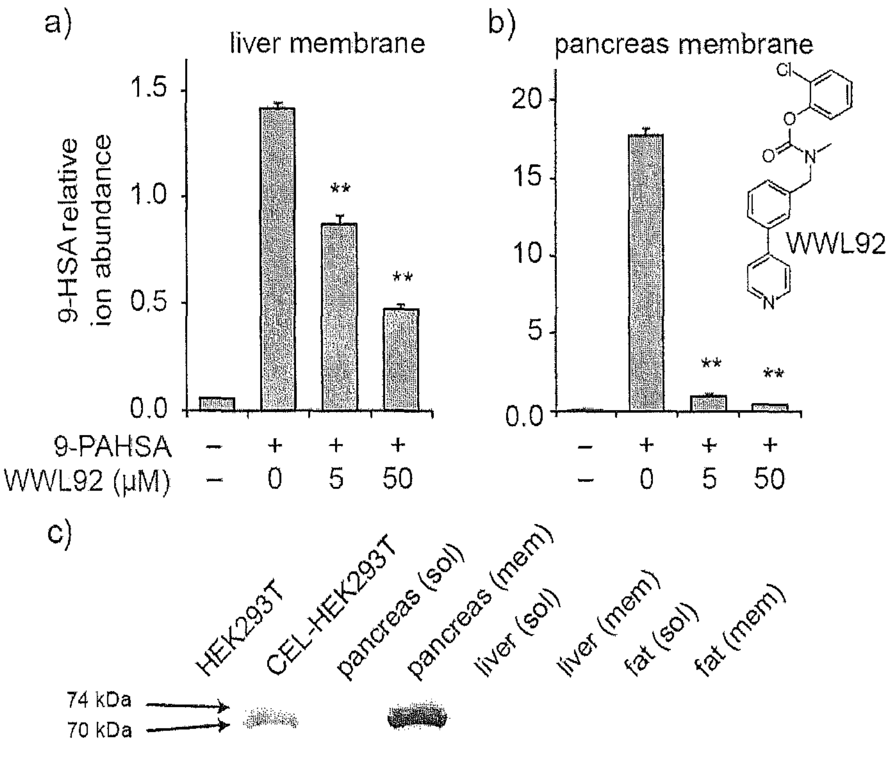
FIGS. 6*a*, 6*b*, and 6*c* show that (a) WWL92 inhibits FAHFA hydrolysis partially in liver, but (b) almost completely in the pancreas; (c) shows CEL expression in the pancreas and liver.

Inhibition of FAHFA hydrolysis by WWL92 treatment was observed in liver and pancreas membrane lysates in a dose-dependent manner. Liver activity was only partially inhibited, while the higher pancreas activity was almost completely extinguished by WWL92 treatment (FIGS. 6*a, b*). High levels of WWL92-sensitive hydrolysis activity in the pancreas were consistent with the relative tissue abundance of CEL expression as measured by immunoblotting (FIG. 6*c*).

Bile-Salt Activation of FAHFA Hydrolysis.

Figure 7:
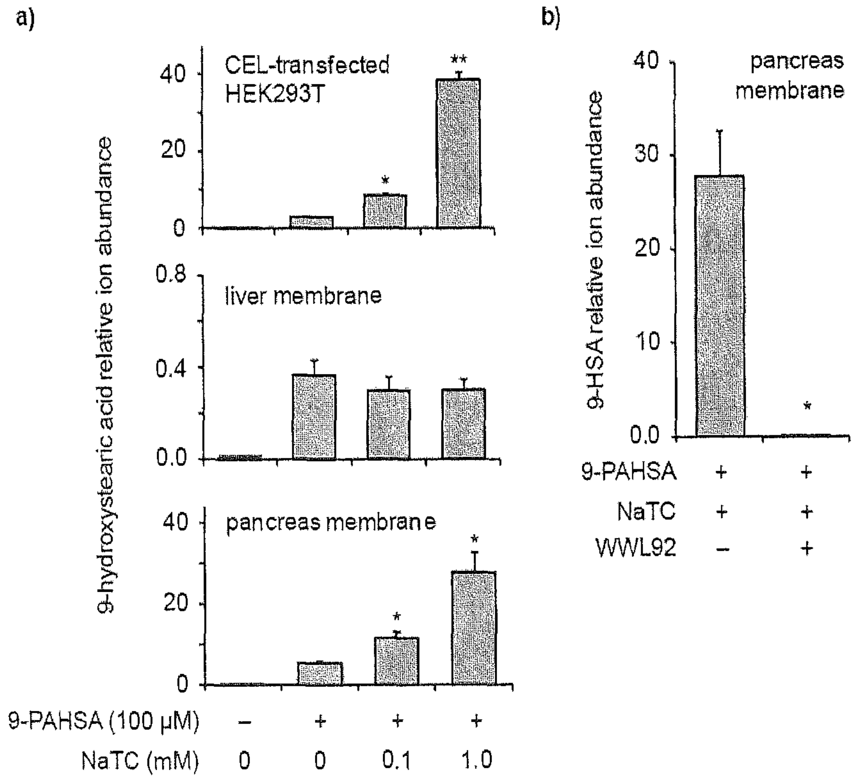
FIGS. 7*a* and 7*b* show supplementation of FAHFA hydrolase activity assays in a) CEL-transfected cell lysates, liver and pancreas membrane lysates and (b) pancreas membrane lysates treated with WWL92 (20 uM).

Originally characterized as "bile salt-activated lipase", CEL is secreted by acinar pancreatic cells into the duodenum where it plays a significant role in dietary lipid digestion [14]. Its activity is enhanced by primary bile salts, such as sodium taurocholate (NaTC), which promote substrate access to the lipase active site [15]. CEL-transfected cell lysates were treated with increasing concentrations of NaTC in the presence of 9-PAHSA and verified that FAHFA hydrolysis was enhanced (FIG. 7*a*). The experiment was repeated with either liver or pancreas membrane lysate. Notably, FAHFA hydrolysis in liver lysate was not enhanced by NaTC, while FAHFA hydrolysis in pancreas lysate was markedly increased (FIG. 7*a*). Pancreas membrane lysate was then pretreated with WWL92 and verified that the increase in FAHFA activity upon treatment with NaTC was due to increased CEL activity (FIG. 7*b*).

Preliminary Experiments with Purified CEL.

Figure 8:
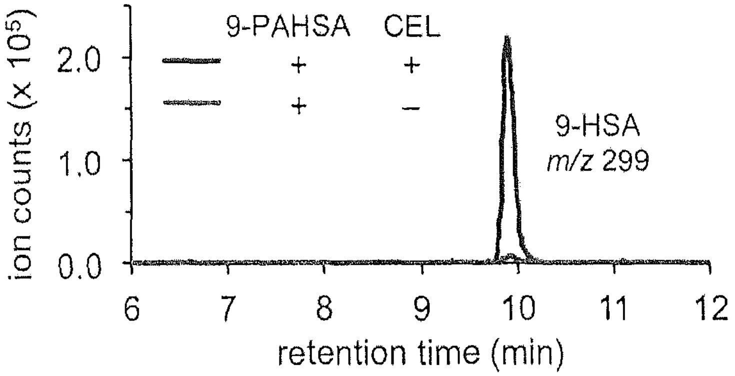
FIG. 8 shows the reaction of 9-PAHSA CEL in the presence of micellar NaTC concentrations.

To confirm the identification of CEL as a FAHFA hydrolase, a small amount of purified enzyme (available commercially from R&D Systems) was used. As expected, substantial hydrolysis of 9-PAHSA was observed, as measured by 9-HSA production, when incubated with purified CEL in the presence of micellar concentrations of NaTC (FIG. 8). The results were comparable to CEL hydrolysis activity of a known substrate, dioleoylglycerol (DOG) [14].

Development of an Assay to Measure FAHFA Acyltransferase Activity.

In order to understand the biology of the new FAHFA lipid class more completely, experiments were performed to identify an enzyme capable of synthesizing FAHFAs as well. By structural analogy to other lipid metabolites such as diacylglycerols or wax esters, it was hypothesized that hydroxy fatty acids were the immediate precursors to FAHFAs. Candidate acyltransferases were identified by reacting the common biochemical acyl carrier, oleoyl-CoA, with 9-hydroxystearic acid (9-HSA) in the presence of cell lysates or tissue membrane lysates to form 9-OAHSA (Scheme 2).

Scheme 2.

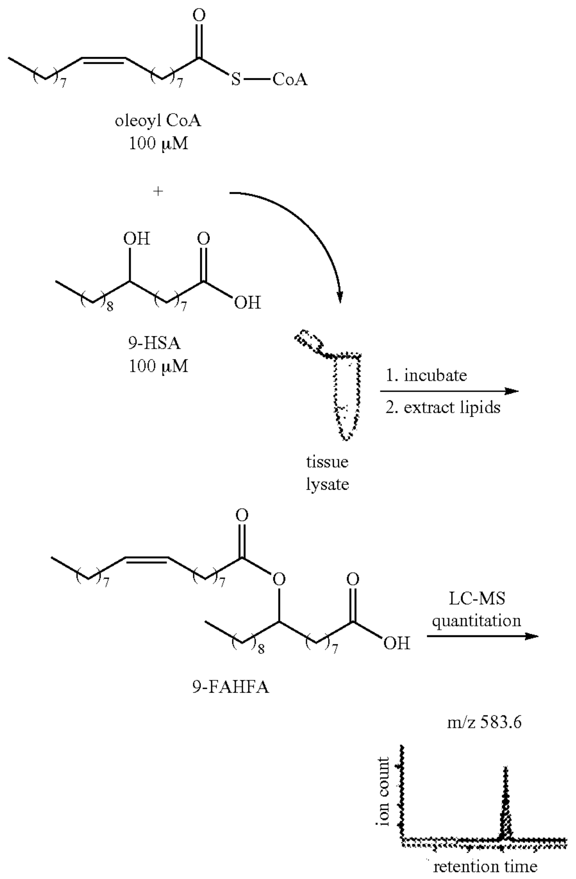

oleoyl CoA 100 μM

9-HSA 100 μM

9-FAHFA

Figure 9:
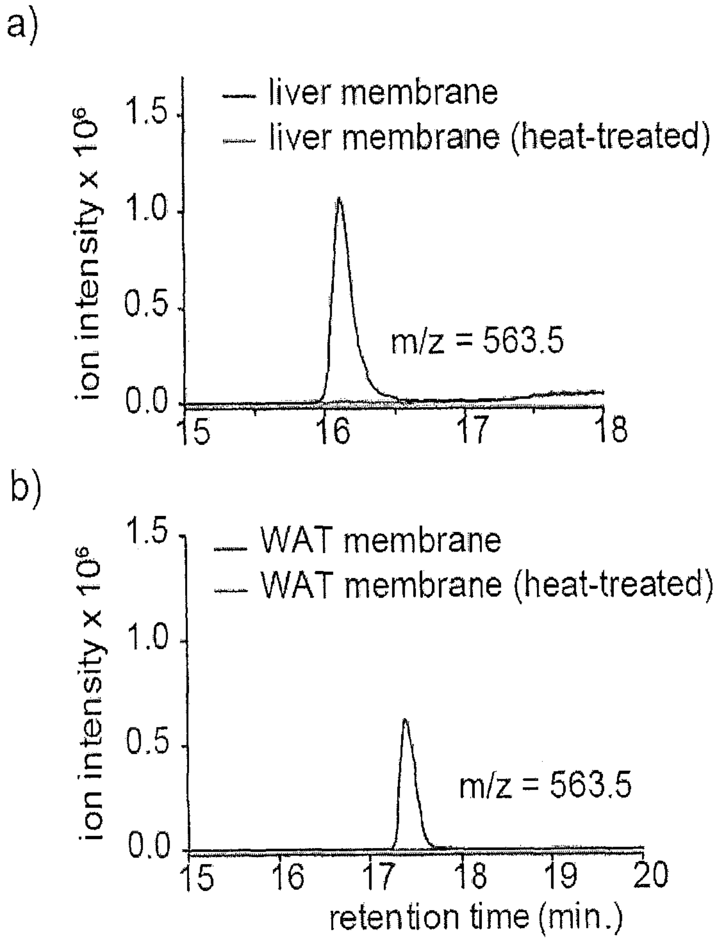
FIGS. 9*a* and 9*b* show the production of 9-OASHA (m/z 563.5) by tissue membrane lysates.

After first establishing that FA-CoA:HFA acyltransferase activity was membrane-localized in liver (not shown), membrane fractions from liver or WAT tissue lysate were isolated by ultracentrifugation, then resuspended the pellets in PBS buffer and diluted to 1 mg/ml protein concentration. Oleoyl-CoA and 9-HAS were incubated, both at 100 μM concentration, with the membrane lysates for 2 hours at 37° C. The reaction mixtures were extracted with ethyl acetate, concentrated, and reconstituted in 1:1 chloroform:methanol for MS analysis. Formation of 9-OAHSA was measured by MS/MS, with which the appearance of the parent ion m/z 563 was monitored. Substantial 9-OAHSA production was observed in both liver and WAT samples, but not in heat-treated samples (FIG. 9).

Figure 10:
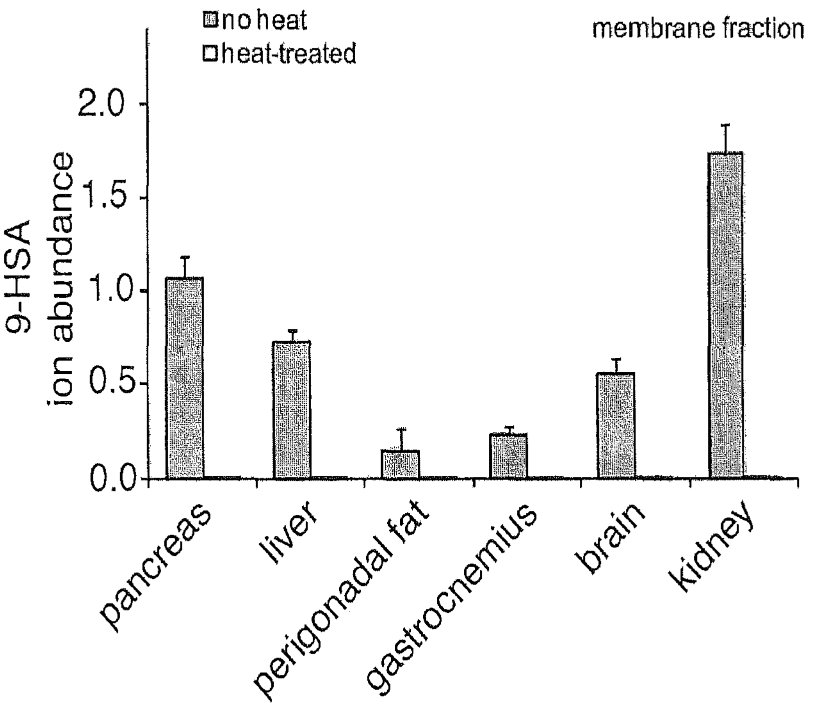
FIG. 10 shows the tissue distribution of FA-CoA:HFA acyl transferase activity.

To assess whether the observed activity was limited to liver and WAT, the tissue distribution of HFA acylation activity was explored by performing the FAHFA biosynthesis assay with membrane lysates from pancreas, liver, fat, muscle, brain and kidney (FIG. 10). Production of 9-OAHSA was observed at comparable levels in all tissues, well in excess of background activity. Highest levels were detected in pancreas and kidney, which parallels the tissue distribution of FAHFA levels in vivo.

Efforts to Identify Candidate Acyltransferases with FAHFA Biosynthesis Activity.

Figure 11:
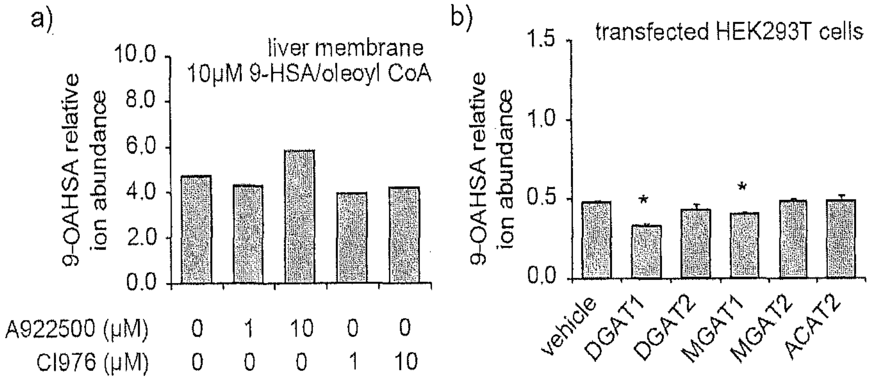
FIGS. 11*a* and 11*b* show that (a) FAHFA biosynthesis is unaffected by DGAT1 or ACAT inhibitors, and (b) that increased FA-CoA:HFA acyltransferase activity is not observed in HEK293T cells transfected with acyltransferase clones (n=3).

In light of the above results acyltransferase families that have been reported to have a membrane-bound localization and to have the ability to conjugate FA-CoA to a hydrophobic alcohol were targeted [16-19]. Two of the enzymes, DGAT1 and ACAT, had selective inhibitors that were commercially available, A922500 [20] and CI976 [21], which were used to test their ability to reduce FAHFA production in the biosynthesis assay (inhibitors purchased from Tocris Bioscience). Tissue lysates were incubated with a reduced concentration of 9-HSA and oleoyl-CoA (10 μM) and with increasing doses of A922500 or CI976, but no change in 9-OAHSA levels was observed (FIG. 11*a*). This suggested that neither DGAT1 nor ACAT, two FA-CoA:HFA acyltransferase candidates, were responsible for the observed biosynthesis activity in the tissues studied.

Next it was attempted to increase FAHFA production by transfecting HEK293T cells with expression-ready clones of DGAT1/2, MGAT1/2, and ACAT2 enzymes (from Dr. Robert Farese, UCSF) [22]. Overexpression of these enzymes did not lead to elevated FA-CoA:HFA acyltransferase activity compared to the background activity in HEK293T cell lysate (FIG. 11*b*). This experiment indicates that these five enzymes are likely not FA-CoA:HFA acyltransferases.

FAHFA Biosynthesis Activity in 3T3-L1 Adipocytes.

Figure 12:
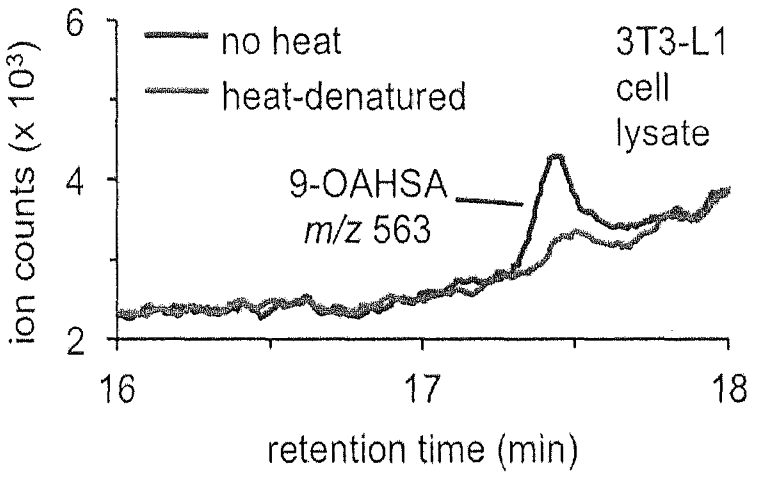
FIG. 12 shows FA-CoA:HFA acyl transferase activity in 3T3-L1 cell lysates.

Since FAHFAs were initially discovered in adipose tissue, and CEL is not known to be significantly expressed in fat, it was next investigated whether adipose FAHFA levels could be controlled by an acyl-CoA:HFA acyltransferase. As a first step, whole cell lysates from mature 3T3-L1 cells were incubated with oleoyl-CoA and 9-HAS, then extracted and analyzed by LC-MS (FIG. 12). Meaningful production of 9-OAHSA was observed in these cells, implying that 3T3-L1 cells possess the ability to produce, not merely store, the conjugated FAHFAs.

Correlation of Changes in HFA Levels with Changes in FAHFA Levels.

Figure 13:
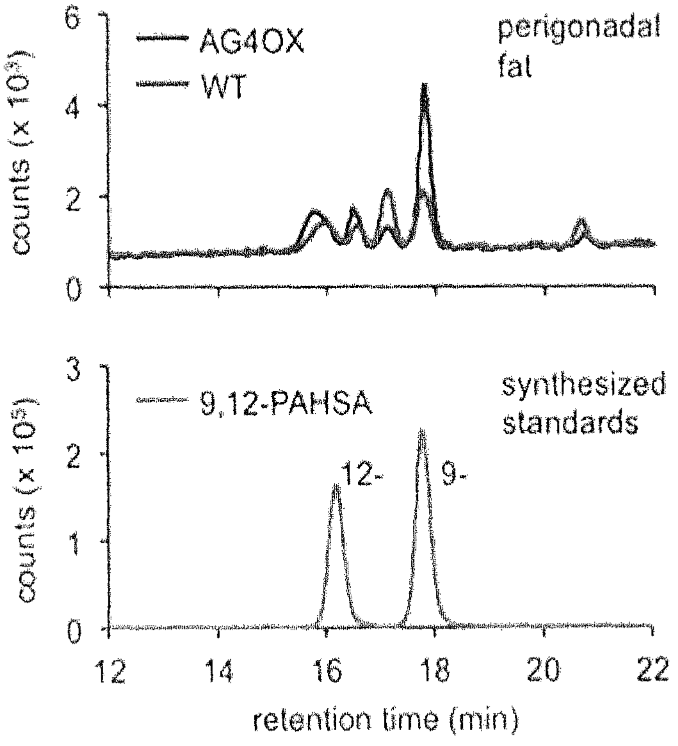
FIG. 13 shows an LC-MS trace of isomers of hydroxystearic acid in AG4OX fat with comparison to commercially purchased 12- and 9-HSA standards. Samples were analyzed on a QQQ-MS in selected ion monitoring (SIM) mode targeting the m/z 299.3 ion.

HFA levels in the lipid extracts from AG4OX and WT mice were measured to analyze their hydroxyl fatty acids (HFAs) (FIG. 13). Representative lipid extracts from WT and AG4OX adipose tissue were compared to 9- and 12-HSA standards (Indofine Chemical Company and Sigma-Aldrich). Interestingly, AG4OX fat exhibited a three-fold enrichment in 9-HSA abundance compared to WT fat, which was more modest than the robust fold change observed in 9-PAHSA levels in these tissues. It is reasonable to believe that 9-PAHSA, acting as a storage form of 9-HSA, may preferentially accumulate in tissues rather than 9-HSA in response to increased 9-HSA levels.

Chemical Synthesis of the FAHFAs.

The identification of the FAHFAs required that these compounds be synthesized to confirm that the structural assignments were correct. To enable the synthesis a simple approach was developed that would enable one to make a variety of FAHFA derivatives (Scheme 3). In the initial synthesis, large amounts of the 9-hydroxy FAHFA were prepared. The strategy began with the simple desymmetrization of a 1,9-nonanediol, available in large quantities using substoichometric equivalents of a dihydropyran protecting group, which afforded the mono-THP protected alcohol (30% yield). This alcohol was then oxidized to the aldehyde (1) using PCC[58,59] (53% yield). Addition of the Grignard reagent n-nonylmagnesium bromide to 1 resulted in a secondary alcohol at position 9 of the alkyl chain (63% yield). This material was acylated with acetic anhydride to afford the THP-protected acetate (2) (100% yield). In a series of steps then carried out without purification, the THP group was removed with PPTS, the resulting alcohol oxidized to an aldehyde with PCC and the aldehyde oxidized to the carboxylate with sodium chlorite. Finally, the acetate was removed with lithium hydroxide to afford 9-HSA (3, 52% overall yield for the four steps).

An alternate synthetic route to the FAHFAs was designed, in which ozonolysis followed by an oxidative workup allowed access to the carboxylate moiety of the FAHFA (Scheme 4).

Scheme 3

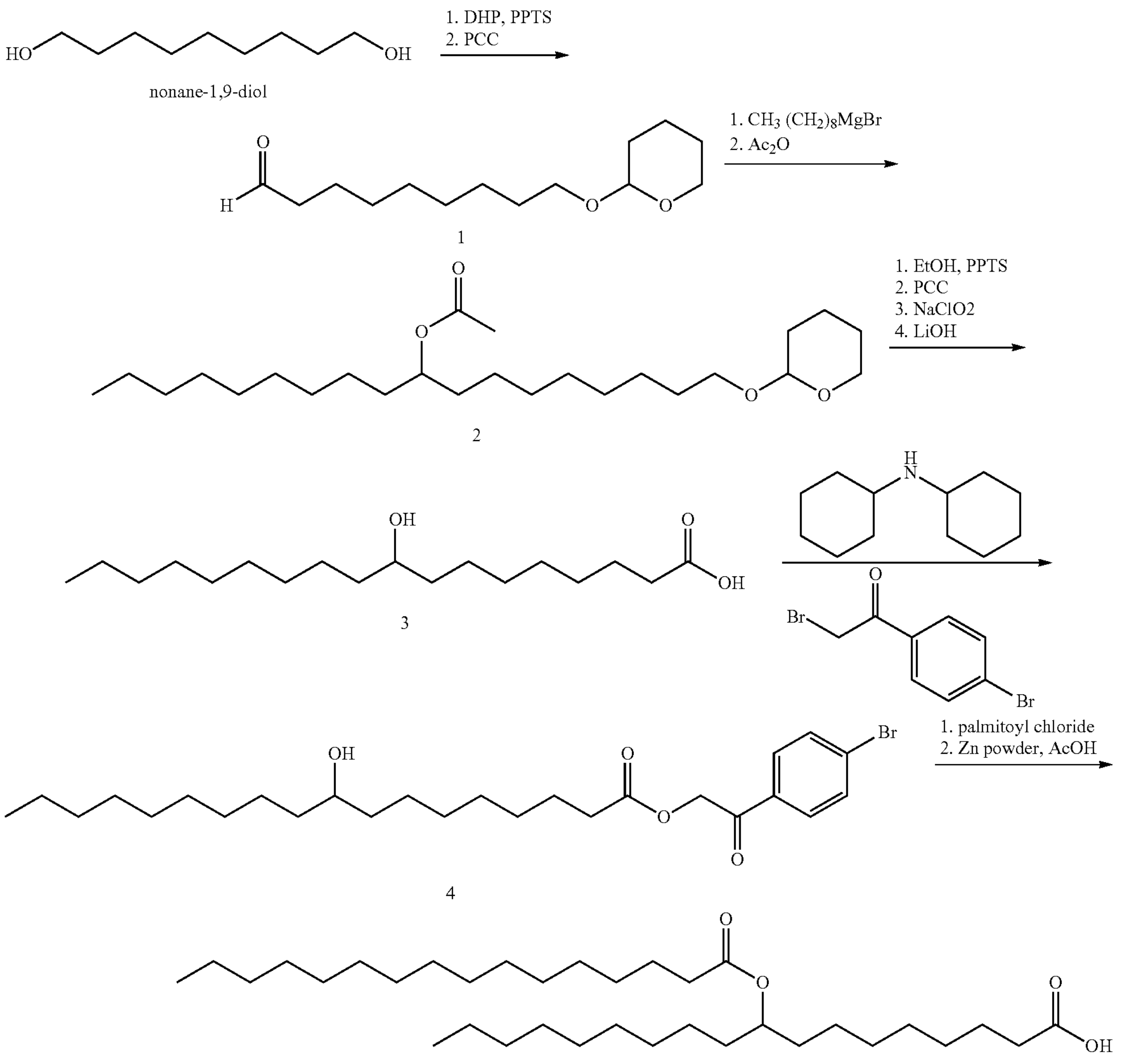

nonane-1,9-diol
1
2
3
4

FAHFA

Next, using method developed by Zhang and colleagues the 9-HAS was reacted with 2-bromo-1-(4-bromophenyl) ethanone to give the protected ester (4, 20% yield) [23]. Our yield was much lower than the reactions reported in the original paper so further optimization will be necessary. Nevertheless, sufficient material was isolated to complete the synthesis by acylating the hydroxyl group of 4 with palmitoyl chloride in the presence of 4-dimethylaminopyridine (DMAP) followed by deprotection with zinc dust in acetic acid to provide the FAHFA (53% overall yield for the two steps). Importantly, this synthetic route is highly modular and the key pieces are commercially available, which will enable the rapid synthesis of additional derivatives. Different FAHFA derivatives can be synthesized using this route to enable the isolation and identification of FAHFA-binding proteins.

Scheme 4.

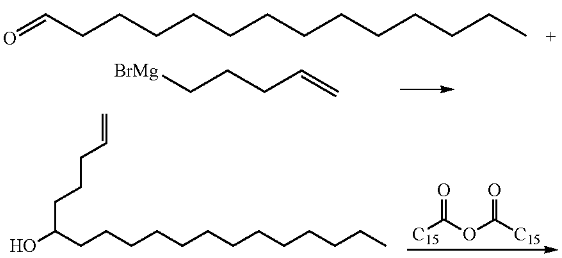
5

-continued

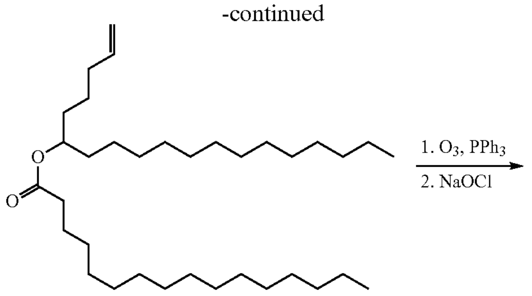

6

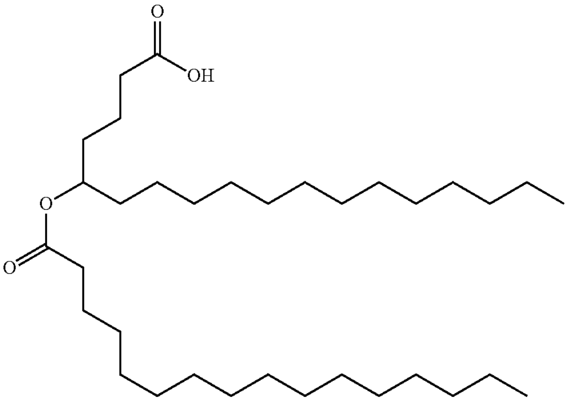

7

Synthesis of nonadec-1-en-6-ol (5)

To a stirred solution of tetradecanal (1.5 g, 7.1 mmoles, 1 eq) in THF (50 mL) on an ice bath was added pent-4-en-1-ylmagnesium bromide (21.2 mL, 10.6 mmoles, 1.5 eq, 0.5 M solution in THF) by syringe. The solution stirred overnight (16 hours) and over this time warmed to room temperature. The reaction was quenched by the addition of a saturated solution of ammonium chloride (1 mL), concentrated onto celite 545 (10 g), and purified by silica gel chromatography (15% EtOAc/hexanes). Pure fractions were combined and concentrated to afford a white solid (570 mg, 28%); $R_f$=0.17, 10% EtOAc/hexanes; $^1H$ NMR (400 MHz, $CDCl_3$ (7.26 ppm)): 5.846-5.761 (m, 1H), 5.022-4.920 (m, 2H), 3.584 (s, 1H), 2.070-2.055 (d, 2H), 1.42-1.24 (m, 29H), 0.863 (t, 3H); m/z (ESI+) found [$MNH_4^+$] $C_{19}H_{42}NO^+$, 300.3259; calculated for $C_{19}H_{42}NO^+$: 300.3261, ΔPPM=0.67.

Synthesis of nonadec-1-en-6-yl palmitate (6)

To a stirred solution of nonadec-1-en-6-ol (570 mg, 2 mmoles, 1 eq) in $CH_2CL_2$ (20 mL) was added palmitic anhydride (1.2 g, 2.4 mmoles, 1.2 eq), 4-(dimethylamino) pyridine (122 mg, 1 mmole, 0.5 eq), and triethylamine (1.1 mL, 8 mmole, 4 eq). The solution stirred overnight (16 hours) at room temperature. The reaction was concentrated onto celite 545 (10 g), and purified by silica gel chromatography (10% EtOAc/hexanes). Pure fractions were combined and concentrated to afford a clear, colorless, oil (750 mg, 71%); $R_f$=0.33, 15% EtOAc/hexanes; $^1H$ NMR (400 MHz, $CDCl_3$ (7.26 ppm)): 5.846-5.761 (m, 1H), 5.022-4.920 (m, 2H), 3.584 (s, 1H), 2.070-2.055 (d, 2H), 1.42-1.24 (m, 29H), 0.863 (t, 3H); m/z (ESI+) found [$MH^+$] $C_{35}H_{69}O_2^+$, 521.5302; calculated for $C_{35}H_{69}O_2^+$: 521.5292, ΔPPM=1.92.

Synthesis of 5-PAHSA (7)

Ozone was bubbled into a stirred solution of nonadec-1-en-6-yl palmitate (104 mg, 0.2 mmoles, 1 eq) in $CH_2CL_2$ (20 mL) at −78° C. until the solution turned blue. Oxygen was then bubbled into the reaction until it was colorless and triphenyl phosphine (104 mg, 0.4 mmole, 2 eq) was added and the reaction warmed to room temperature. After 2 hours, the solution was concentrated. Sodium hypochlorite (112 mg of an 80% grade stock, 1 mmole, 5 eq.), sodium phosphate monobasic (138 mg, 1 mmole, 5 eq.), 2 methylbut-2-ene (1.6 mL, 16 mmole, 80 eq.), water (3.6 mL) and tert-butanol (14 mL) were added and the reaction stirred overnight. The reaction was concentrated and taken up in methylene chloride and then washed with 10% HCl in a separatory funnel. The organic layer was dried with sodium sulfate, filtered and then concentrated using a rotovap. An waxy solid bordering on an oil remained in the flask. This residue was dissolved in a minimal amount of ethyl acetate and the purified by silica gel chromatography (20% EtOAc/hexanes). Pure fractions were combined and concentrated to afford a white solid (750 mg, 71%); Rf=0.33, 15% EtOAc/hexanes; $^1H$ NMR (400 MHz, $CDCl_3$ (7.26 ppm)): 5.846-5.761 (m, 1H), 5.022-4.920 (m, 2H), 3.584 (s, 1H), 2.070-2.055 (d, 2H), 1.42-1.24 (m, 29H), 0.863 (t, 3H); m/z (ESI+) found [$MH^-$] $C_{34}H_{65}O_4^-$, 537.4905; calculated for $C_{34}H_{65}O_4^-$: 537.4888, ΔPPM=3.16.

Example 2

FAHFAs in White Adipose Tissue (WAT).

Figures 16, 17:
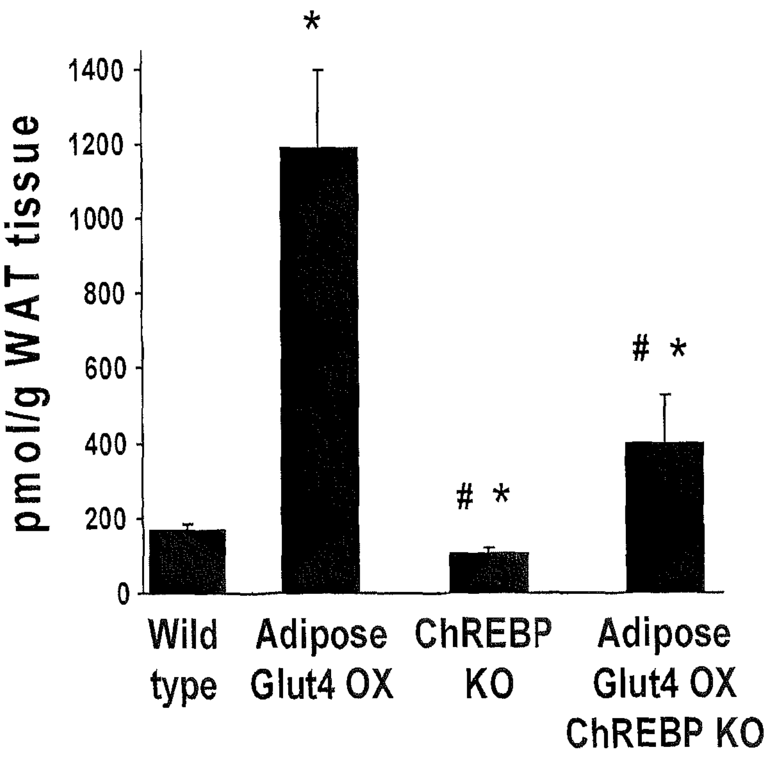
FIG. 16 shows FAHFAs present in human serum and fat.
FIG. 17 shows that total FAHFA levels are markedly increased in adipose tissue of Adipose Glut4 overexpressing mice and that FAHFAs are regulated by ChREBP in adipose tissue of normal mice and adipose Glut4 overexpressing mice (*p<0.05 vs wild type; #p<0.05 vs adipose Glut4 OX).

From a previous study, it was found that there is a strong correlation between adipose-ChREBP expression and insulin sensitivity in humans (FIG. 15). Because enhanced lipogenesis in WAT of mice with adipose-selective overexpression of Glut4 was found to be critical for the enhanced insulin sensitivity in this model [24-25], and because Glut4 is markedly down-regulated in WAT in obese and insulin resistant humans [1], the determinates of which lipids were being synthesized in response to increased adipose-Glut4 expression was carried out by an untargeted lipidomics analysis. Many classes of lipids were altered in WAT of adipose-Glut4 overexpressing mice but one class stood out as very highly upregulated. Using Mass Spectrometry, it was determined that this is a novel class of lipids that has not been described before in mammalian tissues. Structural studies revealed that they were fatty acyl hydroxy fatty acids (FAHFA). When the fatty acyl group is palmitate and the ester bond with the hydroxy fatty acid (stearic acid) is at position 9, this yields palmitoyl-9-hydroxystearic acid (9-PAHSA) whereas when the fatty acyl group is oleate and the ester bond is at position 8, this yields oleoyl-8-hydroxystearic acid (8-OAHSA). There were at least 8 FAHFA family members in tissues including WAT, BAT, pancreas, liver, muscle, kidney and brain and several of these forms were present in serum (FIG. 16). Levels were particularly high in pancreas and kidney.

To determine the relevance of FAHFAs to humans, FAHFA levels were measured in human serum and adipose biopsies. FAHFAs were present in serum of normal people at a concentration of 45-100 nanomolar and in adipose tissue at ~1 pmol/mg of lipid (FIG. 16). The serum concentrations were somewhat higher than hormones including testosterone, estradiol, vitamin D and triiodothyronine and were lower than most other fatty acids. The tissue levels were lower than nonesterified saturated fatty acids such as stearate or palmitate but were comparable to levels of signaling lipids such as 2-arachidonoylglycerol (a physiological ligand for cannabinoid receptors) and oleoylethanolamine (a ligand for PPARalpha) in brain tissue [9-10].

Since ChREBP expression and ChREBP-driven lipogenesis in WAT is highly associated with insulin sensitivity in rodents and humans [24], studies were carried out to determine whether the production of FAHFAs is regulated by ChREBP. FIG. 17 shows that FAHFA levels were increased ~6-fold in WAT of adipose-Glut4 overexpressing mice compared to wildtype (WT). FAHFA levels were reduced in WAT of ChREBP knockout (KO) mice and when adipose-Glut4 overexpressing mice were bred with ChREBP KO mice, the elevated FAHFA levels were markedly reduced (FIG. 17). In serum of ChREBP KO mice, levels of the 2 major isomers of FAHFAs were reduced by 50-60%. This indicated that FAHFA synthesis and/or degradation is linked to ChREBP and that the beneficial metabolic effects of ChREBP-induced lipogenesis in WAT could be mediated, at least in part, by FAHFAs. The physiologic regulation of FAHFAs was investigated. The two major FAHFA isomers in serum are reduced by fasting and rapidly restored or increased by refeeding.

Example 3

PAHSA Levels in Serum from Insulin-Resistant Human Subjects.

Since the FAHFAs were first found to be elevated in diabetes-resistant mouse model (AG4OX mice), it was important to determine whether FAHFA levels correlated with insulin sensitivity in a well-defined cohort of human subjects. Samples of human serum were obtained from a cohort of twenty-four Swedish volunteers at the Lundberg Laboratory for Diabetes Research. Eight of these volunteers were lean and insulin-sensitive, eight were lean but insulin-resistant, and eight were obese and insulin-resistant (FIG. 18). Subjects with a body mass index (BMI), calculated as their total mass in kilograms divided by the square of their height in meters, below 25 $kg/m^2$ were considered to be lean, and subjects with a BMI above 30 $kg/m^2$ were considered to be obese. The volunteers had fasted for 12 hours, after which their blood serum was sampled. In order to divide the cohort into insulin-sensitive and insulin-resistant groups, subjects underwent a hyperinsulinemic-euglycemic clamp study, which measures the rate of intravenous glucose infusion that is required to avoid a drop in blood sugar in response to intravenous infusion of insulin. Individuals that required a glucose-infusion rate above 15 mg/kg/min to maintain euglycemia were considered to be insulin-sensitive and subjects that could not tolerate a glucose infusion rate above 12 mg/kg/min were considered to be insulin-resistant.

Serum from these subjects was diluted with PBS buffer and extracted with chloroform-methanol using the protocol for serum extractions previously developed. PAHSA levels in these samples were analyzed by the isocratic LC-MS method used previously (FIG. 19) and described above. This method permitted higher throughput analysis while still resolving the PAHSA isomers. The results of this analysis showed that there was no significant difference between the groups in the levels of the major isomer, 10-PAHSA, nor was there a significant difference in the levels of a minor isomer, 12-PAHSA. Nevertheless, it was notable that this novel lipid class, identified in mouse adipose tissue, was found to be present in the serum of human subjects at levels similar to those found in mouse serum.

Strikingly, 5-PAHSA was detectable in serum from all of the insulin-sensitive subjects, was present in the serum of only some of lean insulin-resistant subjects, and was nearly entirely undetectable in serum from obese insulin-resistant subjects. Comparison of two representative LC-MS traces from a lean insulin-sensitive subject and an obese insulin-resistant subject illustrates the qualitative difference between the two samples (FIG. 20). These data suggested that 5-PAHSA may be an important serum marker of increased insulin sensitivity in humans.

Example 4

Chemical Synthesis of Biotin-X-9-HAS (Scheme 1).

9-Hydroxystearic was protected with 2,4'-dibromoacetophenone by the method developed by Zhang and colleagues [23] to give the esterified FAHFA. Mesylation of this compound set up the displacement of mesylate by sodium azide and was followed by reduction with zinc dust in glacial acetic acid. The zinc reduction step also removed the bromoacetophenone protecting group to give the fatty amino acid, which was filtered and used without further purification (crude yield: 0.27 g, 85% over three steps). To a solution of the fatty amino acid (25 mg, 0.083 mmol) in DMSO (4 mL) was added commercially available biotinamidohexanoyl-6-aminohexanoic acid N-hydroxysuccinimide ester (Biotin-X-NHS) (34 mg, 0.074 mmol) in the presence of triethylamine (40 uL) afforded Biotin-X-9-HSA, which was purified by reversed phase HPLC (3.5 mg, 6.6%). Calculated: m/z 637.4368 $[M-H]^-$, found: m/z 637.4363.

Example 5

FAHFA Effects on Insulin Secretion

Ins1 cells (FIG. 21) or primary rat islet cells (FIG. 22) were seeded in 24 well-plates [~106 cells/well]. At confluence, cells were incubated with Low Serum [2.5%] and Low Glucose [2.5 mM] media for 12 hours. Next, cells were incubated with KRB buffer for 1 h and stimulated with glucose in the presence of 5-PAHSA (FIG. 21) or 9-PAHSA (FIG. 21) for 45 min in KRB. At the end of the stimulation, 100 μL of media was collected and 10 μL was used to quantitate the amount of insulin released by ELISA. Treatment Conditions for FIGS. 21 and 22 were:

5-PAHSA or 9-PAHSA [Stock]=20.0 mM [10.76 mg/mL Methanol]

A] 1 uM=0.3 uL/6 mL [Amount of methanol/mL=0.05 uL]
B] 5 uM=1.5 uL/6 mL [Amount of methanol/mL=0.25 uL]
C] 10 uM=3.0 uL/6 mL [Amount of methanol/mL=0.50 uL]
D] 20 uM=6.0 uL/6 mL [Amount of methanol/mL=1.00 uL]

Results are summarized in FIGS. 21 and 22.

Example 6

Agonists for PPARs Increase 5PAHSA Levels in HepG2 Liver Cells

In this example, HepG2 cells were seeded in 6-well plates. At 80% confluence, cells were treated with two different concentrations [0.5 uM and 1.0 uM] of an agonist of PPAR α (WY14643), δ (CAY10592), or γ (Pioglitazone) for 48 hr in HepG2 media with 2.5% FBS. At the end of incubation, 500 uL of media was collected and the cells were collected in PBS for lipid extraction. Lipids were extracted from both media and cells to quantitate the FAHFA levels by Mass Spec. The results are summarized in FIGS. 23 and 24 for the cells and media, respectively. These results indicate that PPAR agonists stimulate FAHFA production in liver cells, and the FAHFAs are released into the media.

Example 7

FAHFA Effects on LPS Stimulated Cytokine Secretion and Maturation Status in Dendritic Cells Macrophage-related inflammation in adipose tissue contributes to obesity-induced insulin resistance. Wellen K E and Hotamisligil G S, *J. Clin. Invest.* 2003. The Experimental design used in this example is shown in FIG. 25 and is described further in the materials and methods. Results are shown in FIGS. 26A and 26B. These results demonstrate that 9-PAHSA blocks IL-12 production by LPS-activated dendritic cells and thus can likely be used to treat insulin resistance as well as other disorders mediated by the inflammatory cytokine cascade. Additional data is shown in FIGS. 35 and 36.

Generation and Treatment of Bone Marrow-Derived Dendritic Cells (BMDCs):

Mouse bone marrow cells were flushed from the femurs and tibiae. The red blood cells were eliminated and the cells plated at a density of $1.0\times10^6$ cells/mL in RBMI complete medium containing 10% FCS plus 20 ng/ml GM-CSF. The medium was replaced on day 4, and the cells were harvested on day 6 to obtain immature DCs. To obtain mature DCs, LPS was added to the cultures at a final concentration of 100 ng/mL on day 6, and the cells were cultured for an additional 24 h, as previously described by Macia, L., et al. Impairment of dendritic cell functionality and steady-state number in obese mice. *J Immunol* 177, 5997-6006 (2006), which is incorporated by reference in its entirety. To test the anti-inflammatory effects of 9-PAHSA, immature BMDC were treated with 9-PAHSA in a dose response dependent manner in the presence of 100 ng/mL of LPS. The activation status of the BMDCs was evaluated by measuring the expression of MHCII and co-stimulatory molecules using Flow Cytometry and by the production of pro-inflammatory cytokines (IL-6, TNF, IL-12 and IL-1β) which was assessed by ELISA.

Example 8

Probing the Hydrolysis of FAHFAs in Vivo.

Using a FAHFA probe that was labeled on both fatty acyl chains, the significance of CEL hydrolysis of the FAHFAs in vivo was studied. On its own, [$^{13}$C]-9-PAHHA had a unique molecular mass that could be targeted by mass spectrometer without concern for interfering signal from naturally occurring FAHFAs (i.e., "bio-orthogonal"), permitting us to assess only the effects on the FAHFAs that were introduced into the system. Upon hydrolysis [$^{13}C_{16}$]-9-PAHHA liberated two labeled fatty acids: [$^{13}C_{16}$]-PA and the odd-chain 9-HHA. Each had a bio-orthogonal molecular mass, permitting specific targeting by mass spectrometry. Since the 17-carbon hydroxy fatty acid was not naturally occurring, re-acylation of this compound—that is, exchange of [$^{13}C_{16}$]-PA for a naturally occurring fatty acyl chain on the 9-HHA backbone—was evidence that [$^{13}C_{16}$]-9-PAHHA was hydrolyzed and re-esterified.

The experimental design used to confirm that CEL was relevant to FAHFA hydrolysis in vivo used [$^{13}C_{16}$]-9-PAHHA as a molecular probe (FIG. 28). It was reasoned that feeding mice labeled FAHFA in vegetable oil would most closely mirror the natural situation in which CEL is released from the pancreas, where it is most abundant, in response to ingestion of lipids. This way CEL would likely encounter the labeled FAHFA in the duodenal lumen. By analogy with existing pharmacologic therapies aimed at preventing triglyceride absorption, inhibition of CEL was expected to lead to lower absorption of FAHFAs. Since the initial destination of lipids taken up by enterocytes is the bloodstream, it was expected to observe not only lower levels of [$^{13}$C]-9-PAHHA itself, but also lower levels of its downstream metabolites such as 9-HHA and products re-esterified with palmitoyl or oleoyl acyl chains such as 9-PAHHA or 9-OAHHA.

Visualization of in Vivo Inhibition of CEL by WWL92.

To establish that WWL92 was capable of inhibiting CEL in vivo, mice were fasted overnight and an intraperitoneal injection of WWL92 was administered at doses of 0, 3, or 30 mg/kg. After either 1 or 2 hours, the mice were sacrificed and the pancreas was harvested. Membrane lysates of the pancreas tissue were prepared, and they were first reacted with either WWL92 (20 μM) or DMSO to verify that WWL92 inhibited CEL ex vivo. Reaction with an activity-based probe (FP-Rh), followed by separation of proteins by SDS-PAGE, permitted fluorescent detection of FP-Rh-labeled proteins. A decreased band intensity at 75 kD indicates that a greater proportion of CEL was pre-labeled by the CEL inhibitor during incubation in the body and was not available for labeling by FP-Rh.

The results show that WWL92 was indeed capable of inhibiting CEL in vivo (FIG. 29). There was a dose-dependent decrease in CEL band intensity that was also time-dependent. The WWL92-treated bands decreased in intensity when comparing mice that were sacrificed after two hours rather than one hour. Pancreas membrane lysates from vehicle-treated mice were reacted with WWL92 ex vivo and CEL activity was nearly extinguished in these samples, verifying that WWL92 was active against CEL. Importantly, after two hours mice treated with 30 mg/kg WWL92 were devoid of CEL activity in the pancreas. This dose and timepoint served as an appropriate guidepost for the subsequent gavage experiment with WWL92-treated mice.

Gavage of WWL92-Treated Mice with Double-Labeled FAHFA.

Fasted wild type mice were injected intraperitoneally with 40 mg/kg WWL92 or vehicle. After 30 minutes all of the mice (n=3-4) were oral-gavaged with 0.1 mL refined olive oil containing 0.15 mg [$^{13}$C]-9-PAHHA. Three hours later, the mice were sacrificed and plasma was harvested and flash frozen on liquid nitrogen. Extraction of serum lipids with chloroform-methanol-PBS buffer was performed using [$^{13}$C]-9-PAHSA as an internal standard to control for any differences in extraction efficiency.

The results of the experiment support the hypothesis that CEL is important in FAHFA hydrolysis and absorption in vivo. Significantly both lower plasma levels of [$^{13}$C]-9-PAHHA in the WWL92-treated mice and markedly lower levels of the 9-HHA hydrolysis product were observed (FIG. 30). This indicated that WWL92 had successfully inhibited CEL hydrolysis of FAHFAs. Importantly, it was also observed that lower plasma levels of the re-esterified 9-PAHHA and 9-OAHHA products in the WWL92-treated mice (FIG. 31), which confirmed the observation of lower 9-HHA levels and underscored the parallels between the enteric absorption of FAHFAs and other natural lipids such as triglycerides (FIG. 32).

Example 9

Insulin Release from Primary Human Islet Cells

Two human donors provided cells used in these studies. Donor1 was a 48 year old female, 5'0", 157 lbs, with a BMI of 30.5, HbA1C was 5.8, who died from a stroke, but it was witnessed and she had no downtime. Islets were 80% pure and 95% viable. After arrival, islets were incubated overnight in human islet media before stimulation with glucose in presence and absence of 5-PAHSA (lipid A-5). Note 1 IU of Human Insulin=6 nmol=34.8 μg Insulin.

Human islets were divided into ten groups [100 islets per condition]

A] Low glucose [2.5 mM]; B] High glucose [20.0 mM]; C] Low glucose [2.5 mM]+2.5 μL/mL Methanol; D] High glucose [20.0 mM]+2.5 μL/mL Methanol; E] Low glucose+20 μM Lipid A-5; F] High glucose+20 μM Lipid A-5; G] Low glucose+50 μM Lipid A-5; H] High glucose+50 μM Lipid A-5.

Islets were cultured overnight in Human Islet media and next day incubated with KRB buffer for 4 h prior to glucose stimulation.

Following KRB incubation, islets were stimulated with glucose [2.5 mM & 20.0 mM] in the presence and absence of Lipid A-5 [20 & 50 μM] for 45 min At the end of glucose stimulation the amount of insulin released [μ IU/mL] into the media was measured using Human Insulin ELISA kit. And the insulin content from the islets were extracted to express insulin released into the media as μ IU/mL/islet content.

Results for Donor 1 are shown in FIG. 37.

Donor 2 was a 44 year old male, 183 cm, 176 lbs, with a BMI of 23.9, HbA1C was 5.0, died from a stroke, but it was witnessed and he had no downtime. Islets were 85% pure and 95% viable. After arrival, islets were incubated overnight in human islet media before stimulation with glucose in presence and absence of 5-PAHSA (Lipid A-5).

Human islets were divided into ten groups [75 islets per condition]: A] Low glucose [2.5 mM]; B] High glucose [20.0 mM]; C] Low glucose [2.5 mM]+2.5 μL/mL Methanol; D] High glucose [20.0 mM]+2.5 μL/mL Methanol; E] Low glucose+20 μM Lipid A-5; F] High glucose+20 μM Lipid A-5.

Islets were cultured overnight in Human Islet media and next day incubated with KRB buffer for 4 h prior to glucose stimulation.

Following KRB incubation, islets were stimulated with glucose [2.5 mM & 20.0 mM] in the presence and absence of Lipid A-5 [20 μM] for 45 min.

At the end of glucose stimulation the amount of insulin released [μ IU/mL] into the media was measured using Human Insulin ELISA kit. And the insulin content from the islets were extracted to express insulin released into the media as μ IU/mL/islet content.

Results for Donor 2 are shown in FIG. 38.

Example 10

Additional FAHFA Functional Studies

Figure 39:
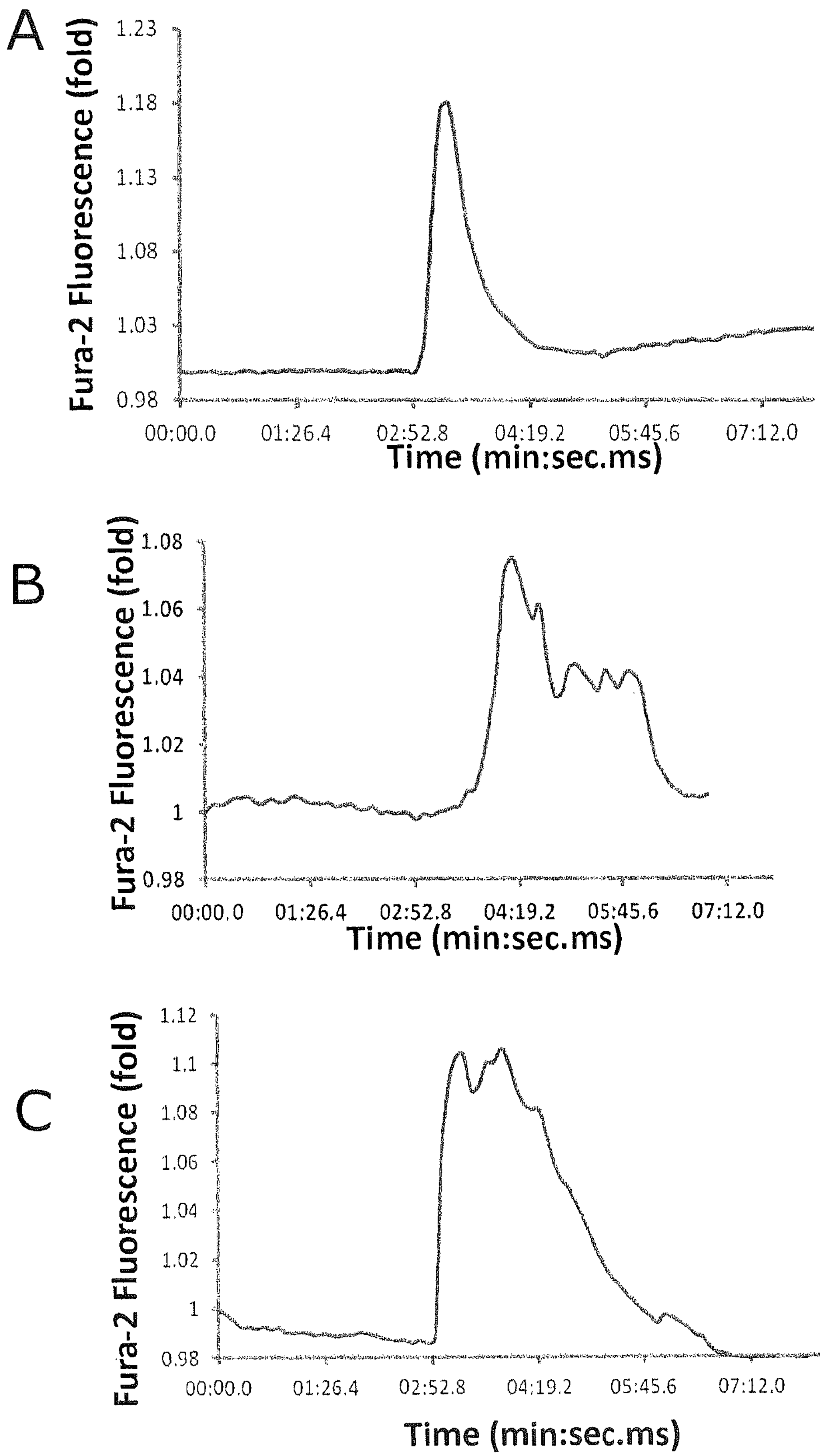

For the experiments summarized in FIG. 39 the method is: Cells grown on collagen coated glass slides were preloaded with the calcium indicator, FURA2, for 60 minutes. Buffer containing either FAHFAs or vehicle was incubated with cells for a period of 3 minutes followed by washout with buffer alone. FURA2 fluorescence, an indicator of Calcium mobilization, was monitored continuously before and during the addition of compounds and throughout the washout period. Results were analyzed with metamorph software. Calcium Flux in STC-1 (intestinal enteroendocrine) cells in the absence of extracellular calcium (calcium free buffer). Ligands were injected after 3 minutes and washed out after an additional 3 minutes. The data presented is the average fold change in Fura2 fluorescence for 10 individual STC-1 cells in the same field.

DMSO control had no effect. Top panel is linoleic acid, a positive control. Middle panel 9-PAHSA (100 uM). Bottom panel 5-PAHSA (100 μM). These experiments were done in the absence of extracellular calcium. Calcium flux was also stimulated by FAHFAs in the presence of extracellular calcium indicating that FAHFAs stimulate influx of extracellular calcium into the cell as well as release from the endoplasmic reticulum.

For the experiments summarized in FIG. 40, STC-1 cells were incubated with 9-PAHSA, 5-PAHSA or 9-OAHSA at the indicated concentrations. Cells were harvested and lysed and proteins were separated by SDS PAGE and transferred onto nitrocellulose filters. The phosphorylation of ERK and the amount of total ERK was determined by immunoblotting with antibodies specific for total or phosphor-ERK. DMSO was the control. For ERK phosphorylation, cells were serum deprived overnight and stimulated with FAHFAs or vehicle as indicated for 15 minutes followed by lysis in RIPA buffer and analysis by SDS-PAGE For the experiments summarized in FIG. 41 STC-1 cells were incubated with vehicle (DMSO), 9-PAHSA, 5-PAHSA or 9-OAHSA at the indicated concentrations or lineolic acid (100 uM) as a positive control. Media was harvested and GLP-1 was measured by ELISA.

For the experiments summarized in FIG. 42, the same protocol as described for FIG. 41 was used, except in this experiment a time course was performed. For both FIG. 41 and FIG. 42, for GLP-1 secretion STC1 cells were washed 3× with serum free culture media followed by stimulation with FAHFAs or vehicle at the indicated concentrations and timepoints. Levels of active GLP-1 were measured by ELISA.

For the experiments summarized in FIGS. 43-45, the fragment based GPCR assay from DiscoveRx (PATHHUNTER® β-Arrestin assay) was used to as per manufacturer's instructions to determine activation of specific GPCRs as indicated in FIGS. 43-45.

Example 11

FAHFA Analysis in Plasma of Insulin-Sensitive (n=12) and Insulin-Resistant (n=9) Female Subjects Before and During Hyperinsulinemic Euglycemic Clamp A total of 21 non-diabetic apparently healthy Caucasian women were recruited on the basis of the following inclusion criteria: (1) age 18-60 years, and (2) no known acute or chronic disease other than obesity. Physical and biochemical characteristics of the study subjects is shown in the Table 1. These subjects were from a different study from that summarized in Example 3.

TABLE 1

| | Insulin-sensitive | Insulin-resistant | p value |
|---|---|---|---|
| Number | 11 | 10 | — |
| Age (years) | 32 ± 3 | 40 ± 3 | NS |
| Body weight (kg) | 69 ± 4 | 90 ± 4 | <0.01 |
| BMI (kg/m$^2$) | 24.7 ± 1.1 | 32.7 ± 1.8 | <0.001 |
| Whole-body fat (%) | 28 ± 2 | 36 ± 1 | <0.001 |
| Fat mass (kg) | 20 ± 2 | 35 ± 4 | <0.01 |
| Waist-to-hip-ratio | 0.86 ± 0.01 | 0.91 ± 0.01 | <0.01 |
| Fasting plasma glucose (mmol/l) | 5.1 ± 0.1 | 5.6 ± 0.2 | <0.01 |
| Fasting serum insulin (mU/l) | 3 ± 1 | 10 ± 1 | <0.001 |
| Fasting serum C-peptide (nmol/l) | 0.4 ± 0.1 | 0.8 ± 0.1 | <0.001 |
| Fasting serum LDL cholesterol (mmol/l) | 2.2 ± 0.1 | 3.1 ± 0.1 | <0.01 |
| Fasting serum triglycerides (mmol/l) | 0.8 ± 0.1 | 1.4 ± 0.2 | <0.01 |
| Fasting serum HDL cholesterol (mmol/l) | 1.4 ± 0.1 | 1.3 ± 0.1 | <0.001 |
| Fasting serum adiponectin (mg/l) | 18 ± 2 | 12 ± 1 | <0.01 |

Whole body insulin sensitivity was measured using the euglycaemic insulin clamp technique (insulin infusion rate 1 mU kg-1 min-1 for 6 h) after an overnight fast. The women were divided into insulin sensitive and insulin-resistant groups on the basis of their rate of whole-body insulin sensitivity. Normoglycemia was maintained by adjusting the rate of a 20% glucose infusion based on plasma glucose measurements. Whole body insulin sensitivity was determined from the glucose infusion rate required to maintain normoglycaemia between 30 and 360 min. Hyperinsulinemic euglycemic clamp measurements were made at 0, 180, and 360 minutes. Markers of insulin resistance, including serum fasting insulin, C-peptide and triglyceride concentrations were higher and HDL cholesterol and adiponectin concentrations were lower in the insulin-resistant than in the insulin-sensitive group. Lipid extraction was performed by Folch's method (chloroform:methanol=2:1), and lipids were extracted from ~300 μL serum and plasma, and concentrated in 100 μL chloroform. Lipids were measured by MS with a gradient of Methanol:Water of (94:6) and an injection volume of 2 μl.

The levels of 5-PAHSA in plasma of insulin sensitive & insulin resistant were lower after clamp that at baseline (FIGS. 46 and 47A and 47B).

Experimentation also demonstrated that 5-PAHSA levels in human plasma in the fasting state correlated with insulin sensitivity measured by euglycemic hyperinsulinemic clamp studies, while 5-PAHSA levels correlated inversely with plasma triglycerides in the fasting state (FIG. 48).

Example 12

Specific PAHSA Isomers in WT and AG4OX Mice

Tissue Distribution of PAHSA Levels in Wild Type vs AG4OX Mice.

Investigation of the tissue distribution of PAHSAs in AG4OX and WT mice using a targeted MS approach revealed their presence in all the tissues analyzed. In WT mice, total PAHSAs levels were highest in brown adipose tissue (BAT) followed by subcutaneous (SQ) white adipose tissue (WAT), perigonadal (PG) WAT and liver (FIG. 49E). Total PAHSA levels in WT mice were very low in heart and gastrocnemius muscle (data not shown). In WT serum, total PAHSA levels were ~7 nM (FIG. 49E). In AG4OX mice, total PAHSA levels were most highly elevated (16-18 fold>WT) in SQ and PG WAT (FIG. 49E). PAHSA levels were also elevated ~70% in BAT. In contrast, PAHSA levels in liver of AG4OX mice were ~30% lower than WT. Total PAHSA levels were elevated 2.5-fold in serum from AG4OX mice (FIG. 49E). Thus, Glut4 overexpression in AT resulted in broad systemic regulation of PAHSAs with tissue-specific alterations. Furthermore, PAHSA levels vary >7-fold among tissues in WT mice.

Tissue Distribution of Specific PAHSA Isomers and Regulation in WT and AG4OX Mice.

Using the optimized LC/MS conditions, multiple peaks in the chromatograms for the PAHSAs were observed. Each peak was hypothesized to correspond to a different PAHSA isomer, in which the ester is connected to a different carbon of the hydroxy-fatty acid resulting in a branched lipid. To determine the exact position of the ester, high collisional energy tandem MS was utilized. [8]. Fragmentation of the adipose-derived PAHSAs produced two ions at 127 and 155 (FIG. 49B) that indicated that the ester is at the $9^{th}$ carbon of the HSA (FIG. 49C). This isomer is referred to as 9-PAHSA which was confirmed by chemical synthesis and co-elution with $^{13}$C-9-PAHSA (FIG. 50A). PAHSAs with branched esters at carbons 5, 7, 8, 10, 11, 12 and 13 were discovered and verified by comparison to synthetic standards (FIG. 50A). Thus, there are at least 8 PAHSA isomers all of which contain a branched ester linkage. Complete separation of all PAHSA isomers was achieved, except for 13- and 12-PAHSA (FIG. 50A), which were added together in subsequent data sets.

Determination of which PAHSA isomers are upregulated similarly in WAT and serum of AG4OX mice was used as an initial clue to which ones may have biologic activities that could contribute to insulin sensitivity. In WT serum, 13/12-, 11-, 10-, 9-, and 5-PAHSA are present at 0.4-2.5 nM which is the range for known signaling lipids. In WT WAT and BAT, 9-PAHSA is the most abundant isomer (FIG. 50B). 13/12-, 11- and 10-PAHSA are present at 20-30% of the 9-PAHSA levels and 8-, 7-, and 5-PAHSA are present at substantially lower concentrations (FIG. 50B). Surprisingly, liver which is also a lipogenic tissue, has only 13/12- and 9-PAHSAs which were present at similar concentrations to each other and to the levels of these isomers in WAT (FIG. 50B). In AG4OX mice, all PAHSA isomers are elevated in serum, SQ and PG WAT and BAT with 9-PAHSA being the most highly upregulated. In contrast, in AG4OX liver, PAHSAs were reduced compared to WT. These data revealed that individual PAHSA isomers were coordinately upregulated in AG4OX WAT and BAT which may result from the effect of increased Glut4 to induce ChREBP and lipogenesis in these tissues. However, PAHSAs were reduced in AG4OX liver indicating tissue-specific mechanisms for regulating uptake, synthesis or degradation.

This was further indicated by the tissue distribution of specific PAHSA isomers in WT mice. 13/12- and 9-PAHSAs are present in all tissues from WT mice that were examined (FIG. 50*c*). 9-PAHSA is more abundant in AT than liver while 13/12-PAHSA is not. In contrast to 13/12- and 9-PAHSA, 5-PAHSA was restricted to AT, kidney and serum.

Physiologic Regulation of PAHSAs in WT Mice with Fasting.

To understand the physiologic role of PAHSAs, regulation in different tissues and in serum of WT mice was examined in response to fasting (FIG. 50D). In the fed state, total PAHSA levels were highest in BAT. Levels in SQ and PG WAT are slightly lower and levels in liver, pancreas and were are substantially lower than AT (FIG. 50D). Fasting increased PAHSAs 2-3-fold in PG and SQ WAT and kidney and 65% in pancreas but did not alter the levels in BAT, liver or serum (FIG. 50D). Hence, total PAHSA levels undergo tissue-specific regulation with fasting (FIG. 50D).

The physiologic regulation of PAHSA isomers with fasting was investigated (FIG. 50E). Although total PAHSA levels were unchanged in serum of fasted mice (FIG. 50D), specific isomers (10-, 9- and 5-PAHSA) were modestly decreased (FIG. 50E). In SQ and PG WAT, most of the isomers (13/12-, 11-, 10-, 9- and 8-PAHSA) including the more abundant ones were increased with fasting while 7- and 5-PAHSA were unchanged. Fasting had no effect on any PAHSA isomer in BAT or liver while all isomers were upregulated in kidney. In pancreas, 11- and 9-PAHSA were increased with fasting while 13/12- and 7-PAHSA were unchanged. Thus, PAHSA isomers undergo tissue-specific and isomer-specific physiologic regulation with fasting. The abundance of different PAHSA isomers in the fasted state differed by 60-fold in a given tissue (compare 9- with 5-PAHSA in SQ WAT) (FIG. 50D). Based on these results, fasting likely regulates pathways involved in synthesis, degradation and/or release of specific PAHSA isomers.

Example 13

Regulation of PAHSAs in Obesity and Insulin Resistance

To determine whether PAHSA levels are altered in insulin resistant states, the levels were investigated in mice with high fat diet (HFD)-induced obesity compared to chow-fed mice (FIG. 51). After 9 weeks of HFD, mice were obese and diabetic (determined by GTT) (FIG. 55). HFD had differential effects on specific PAHSA isomers. 5- and 13/12-WAT. Strikingly, 10-, 9-, 8-, and 7-PAHSA were increased in PG WAT of HFD-fed mice while most of these isomers were decreased in SQ WAT and BAT and unchanged in serum (FIG. 51A). 13/12- and 9-PAHSA were also decreased in liver. These studies demonstrated: 1) 5-PAHSA and 13/12-PAHSA were consistently reduced in AT depots with HFD while other PAHSA isomers had opposite regulation among the depots (PG WAT versus SQ WAT and BAT) (FIG. 51A); and 2) Of the five isomers in serum, only 13/12- and 5-PAHSA were reduced with HFD (FIG. 51A). Thus, PAHSAs undergo isomer-specific and tissue-specific regulation under insulin-resistant conditions (e.g., HFD-induced obesity) in WT mice.

PAHSAs are Present in Food

To determine whether the changes observed in PAHSA levels in physiologic or pathophysiologic states could result from differences in dietary PAHSA intake, PAHSA levels in rodent and human foods were measured. In chow and HFD, we found five of the seven isomers that were present in mouse AT, 13/12-, 11-, 10-, 9- and 8-PAHSA, but not 7- and 5-PAHSA. However, the relative abundance was strikingly different from AT or serum with 10-PAHSA being most abundant in both diets (FIG. 51B). Levels of all these isomers were substantially lower in HFD than chow (FIG. 51B). Given the fact that PAHSAs increase in WAT during fasting, regulation of tissue PAHSA levels did not simply reflect dietary intake. Similarly, the abundance of PAHSA isoforms in serum and tissues (FIG. 50C) did not correlate with predominant isomers in chow (FIG. 51B), suggesting that PAHSAs present in tissues were synthesized endogenously. The fact that 5-PAHSA was not present in mouse chow or HFD (FIG. 51B) further supports this notion. Because of the presence of PAHSA isomers in mouse food common human food types (FIG. 51C) were investigated and PAHSAs were found in all human foods tested with different isomer distributions and abundance.

PAHSAs are Present in Humans and Levels are Reduced with Insulin Resistance

To determine whether PAHSAs are present in humans and are regulated in disease states, PAHSA isomers were measured in serum and SQ WAT from insulin-sensitive and insulin-resistant non-diabetic humans. Subjects were middle-aged and the BMI was increased in 5 out of 6 insulin-resistant participants. Insulin resistance was demonstrated by a 61% reduction in glucose infusion rate during a euglycemic hyperinsulinemic clamp. Characteristics of the subjects in this study are summarized in Table 2, below.

TABLE 2

Metabolic characteristics of human participants. All participants were nondiabetic. Glucose infusion rate (GIR) was determined by euglycemic-hyperinsulinemic clamp as described previously (Laakso et al., 2008). Lean body mass (LBM) was determined by bioimpedance analysis. Blood was drawn after an overnight fast. Except for gender, data are expressed as means +/− SE.

| Clinical Classification | No. of Subjects (M/F) | Age (yr.) (Range) | Body Weight (kg) (Range) | BMI ($kg/m^2$) (Range) | GIR(mg/kg LBM per min) (Range) | Serum Triglycerides (mmol/L) (Range) | FFAs (mmol/L) (Range) |
|---|---|---|---|---|---|---|---|
| Insulin Sensitive | 7 (1/6) | 41.6 ± 3.0 (26-49) | 70.6 ± 2.2 (63.3-78.4) | 24.1 ± 0.7 (22.5-28.3) | 14.0 ± 1.1 (10.43-19.16) | 1.0 ± 0.2 (0.73-2.00) | 0.47 ± 0.1 (<0.2-0.66) |
| Insulin Resistant | 6 (3/3) | 45.4 ± 3.8 (26-53) | 98.2 ± 6.2 (74.7-118.1) | 30.5 ± 1.2 (25.8-35.3) | 5.4 ± 0.6 (2.7-7.20) | 1.2 ± 0.2 (0.52-2.00) | 0.51 ± 0.03 (<0.2-0.66) |
| p value | | | 0.0066 | 0.00026 | <0.0001 | 0.51 | 0.588 |

PAHSAs were downregulated in HFD mice in PG and SQ WAT, BAT and serum (FIG. 51A) although the difference did not reach statistical significance for 13/12-PAHSA in PG Fasting serum triglycerides and free fatty acids were not different between groups. Total PAHSA levels were reduced ~40% in serum of insulin-resistant humans (FIG. 52A). In serum of both insulin-sensitive and -resistant humans, 9- and 10-PAHSA are the most abundant and 13/12- and 5-PAHSAs are present at ~⅕ of these concentrations. In insulin-resistant people, serum levels of all PAHSAs except 9-PAHSA are reduced by 40-55% compared to insulin-sensitive people (FIG. 52A). Serum concentrations of total PAHSAs and all isomers correlated remarkably strongly with insulin sensitivity measured by clamp (FIG. 52B).

In human SQ WAT, total PAHSAs are reduced ~70%. 13/12-, 11-, 10-, 9-, and 5-PAHSA isomers were detected, however the levels of 11-PAHSA were unquantifiable. 9-PAHSA levels were higher than all other isomers (FIG. 52C) similar to mouse SQ WAT (FIGS. 50B, 50D and 51A). 13/12-, 10-, 9- and 5-PAHSA concentrations in SQ WAT of insulin-resistant people were 60-73% lower than in insulin-sensitive people (FIG. 52C). Concentrations of total PAHSAs and of 9- and 5-PAHSA, but not other isomers, in WAT correlated highly with insulin sensitivity (FIG. 52D). Serum PAHSA levels correlated with WAT PAHSA levels only for 5-PAHSA (FIG. 52E).

In summary, all PAHSA isomers that were detected were reduced in SQ WAT in insulin-resistant subjects and all but one PAHSA isomer are reduced in serum from these subjects. Furthermore, PAHSA levels in serum and WAT correlated highly with whole body insulin sensitivity. These effects paralleled the effects in diet-induced obese mice in which all PAHSA isomers were reduced in SQ WAT, and 13/12- and 5-PAHSA were lower in serum compared to chow-fed mice (FIG. 51A). This demonstrated that the regulation of PAHSAs and their inverse correlation with insulin resistance is conserved between mice and humans.
PAHSAs Acutely Improve Glucose Tolerance and Insulin Sensitivity Since levels of all PAHSA isomers in SQ WAT and some in serum correlated positively with insulin sensitivity, administration of PAHSAs was examined to see whether they could improve glucose tolerance and insulin-sensitivity in insulin-resistant obese mice. 9- and 5-PAHSA were selected for the following reasons: 1) 9-PAHSA was the most abundant form in PG and SQ WAT and BAT in WT mice and in SQ WAT of humans (FIG. 52C). 2) 9-PAHSA is the most strongly upregulated in serum and WAT of insulin-sensitive AG4OX mice (FIG. 50B) and was down-regulated (along with other isomers) in WAT of insulin-resistant humans (FIG. 52C). 3) 5-PAHSA was the most consistently downregulated in all adipose depots and in serum of insulin-resistant mice (FIG. 51A) and in WAT and serum of insulin-resistant humans. Oral gavage of 5-PAHSA resulted in a transient 3-5-fold increase in serum 5-PAHSA levels in mice on chow and HFD (FIG. 56). As shown in FIG. 51A, baseline 5-PAHSA levels were 50-80% lower in HFD-fed mice compared to chow-fed mice and 5-PAHSA gavage more than restored the levels (FIG. 56). The post-gavage elevation of serum 5-PAHSA levels in both chow and HFD-fed mice was similar to the elevation in serum of AG4OX mice (FIG. 50B and FIG. 56). This indicated that PAHSAs are absorbed orally and this route of administration can be used to increase PAHSA concentrations for in vivo metabolic studies.

Acute oral administration of 5- or 9-PAHSA in insulin-resistant high-fat fed mice lowered basal glycemia at 30 minutes after PAHSA administration (FIG. 53A). Subsequently, glucose was administered and improved glucose tolerance was observed in PAHSA-treated mice with reduced area under the glucose excursion curve (FIG. 53A). 5- or 9-PAHSA also lowered baseline glycemia 2.5-3 hours after administration and resulted in improved insulin sensi-tivity with more than a doubling of the area above the insulin response curve. This was largely because of the initial effect to lower glycemia before insulin was administered (FIG. 53B).
PAHSAs Stimulate Insulin and GLP-1 Secretion Studies were conducted to determine whether the PAHSA effects to improve glucose tolerance resulted entirely from the increased insulin sensitivity or also from improved insulin secretion. Therefore, the effects of PAHSAs on glucose-stimulated insulin secretion were tested in vivo in aged (47 weeks old) chow-fed mice. 5-PAHSA improved glucose tolerance (FIG. 53C) concurrent with acute enhancement of insulin secretion 5 minutes after glucose administration (FIG. 53D). This may result from direct effects on insulin secretion or from stimulation of incretin secretion since GLP-1 levels were also increased in PAHSA-treated mice 5 minutes after glucose administration (FIG. 53E). Thus, PAHSAs acutely improve insulin sensitivity and glucose tolerance and stimulate GLP-1 and insulin secretion.

To determine whether the stimulation of insulin secretion is a direct effect of PAHSAs on pancreatic beta cells, islets from human donors were incubated with 5-PAHSA and measured glucose-stimulated insulin secretion. 5-PAHSA had no effect on insulin secretion at 2.5 mM glucose but augmented the insulin secretion response at 20 mM glucose (FIG. 53F). These data demonstrate that 5-PAHSA directly enhances glucose-stimulated insulin secretion in human islets. To determine whether PAHSAs directly stimulated GLP-1 secretion, the enteroendocrine cell line STC-1 was used. Both 5- and 9-PAHSA rapidly stimulated GLP-1 secretion from STC-1 cells in a dose-dependent manner (FIG. 53G). The effects are similar to those with α-linolenic acid (ALA) and the synthetic GPR120 ligand, GW9508 (FIG. 53G). Thus, the rapid effects of PAHSAs to augment glucose-stimulated insulin secretion may be both direct effects on pancreatic beta cells and indirect effects through GLP-1 secretion.
PAHSAs Enhance Insulin-Stimulated Glucose Transport and Glut4 Translocation by Activating GPR120

To further understand the mechanism(s) by which PAHSAs increase insulin sensitivity, their effects on glucose transport were tested in adipocytes. 9-PAHSA modestly increased glucose transport in the basal state and had an even greater effect at sub-maximal and maximal insulin concentrations (FIG. 54A). 5-PAHSA also enhanced insulin-induced glucose transport in adipocytes (FIG. 54B). Neither of the fatty acids that form the parent PAHSA structure, palmitic acid or hydroxystearic acid, alone improved insulin-stimulated glucose transport. In fact, chronic treatment with these FAs impaired insulin-stimulated glucose transport in adipocytes (data not shown). The effects of PAHSAs on insulin-stimulated glucose transport occurred with both acute (30 min) and chronic (2-6 day) treatment. PAHSAs did not alter total cellular Glut1 or Glut4 protein levels in adipocytes even after 6 days of incubation (data not shown).

An important mechanism by which bioactive lipids can influence biology is through binding to cell surface receptors such as GPCRs (Hara et al., 2013). The effect of 5- and 9-PAHSA on GLP-1 secretion is consistent with possible activation of GPCRs ([28]). Furthermore, effects of PAHSA on glucose transport and Glut4 translocation are similar to effects of omega (ω)-3 fatty acids which act through GPR120 ([28, 29]).

To determine if PAHSAs might activate GPCRs a panel of known lipid-activated GPCRs were screened. Both 9-PAHSA (FIG. 57A) and 5-PAHSA (data not shown) dose-dependently activated GPR120 which is known to be activated by ω-3 fatty acids and to a lesser degree by monounsaturated fatty acids [28, 29]). Activation of GPR120 by natural and synthetic ligands has been reported to increase glucose transport and Glut4 translocation in adipocytes ([29]). To test whether GPR120 mediates the effects of PAHSA to enhance insulin-stimulated glucose transport, siRNA was utilized to knockdown GPR120 in adipocytes. GPR120 siRNA resulted in >95% reduction in GPR120 gene expression in adipocytes (FIG. 57B) and completely reversed the enhanced effects of PAHSAs on insulin-stimulated glucose transport (FIG. 54B). These data demonstrate that GPR120 mediates the effects of PAHSAs on insulin-stimulated glucose transport.

To determine the mechanism for enhancement of glucose transport with PAHSAs the effects on insulin-induced Glut4 translocation to the plasma membrane were analyzed in adipocytes. In the absence of insulin, PAHSAs had no effect on Glut4 translocation (FIG. 54C). However, PAHSAs enhanced Glut4 translocation at submaximal and maximal insulin concentrations (FIGS. 54C-D). These data indicated that PAHSAs augment insulin-stimulated glucose transport by enhancing Glut4 translocation. Knock down of GPR120 in adipocytes completely blocked the effect of PAHSAs to augment insulin-stimulated Glut4 translocation (FIGS. 54C-D) at both sub-maximal and maximal insulin concentrations. This effect was observed with two different GPR120 siRNAs indicating that it is a specific "on target" effect. These data demonstrate that GPR120 mediates the effects of PAHSAs on insulin-stimulated Glut4 translocation.

The primers used in this study are provided below. Duplex sequences for mGPR120 RNAi and Non-targeting control RNAi:

```
GPR120 DUPLEX 1
MMC, RNAI.N181748.12.1-
5'-GGAGUUAACUUCAAGGAAAGCCCAC-3'
3'-UCCCUCAAUUGAAGUUCCUUUCGGGUG-5'

GPR120 DUPLEX 2:
MMC, RNAI.N181748.12.2-
5'-CCCAACCGCAUAGGAGAAAUCUCAT-3'
3'-CCGGGUUGGCGUAUCCUCUUUAGAGUA-5'

GPR120 DUPLEX 3
MMC, RNAI.N181748.12.3-
5'-GCAAAUUAAGGAAUGAUCGCUCAGT-3'
3'-GUCGUUUAAUUCCUUACUAGCGAGUCA-5'

Non-Targeting DUPLEX 3
5'-CGUUAAUCGCGUAUAAUACGCGUA-3'
3'-CAGCAAUUAGCGCAUAUUAUGCGCAUA-5'
```

qPCR Primer Sequences for mGPR120 and mTBP:

| Primer | Direction | Sequence (5'->3') | Length | Tm |
|---|---|---|---|---|
| mGPR120 | Forward | CTTCTGCGCGG ATTTGCTC | 19 | 61.8 |
| | Reverse | CCGCTCATTGT CATCACGTAGA | 22 | 62.1 |
| mTBP | Forward | CCCTATCACTC CTGCCACAC | 20 | 58.9 |
| | Reverse | ACGAAGTGCAA TGGTCTTTAGC | 22 | 59.2 |

Materials and Methods

For all cell culture experiments, FAHFAs were solubilized in DMSO at a concentration of 20 mM and further diluted in assay buffer or cell culture media to the working concentrations indicated for each assay. In all instances an equivalent volume of vehicle (DMSO) was added to control treatment groups.

Animal Studies.

AG4OX and AG4OX-ChREBP-KO mice were described previously [1, 24]. Briefly, the fat-specific human GLUT4 transgene was constructed using the fat-specific promoter/enhancer from the fatty acid-binding protein gene, aP2. The AG4OX mice used were raised at Beth Israel Deaconess Medical Center, Boston, Mass. and were on a FVB background. ChREBP-KO mice were on a C57BL/6J background. Age- and sex-matched wild type littermates were used as controls. Animals were kept on a 12-hour light, 12-h dark schedule and fed ad libitum unless specified otherwise. For tissue collection, animals were euthanized with carbon dioxide and their tissues were dissected, flash frozen with liquid nitrogen, and stored at −80° C. All animal care and use procedures were in strict accordance with the standing committee on the use of animals in research and teaching at Harvard University and at the Beth Israel Deaconess Medical Center Animal Research Facility.

Lipid Extraction from Serum or Plasma.

To a labeled 8 mL glass vial was added 0.9 mL phosphate-buffered saline, 1 mL methanol, and 2 mL chloroform with internal standards 5 nM [$^{13}C_{16}$]-9-PAHSA and 1 uM [$^{13}C_{16}$]-palmitic acid. After thawing serum or plasma samples at 4° C., 100 uL serum/plasma was transferred to the glass vial. The vial was capped with a PTFE-lined cap, shaken vigorously for 10 seconds, and inserted in a 50 mL conical tube. The samples were centrifuged at 3220×g for 5 min at 4° C. to separate the immiscible layers. The bottom organic layer was transferred to a fresh 4 mL glass vial and the volatiles were removed under a nitrogen gas stream, leaving a lipid residue that was stored at −80° C. For analysis by LC-MS, samples were reconstituted in 50 uL chloroform and 2 uL injection volumes were typically used.

Lipid Extraction from Animal Tissues.

A frozen section of animal tissue (50-100 mg) was quickly sectioned off with a clean razor blade, weighed on an analytical balance, placed in a 1.7 mL plastic tube, and kept on dry ice. To a cold Dounce tissue grinder was added 1 mL ice-cold PBS, 1 mL methanol, and 2 mL chloroform that contained 10 nM [$^{13}C$]-9-PAHSA internal standard. The tissue sample was added to the tissue grinder, which was kept on ice, and the tissue was homogenized with the high clearance "A" pestle (30-40 strokes). Adipose tissue was homogenized with the low clearance "B" pestle owing to its low connective tissue content. The mixture was carefully poured into a labeled 8 mL glass vial. The vial was loaded into a 50 mL plastic conical tube and centrifuged at 3200×g for 10 minutes at 4° C. The bottom organic layer was transferred to a clean 4 mL glass vial using a Pasteur pipet and the volatiles were evaporated under a nitrogen gas stream. The lipid residue was stored at −80° C. and was reconstituted in 200-500 uL chloroform for MS analysis, with injection volumes of 10-30 uL for injection on 4.6 mm diameter columns and 1-3 uL for injection on 2.1 mm diameter columns.

Analysis by QQQ Mass Spectrometry.

Analysis of FAHFAs was performed in negative mode on an Agilent 6410 triple quadrupole mass spectrometer (QQQ-MS). For targeted profiling experiments, analysis was performed in multiple reaction monitoring mode, and the precursor ion and product ion targeted for each FAHFA species is detailed in Table 3. For FAHFAs, the fragmentor voltage was set to 180 V and the collision energy was 30 V. Dwell times for quantitated species ranged from 150-250 ms, and the cycle time did not exceed 1000 ms.

TABLE 3

| FAHFA name | Acyl carbons:double bonds | Fatty Acyl Group | Hydroxy Fatty Acid | Parent ion | MRM product ion |
|---|---|---|---|---|---|
| POHPA | C32:1 | palmitoleic acid | hydroxypalmitic acid | 507.4 | 253.2 |
| PAHPA | C32:0 | palmitic acid | hydroxypalmitic acid | 509.5 | 255.2 |
| OAHPA | C34:1 | oleic acid | hydroxypalmitic acid | 535.5 | 281.2 |
| POHSA | C34:1 | palmitoleic acid | hydroxystearic acid | 535.5 | 253.2 |
| PAHSA | C34:0 | palmitic acid | hydroxystearic acid | 537.5 | 255.2 |
| OAHSA | C36:1 | oleic acid | hydroxystearic acid | 563.5 | 281.2 |
| [$^{13}$C]-PAHSA | C34:0 | [$^{13}C_{16}$]-palmitic acid | hydroxystearic acid | 553.5 | 271.3 |

Analysis of free fatty acids by QQQ-MS was performed in selected ion monitoring (SIM) mode with the fragmentor voltage set to 150 V in negative mode and dwell times of 25 ms for each ion. Selected ions were m/z 227.2, 253.2, 255.2, 271.3, 277.2, 279.2, 281.2, 283.3, 301.2, 303.2, 309.3, and 327.2 for free fatty acid ions C14:0, C16:1, C16:0, [$^{13}C_{16}$]-C16:0, C18:3, C18:2, C18:1, C18:0, C20:5, C20:4, C20:1, and C22:6, respectively.

Chromatographic Conditions.

The QQQ-MS system was connected to an Agilent 1200 Binary Pump. For analyses of total PAHSA content without separation of PAHSA isomers (FIG. 29), a Gemini C18 reversed phase column (5 um, 4.6×50 mm, Phenomonex) and a C18 reversed phase guard column (3.5 um, 2 mm×20 mm, Western Analytical) was used for LC-MS analysis in negative mode. Mobile phase A consisted of a 95:5 water: methanol mixture and mobile phase B consisted of 60:35:5, 2-propanol:methanol:water, both containing 0.1% ammonium hydroxide. An Agilent 1200 series binary pump was set to a flow rate was 0.1 mL/min for the first 5 min followed by 0.4 mL/min for the remainder of the gradient. At 5 min, concomitant with the increase in flow rate, the gradient was increased from 0% B to 20% B. The gradient increased linearly to 100% B at 45 min, followed by an 8 minute wash at 0.5 mL/min with 100% B before re-equilibrating the column with 0% B for 7 min.

Targeted LC/MS Analysis of FAHFAs

Lipidomic analysis was performed using an Agilent 6220 ESI-TOF fitted with an electrospray ionization (ESI) source, a capillary voltage of 3500 kV and fragmentor voltage of 100 V. A Gemini C18 reversed phase column (5 μm, 4.6×50 mm, Phenomonex) and a C18 reversed phase guard column (3.5 μm, 2×20 mm, Western Analytical) was used for LC-MS analysis in negative mode. In positive mode, a Luna C5 reversed phase column (5 μm, 4.6×50 mm, Phenomonex) was used together with a C4 reversed phase guard column (3.5 μm, 2×20 mm, Western Analytical). The drying gas temperature was 350° C., flow rate 10 L/min and nebulizer pressure of 45 psi. Untargeted data were collected using a mass-to-charge range of m/z 100-1500.

Mass Spectrometry.

FAHFAs were measured on an Agilent 6410 Triple Quad LC/MS instrument via Multiple Reaction Monitoring (MRM) in negative ionization mode. A Luna C18(2) (Phenomenox, 00G-4251-B0) column (3 μm, 100 Å, 250×2.0 mm) was used with an in-line filter (Phenomenex, AF0-8497). The solvent was 93:7 methanol:water with 5 mM ammonium acetate (Aldrich, 372331) and 0.01% ammonium hydroxide (Sigma-Aldrich, 338818), and distinct PAHSA species were resolved via isocratic flow at 0.2 mL/min for 120 min. Each extracted and fractionated sample was reconstituted in 25 μL methanol and 10 μL was injected for analysis. Transitions for endogenous PAHSAs were m/z 537.5 m/z 255.2 (CE=30 V), m/z 537.5→m/z 281.2 (CE=25 V) and m/z 537.5→m/z 299.3 (CE=23 V), and transition for $^{13}$C-9-PAHSA was m/z 553.5→m/z 271.3 (CE=30 V). Fragmentor voltage and dwell time were 205 V and 300 ms, respectively, for each transition. Skimmer voltage was 15 V and ΔEMV was 400 V. MS1 resolution was set to wide and MS2 resolution to unit. Capillary voltage was 4.0 kV, drying gas temperature was 350° C., drying gas flow rate was 8 L $min^{-1}$ and nebulizer pressure was 35 psi. Identical gradient and instrument parameters were used for detection of all additional FAHFAs with the exception of dwell time, which was reduced to 30 ms to accommodate additional transitions. All FAHFA transitions are listed in Table 4.

MS Data Analysis.

Data analysis with XCMS was used to identify changing metabolites between samples. Raw data files from the TOF-MS were converted to mzXML files using the program mzStar for subsequent XCMS analysis. Samples were compared (i.e., AG4OX vs. WT) and differences were ranked according to statistical significance as calculated by an unpaired Student's t test. The data was then filtered based on a peak size (>5×10$^4$ counts) and statistical significance (p-value<0.05) prior to visual inspection of the remaining ions to ensure that the differences identified by XCMS were reflected in the raw data. Peak areas were normalized to the frozen wet mass of the extracted tissues and these corrected peak areas were used to calculate relative changes. For the volcano plot, data were obtained from the 60-minute profiling analysis in negative mode and the data were filtered based on retention time range (10-50 minutes) and abundance (>1×10$^5$ counts).

TABLE 4

| Transition | Precursor ion | Product ion | CE |
|---|---|---|---|
| POHPO_transition1 | 505.4 | 253.2 | 30 |
| POHPO_transition2 | 505.4 | 251.2 | 25 |
| POHPA_transition1 | 507.4 | 253.2 | 30 |
| POHPA_transition2 | 507.4 | 271.2 | 23 |
| PAHPO_transition1 | 507.4 | 255.2 | 30 |
| PAHPO_transition2 | 507.4 | 251.2 | 25 |
| PAHPA_transition1 | 509.5 | 255.2 | 30 |
| PAHPA_transition2 | 509.5 | 253.2 | 25 |
| POHOA_transition1 | 533.5 | 253.2 | 30 |
| POHOA_transition2 | 533.5 | 279.2 | 25 |
| OAHPO_transition1 | 533.5 | 281.2 | 30 |
| OAHPO_transition2 | 533.5 | 251.2 | 25 |
| PAHOA_transition1 | 535.5 | 255.2 | 30 |
| PAHOA_transition2 | 535.5 | 279.2 | 25 |
| OAHPA_transition1 | 535.5 | 281.2 | 30 |
| OAHPA_transition2 | 535.5 | 253.2 | 25 |
| POHSA_transition1 | 535.5 | 253.2 | 30 |
| POHSA_transition2 | 535.5 | 281.2 | 25 |

TABLE 4-continued

| Transition | Precursor ion | Product ion | CE |
|---|---|---|---|
| SAHPO_transition1 | 535.5 | 283.2 | 30 |
| SAHPO_transition2 | 535.5 | 251.2 | 25 |
| PAHSA_transition1 | 537.5 | 255.2 | 30 |
| PAHSA_transition2 | 537.5 | 281.2 | 25 |
| PAHSA_transition3 | 537.5 | 299.3 | 23 |
| $^{13}C$-9-PAHSA | 553.5 | 271.3 | 30 |
| SAHPA_transition1 | 537.5 | 283.2 | 30 |
| SAHPA_transition2 | 537.5 | 253.2 | 25 |
| OAHOA_transition1 | 561.5 | 281.2 | 30 |
| OAHOA_transition2 | 561.5 | 279.2 | 25 |
| OAHSA_transition1 | 563.5 | 281.2 | 30 |
| OAHSA_transition2 | 563.5 | 299.3 | 23 |
| SAHOA_transition1 | 563.5 | 283.3 | 30 |
| SAHOA_transition2 | 563.5 | 279.2 | 25 |
| SAHSA_transition1 | 565.5 | 283.3 | 30 |
| SAHSA_transition2 | 565.5 | 281.2 | 25 |

Biotin-FAHFA Pulldown.

The specific INS-1 cell line used was INS-1 832/13, a subclone of the original INS-1 cell line that stably expresses the human insulin gene [26]. The culture medium was RPMI-1640 with 11.1 mM D-glucose supplemented with 10% fetal bovine serum, 100 U/ml penicillin, 100 ug/ml streptomycin, 10 mM HEPES, 2 mM L-glutamine, 1 mM sodium pyruvate, 2 g/L sodium bicarbonate and 50 uM β-mercaptoethanol. INS-1 cells were cultured to 80% confluence in 150-mm dishes. Cells were scraped into PBS, washed with PBS, and resuspended in optimized lysis buffer (20 mM Tris-HCl, 2 mM EDTA, 500 mM NaCl, 0.1% Triton-X100). Cell suspension was sonicated with probe sonicator then centrifuged at 13,000×g for 15 minutes. Protein concentration was determined by BCA assay.

Paramagnetic avidin-linked polystyrene Dynabeads (Invitrogen) were washed twice and incubated in 0.1% fatty acid-free bovine serum albumin to while preparing cell lysates. Blocking buffer was removed by magnetic separation. Lysates were pre-cleared by diluting 2 mg protein sample to a final volume 1 mL with lysis buffer and incubating with 10 uL beads, after which the lysate was separated from the beads by magnetic separation. To the pre-cleared lysate was then added 400 uM 9-PAHSA or DMSO (2%) and the sample was incubated 2 hours at 4° C.

Following the blocking procedure, the beads were washed and resuspended in 1 mL of buffer containing 20 mM Tris-Cl, 2 mM EDTA and 150 mM NaCl. To this was added 5 uL biotin-X-9-HSA ("Bt-FAHFA") (100 uM in DMSO) or 5 ul of DMSO for control beads. The suspension was incubated for 2 hours at 4° C. The beads were washed three times with lysis buffer to remove any unbound Bt-FAHFA. Pre-cleared cell lysate (1 mL) was then added tubes containing the Bt-FAHFA-conjugated beads and suspension was incubated overnight at 4° C.

The next morning, the lysate supernatant containing unbound proteins was aspirated and the beads were washed four times with lysis buffer. Beads were resuspended in 30 uL 4×SDS-PAGE loading buffer and heated for 10 minutes at 95° C. to remove any bound target proteins from the beads. Each sample (25 uL) was then analyzed by SDS-PAGE on a 4-15% gradient gel, which was stained with Coomassie Blue.

Rac1 Activation Assay:

INS-1 cells were incubated overnight in a low serum (2.5% FBS)-low glucose (2.5 mM) containing medium, followed by an additional 1 h incubation in Krebs-Ringer bicarbonate buffer (KRB). At the end of the incubation cells were further stimulated with low glucose (5.0 mM) and high glucose (25 mM) for 30 min in the presence or absence of 9-PAHSA (50 μM; dissolved in DMSO) as indicated in the figure legend. An equal amount of DMSO was added to the vehicle. Lysates [~200 μg protein] were clarified by centrifugation for 5 min at 4800×g, and PAK-PBD [p21-activated kinase-binding domain] beads [20 μl] were added to the supernatant. The mixture was then rotated for 1 h at 4° C. and pelleted by centrifugation at 4,000×g for 3 min. The resulting pellet was washed once with lysis buffer followed by a rinse [3×] in wash buffer [25 mM Tris, pH 7.5, 30 mM MgCl2, 40 mM NaCl, and 150 mM EDTA]. Proteins in the pellet were resolved by SDS-PAGE and transferred onto a nitrocellulose membrane, and Western blotting method determined the relative abundance of activated Rac1. [Rac1 Activation Assay Biochem Kit (bead pull-down method); Catalog #BK035; Cytoskeleton Inc.]

Insulin Release Studies in INS1 Cells:

INS-1 cells were seeded in 24 well-plates [~$10^6$ cells/well] and at 80% confluence, were cultured overnight in RPMI 1640 medium containing 2.5 mM glucose and 2.5% fetal bovine serum supplemented with 100 IU/ml penicillin and 100 IU/ml streptomycin, 1 mM sodium pyruvate, 2-mercaptoethanol (50 μM) and 10 mM HEPES (pH 7.4). The cells were further incubated with Krebs-Ringer bicarbonate buffer, pH 7.4 for 1 h prior to stimulation with low (2.5 mM) or high glucose (25 mM) in the continuous presence or absence of 9-PAHSA or 5-PAHSA (dissolved in Methanol) at different concentrations mentioned in the figure legend for 45 min at 37° C. An equal amount of Methanol was added to the respective control. At the end of the stimulation supernatant was collected and insulin released into the medium was quantified by ELISA as per manufacturer's protocol. [Insulin (Rat) High Range Elisa Kit; Catalog #80-INSRTH-E01; Alpco Diagnostics].

Isolation of Pancreatic Islets for Insulin Release Studies:

Intact pancreatic islets were isolated from adult Sprague-Dawley rats using collagenase digestion method and separated from acinar tissue and debris on Ficoll gradient. Islets were hand-picked under a stereo-microscope twice to avoid contamination by acinar cells. All experiments, including isolation of pancreatic islets from normal Sprague-Dawley rats, were reviewed and approved by the Beth Israel Deaconess Medical Center Animal Care and Use Committee.

Insulin Release Studies in Rat Islets:

Isolated rat islets were cultured overnight in RPMI 1640 medium containing 2.5 mM glucose and 2.5% fetal bovine serum supplemented with 100 IU/ml penicillin and 100 IU/ml streptomycin, 1 mM sodium pyruvate, and 10 mM HEPES (pH 7.4). The islets were further incubated with Krebs-Ringer bicarbonate buffer for 1 h prior to stimulation with low (2.5 mM), high glucose (25 mM) or Palmitate (200 μM) in the continuous presence or absence of 9-PAHSA (100 μM; dissolved in DMSO) as mentioned in the figure legend for 45 min at 37° C. An equal amount of DMSO was added to the vehicle. At the end of the stimulation supernatant was collected and insulin released into the medium was quantified by ELISA as per manufacturer's protocol. The islets were lysed and protein content was measured and the amount of insulin released into the media was quantitated as ng/mL/μg of protein.

PPAR Agonist Studies:

HepG2 cells were seeded in 6-well plate. At 80% confluence, cells were treated with two different concentrations [0.5 μM and 1.0 μM] of PPAR α/δ/γ agonists for 48 h in HepG2 media containing 2.5% fetal bovine serum (PPAR α agonist—WY14643; PPAR δ agonist—CAY10592; PPAR γ agonist—Pioglitazone). At the end of incubation, 500 μL of media and the cells were collected in PBS. Lipids were extracted as per Folch Method from both media and cells to quantitate the FAHFA levels by Mass Spec. Briefly, chloroform and methanol were added to the media or cells in 2:1 ratio and sonicated for 2-3 min and centrifuged at 3000 rpm for 10 min at 4° C. The bottom chloroform layer containing lipids was taken and dried under Nitrogen. Calculated volume of chloroform is added to the dissolve the lipids and 2 μL of injection volume was used to analyze FAHFAs through Mass spec. [HepG2 Cells—ATCC #HB-8065].

Generation of Bone Marrow-Derived Dendritic Cells (BM-DCs)

Mouse bone marrow cells were flushed from the femurs and tibiae. The red blood cells were lysed, and the cells were plated at a density of $0.5\times10^6$ cells/mL in RPMI 1640 Low medium (Gibco, USA) containing 10% FCS (Gibco, USA) and 20 ng/mL GM-CSF. The medium was replaced on day 5, and the cells were harvested on day 6 to obtain immature DCs. To obtain mature DCs, LPS was added to the cultures at a final concentration of 100 ng/mL on day 6, and the cells were cultured for an additional 24 h.

9-PAHSA Affects on LPS Induced Dendritic Cells Maturation

The immature dendritic cells obtained in the day 6 were maturated with LPS in the presence of different concentrations of 9-PAHSA varying between 100 ng/mL to 20 ug/mL. The cells were maturated for 24 h and the maturation status analyzed by cytokine production and co-stimulatory molecules expression.

Flow Cytometry

The cells were analyzed by Multicolor Flow cytometry. The mature dendritic cells were harvested on day 7 and re-suspended in PBS supplemented with 2% FCS and stained with saturating amounts of the following mAbs: CD11c PE, MHCII APC, CD40 PE-Cy7, CD80 FITC and CD86 Percp. The cells were analyzed with an LSR II flow cytometer (BD) and FlowJo software.

Intracellular Cytokine Analysis and Foxp3 Staining

Maturated dendrite cells were analyzed for cytokine production by flow cytometry. For intracellular cytokine staining, $1\times10^6$ cells were stimulated in vitro for 4 h at 37° C. in 5% $CO_2$ with phorbol-12-myristate-13-acetate (PMA; 100 ng/ml) and ionomycin (1 μg/ml) and brefeldin A (1 μg/ml). The cells were then washed and stained with PE anti-CD11c and permeabilized using the BD Cytofix/Cytoperm Fixation/Permeabilization solution kit (BD Biosciences, USA). Intracellular staining was performed with APC-conjugated anti-IL-12p40 (Biolegend, USA).

ELISA Assay for IL-12p70

An ELISA assay (Biolegend) was used to measure the concentration of IL-12p70 protein in conditioned media from immature and mature BMDCs. This assay allowed for the detection of total IL-12p70 concentrations in the range of 15.6-1,000 pg/ml, and the results are expressed as pg/mL IL-12p70.

LITERATURE REFERENCES

1. Shepherd, P. R. et al. Adipose cell hyperplasia and enhanced glucose disposal in transgenic mice overexpressing GLUT4 selectively in adipose tissue. *J Biol Chem* 268, 22243-22246 (1993).
2. Gnudi, L., Shepherd, P. R. & Kahn, B. B. Over-expression of GLUT4 selectively in adipose tissue in transgenic mice: implications for nutrient partitioning. *Proc Nutr Soc* 55, 191-199 (1996).
3. Carvalho, E., Kotani, K., Peroni, O. D. & Kahn, B. B. Adipose-specific overexpression of GLUT4 reverses insulin resistance and diabetes in mice lacking GLUT4 selectively in muscle. *Am J Physiol Endocrinol Metab* 289, E551-561, (2005).
4. Saghatelian, A. et al. Assignment of endogenous substrates to enzymes by global metabolite profiling. *Biochemistry* 43, 14332-14339, doi:10.1021/bi0480335 (2004).
5. Homan, E. A., Kim, Y. G., Cardia, J. P. & Saghatelian, A. Monoalkylglycerol ether lipids promote adipogenesis. *J Am Chem Soc* 133, 5178-5181, (2011).
6. Folch, J., Lees, M. & Sloane Stanley, G. H. A simple method for the isolation and purification of total lipides from animal tissues. *J Biol Chem* 226, 497-509 (1957).
7. Smith, C. A., Want, E. J., O'Maille, G., Abagyan, R. & Siuzdak, G. XCMS: processing mass spectrometry data for metabolite profiling using nonlinear peak alignment, matching, and identification. *Anal Chem* 78, 779-787, doi:10.1021/ac051437y (2006).
8. Moe, M. K., Strom, M. B., Jensen, E. & Claeys, M. Negative electrospray ionization low-energy tandem mass spectrometry of hydroxylated fatty acids: a mechanistic study. *Rapid Commun Mass Spectrom* 18, 1731-1740, doi:10.1002/rcm.1545 (2004).
9. Muccioli, G. G. & Stella, N. An optimized GC-MS method detects nanomolar amounts of anandamide in mouse brain. *Anal Biochem* 373, 220-228, (2008).
10. Cravatt, B. F. et al. Functional disassociation of the central and peripheral fatty acid amide signaling systems. *Proc Natl Acad Sci USA* 101, 10821-10826, (2004).
11. Bachovchin, D. A. et al. Superfamily-wide portrait of serine hydrolase inhibition achieved by library-versus-library screening. *Proc Natl Acad Sci USA* 107, 20941-20946, (2010).
12. Gazzana, G. & Borlak, J. An update on the mouse liver proteome. *Proteome Sci* 7, 35, (2009).
13. Bachovchin, D. A. et al. Superfamily-wide portrait of serine hydrolase inhibition achieved by library-versus-library screening. *Proc Natl Acad Sci USA* 107, 20941-20946, doi:10.1073/pnas.1011663107 (2010).
14. Hui, D. Y. & Howles, P. N. Carboxyl ester lipase: structure-function relationship and physiological role in lipoprotein metabolism and atherosclerosis. *J Lipid Res* 43, 2017-2030 (2002).
15. Aubert-Jousset, E., Sbarra, V. & Lombardo, D. Site-directed mutagenesis of the distal basic cluster of pancreatic bile salt-dependent lipase. *J Biol Chem* 279, 39697-39704 (2004).
16. Cheng, J. B. & Russell, D. W. Mammalian wax biosynthesis. I. Identification of two fatty acyl-Coenzyme A reductases with different substrate specificities and tissue distributions. *J Biol Chem* 279, 37789-37797, doi:10.1074/jbc.M406225200 (2004).
17. Cheng, J. B. & Russell, D. W. Mammalian wax biosynthesis. II. Expression cloning of wax synthase cDNAs encoding a member of the acyltransferase enzyme family. *J Biol Chem* 279, 37798-37807, doi:10.1074/jbc.M406226200 (2004).

18 Harris, C. A. et al. DGAT enzymes are required for triacylglycerol synthesis and lipid droplets in adipocytes. *J Lipid Res* 52, 657-667, doi:10.1194/jlr.M013003 (2011).

19 Cases, S. et al. ACAT-2, a second mammalian acyl-CoA: cholesterol acyltransferase. Its cloning, expression, and characterization. *J Biol Chem* 273, 26755-26764 (1998).

20. King, A. J. et al. Diacylglycerol acyltransferase 1 inhibition lowers serum triglycerides in the Zucker fatty rat and the hyperlipidemic hamster. *J Pharmacol Exp Ther* 330, 526-531, (2009).
21. Bocan, T. M., Mueller, S. B., Uhlendorf, P. D., Newton, R. S. & Krause, B. R. Comparison of CI-976, an ACAT inhibitor, and selected lipid-lowering agents for antiatherosclerotic activity in iliac-femoral and thoracic aortic lesions. A biochemical, morphological, and morphometric evaluation. *Arterioscler Thromb* 11, 1830-1843 (1991).
22. Cases, S. et al. Cloning of DGAT2, a second mammalian diacylglycerol acyltransferase, and related family members. *J Biol Chem* 276, 38870-38876, 2001.
23. Zhang, Y., Gaekwad, J., Wolfert, M. A. & Boons, G.-J. Synthetic tetra-acylated derivatives of lipid A from *Porphyromonas gingivalis* are antagonists of human TLR4. *Organic & biomolecular chemistry* 6, 3371-3381, (2008).
24. Herman M A, Peroni O D, Villoria J, Schon M R, Abumrad N A, Bluher M, Klein S, Kahn B B. (2011). Adipose Tissue Carbohydrate Responsive-Element Binding Protein Regulates Adipose Tissue Fatty Acid Synthesis and Glucose Homeostasis. *Nature* 484: 333-338 (2012).
25. Herman M A, Peroni O D, Kahn B B (2009). Carbohydrate Response Element Binding Protein in Adipose Tissue Regulates DeNovo Lipogenesis and Glucose Homeostasis. Presented at the American Diabetes Association Science Sessions. 2009. *Diabetes* 58, suppl. 1, A351.
26. Hohmeier, H. E., Mulder, H., Chen, G., Henkel-Rieger, R., Prentki, M. & Newgard, C. B. (2000). Isolation of INS-1-derived cell lines with robust ATP-sensitive K+ channel-dependent and -independent glucose-stimulated insulin secretion. *Diabetes* 49, 424-430.
27. Tozzo, E., Shepherd, P. R., Gnudi, L., and Kahn, B. B. (1995). Transgenic GLUT-4 overexpression in fat enhances glucose metabolism: preferential effect on fatty acid synthesis. Am J Physiol 268, E956-964.
28. Hirasawa, A., Tsumaya, K., Awaji, T., Katsuma, S., Adachi, T., Yamada, M., Sugimoto, Y., Miyazaki, S., and Tsujimoto, G. (2005). Free fatty acids regulate gut incretin glucagon-like peptide-1 secretion through GPR120. Nat Med 11, 90-94.
29. Oh, D. Y., Talukdar, S., Bae, E. J., Imamura, T., Morinaga, H., Fan, W., Li, P., Lu, W. J., Watkins, S. M., and Olefsky, J. M. (2010). GPR120 is an omega-3 fatty acid receptor mediating potent anti-inflammatory and insulin-sensitizing effects. *Cell* 142, 687-698.

It should be understood that for all numerical bounds describing some parameter in this application, such as "about," "at least," "less than," and "more than," the description also necessarily encompasses any range bounded by the recited values. Accordingly, for example, the description at least 1, 2, 3, 4, or 5 also describes, inter alia, the ranges 1-2, 1-3, 1-4, 1-5, 2-3, 2-4, 2-5, 3-4, 3-5, and 4-5, et cetera.

It should be understood that for all numerical bounds describing some parameter in this application, such as "about," "at least," "less than," and "more than," the description also necessarily encompasses any range bounded by the recited values. Accordingly, for example, the description at least 1, 2, 3, 4, or 5 also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that it is incorporated by reference in its entirety for all purposes as well as for the proposition that is recited. Where any conflict exits between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures) are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g. elements, including numerical ranges and exemplary embodiments) of particular embodiments and aspects of the invention including the working examples. For example, particular experimental parameters exemplified in the working examples can be adapted for use in the methods provided by the invention piecemeal without departing from the invention. For example, for materials that are disclosed or used in the methods provided by the invention, while specific reference of each various individual and collective combinations and permutation of these compounds may not be explicitly disclosed, each is specifically contemplated and described herein. Thus, if a class of elements A, B, and C are disclosed as well as a class of elements D, E, and F and an example of a combination of elements, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus to the extent an element is described in one or more references known to the person having ordinary skill in the art, they may be excluded from the claimed invention by, inter alia, a negative proviso or disclaimer of the feature or combination of features.

While this invention has been particularly shown and described with references to example embodiments thereof, it will be understood by those skilled in the art that various changes in form and details may be made therein without departing from the scope of the invention encompassed by the appended claims.

What is claimed is:

1. A compound according to the formula:

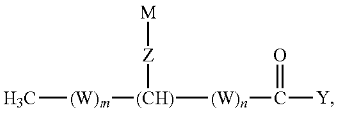

or a salt thereof, wherein:

m is an integer from 0 to 21;

n is an integer from 0 to 21;

the sum of m and n is an integer from 11 to 21;

W, for each occurrence, is independently ($CR^1R^2$) or ($C(R^3)=C(R^4)$);

$R^1$ and $R^2$, for each occurrence, are independently selected from H, ($C_6$-$C_{12}$)aryl, or ($C_1$-$C_{12}$)alkyl;

$R^3$ and $R^4$, for each occurrence, are independently selected from H, ($C_6$-$C_{12}$)aryl, ($C_5$-$C_{12}$)heteroaryl, —(CO)($C_1$-$C_6$)alkyl, ($C_1$-$C_{12}$)alkyl, ($C_1$-$C_{12}$)alkoxy, or hydroxyl;

Z is —O(CO)O—, —O(CO)NH—, or —NH(CO)O—;

Y is OH or $OR^5$;

$R^5$ is ($C_1$-$C_{12}$)alkyl, ($C_6$-$C_{12}$)aryl, ($C_5$-$C_{12}$)heteroaryl, or ($C_{12}$-$C_{24}$)alkenyl; and M is $(CH_2)_{11-23}CH_3$.

* * * * *